(12) United States Patent
Khoshnevis et al.

(10) Patent No.: US 10,219,877 B2
(45) Date of Patent: *Mar. 5, 2019

(54) ORTHODONTIC APPLIANCE WITH SNAP FITTED, NON-SLIDING ARCHWIRE

(71) Applicant: University of Southern California, Los Angeles, CA (US)

(72) Inventors: Behrokh Khoshnevis, Marina del Rey, CA (US); Hongsheng Tong, Yorba Linda, CA (US); Yong Chen, Burbank, CA (US); Philong John Pham, Huntington Beach, CA (US); Robert Lee, Torrance, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,198

(22) Filed: Aug. 26, 2016

(65) Prior Publication Data

US 2016/0361141 A1 Dec. 15, 2016

Related U.S. Application Data

(63) Continuation of application No. 14/067,690, filed on Oct. 30, 2013, now Pat. No. 9,427,291.

(Continued)

(51) Int. Cl.
*A61C 7/30* (2006.01)
*A61C 7/12* (2006.01)
(Continued)

(52) U.S. Cl.
CPC ................. *A61C 7/30* (2013.01); *A61C 7/125* (2013.01); *A61C 7/28* (2013.01); *A61C 7/20* (2013.01)

(58) Field of Classification Search
CPC ....................................................... A61C 7/12
See application file for complete search history.

(56) References Cited

U.S. PATENT DOCUMENTS 3,256,602 A 6/1966 Broussard
3,374,542 A 3/1968 Moylan, Jr.
(Continued)

FOREIGN PATENT DOCUMENTS

EP 2076207 7/2009
EP 2617383 7/2013
(Continued)

OTHER PUBLICATIONS

U.S. Appl. No. 15/249,262, filed Aug. 26, 2016, Tong et al.
(Continued)

*Primary Examiner* — Edward Moran
(74) *Attorney, Agent, or Firm* — Knobbe Martens Olson & Bear LLP

(57) ABSTRACT

An orthodontic appliance may include an archwire and multiple orthodontic brackets. The archwire may fit within a human mouth and contain multiple male connectors. Each orthodontic bracket may have a configuration that facilitates attaching the orthodontic bracket to a single tooth. Each orthodontic bracket may allow one of the male connectors to be locked into the orthodontic bracket with a snapping action. The male connector may be unable to slide with respect to the orthodontic bracket after being locked in the orthodontic bracket. A manual unlocking action may allow the male connector to disengage from the orthodontic bracket.

17 Claims, 45 Drawing Sheets

Related U.S. Application Data

(60) Provisional application No. 61/720,263, filed on Oct. 30, 2012.

(51) Int. Cl.
*A61C 7/28* (2006.01)
*A61C 7/20* (2006.01)

(56) References Cited

U.S. PATENT DOCUMENTS

| | | |
|---|---|---|
| 3,593,421 A | 7/1971 | Brader |
| 3,762,050 A * | 10/1973 | Dal Pont ............ A61C 7/12 433/20 |
| 3,878,610 A | 4/1975 | Coscina |
| 3,936,938 A | 2/1976 | Northcutt |
| 3,975,823 A | 8/1976 | Sosnay |
| 4,103,423 A | 8/1978 | Kessel |
| 4,197,643 A | 4/1980 | Burstone et al. |
| 4,330,273 A | 5/1982 | Kesling |
| 4,354,834 A | 10/1982 | Wilson |
| 4,385,890 A | 5/1983 | Klein |
| 4,436,510 A | 3/1984 | Klein |
| 4,561,844 A | 12/1985 | Bates |
| 4,582,487 A | 4/1986 | Creekmore |
| 4,585,414 A | 4/1986 | Kottermann |
| 4,659,310 A | 4/1987 | Kottermann |
| 4,664,626 A | 5/1987 | Kesling |
| 4,674,978 A | 6/1987 | Acevedo |
| 4,676,747 A | 6/1987 | Kesling |
| 4,725,229 A | 2/1988 | Miller |
| 4,842,514 A | 6/1989 | Kesling |
| 4,872,449 A | 10/1989 | Beeuwkes |
| 4,978,323 A | 12/1990 | Freedman |
| 5,055,039 A | 10/1991 | Abbatte et al. |
| 5,092,768 A | 3/1992 | Korn |
| 5,127,828 A | 7/1992 | Suyama |
| 5,174,754 A | 12/1992 | Meritt |
| 5,176,618 A | 1/1993 | Freedman |
| 5,344,315 A | 9/1994 | Hanson |
| 5,368,478 A | 11/1994 | Andreiko |
| 5,380,197 A | 1/1995 | Hanson |
| 5,399,087 A | 3/1995 | Arndt |
| 5,431,562 A | 7/1995 | Andreiko |
| 5,447,432 A | 9/1995 | Andreiko |
| 5,454,717 A | 10/1995 | Andreiko |
| 5,516,284 A | 5/1996 | Wildman |
| 5,630,715 A | 5/1997 | Voudouris |
| 5,683,243 A | 11/1997 | Andreiko |
| 5,722,827 A | 3/1998 | Allesee |
| 5,816,800 A | 10/1998 | Brehm |
| 5,820,370 A | 10/1998 | Brosius |
| 5,863,198 A | 1/1999 | Doyle |
| 6,015,289 A | 1/2000 | Andreiko |
| 6,036,489 A | 3/2000 | Brosius |
| 6,086,364 A | 7/2000 | Brunson |
| 6,089,861 A | 7/2000 | Kelly |
| 6,095,809 A | 8/2000 | Kelly et al. |
| 6,183,250 B1 | 2/2001 | Kanno et al. |
| 6,190,166 B1 | 2/2001 | Sasakura |
| 6,196,839 B1 | 3/2001 | Ross |
| 6,244,861 B1 | 6/2001 | Andreiko |
| 6,250,918 B1 | 6/2001 | Sachdeva et al. |
| 6,318,995 B1 | 11/2001 | Sachdeva et al. |
| 6,612,143 B1 | 9/2003 | Butscher et al. |
| 6,616,444 B2 | 9/2003 | Andreiko |
| 6,632,089 B2 | 10/2003 | Rubbert |
| 6,648,640 B2 | 11/2003 | Rubbert |
| 6,663,385 B2 | 12/2003 | Tepper |
| 6,679,700 B2 | 1/2004 | McGann |
| 6,682,344 B1 | 1/2004 | Stockstill |
| 6,732,558 B2 | 5/2004 | Butscher et al. |
| 6,733,287 B2 | 5/2004 | Wilkerson |
| 6,736,638 B1 | 5/2004 | Sachdeva et al. |
| 6,739,869 B1 | 5/2004 | Taub et al. |
| 6,755,064 B2 | 6/2004 | Butscher |
| 6,776,614 B2 | 8/2004 | Wiechmann |
| 6,846,179 B2 | 1/2005 | Chapouland |
| 6,860,132 B2 | 3/2005 | Butscher |
| 6,971,873 B2 | 12/2005 | Sachdeva |
| 6,988,889 B2 | 1/2006 | Abels |
| 7,008,221 B2 | 3/2006 | McGann |
| 7,013,191 B2 | 3/2006 | Rubbert |
| 7,029,275 B2 | 4/2006 | Rubbert |
| 7,033,171 B2 | 4/2006 | Wilkerson |
| 7,037,107 B2 | 5/2006 | Yamamoto |
| 7,063,531 B2 | 6/2006 | Maijer et al. |
| 7,076,980 B2 | 7/2006 | Butscher |
| 7,077,646 B2 | 7/2006 | Hilliard |
| 7,134,874 B2 | 11/2006 | Chishti et al. |
| 7,186,115 B2 | 3/2007 | Goldberg et al. |
| 7,214,056 B2 | 5/2007 | Stockstill |
| 7,229,282 B2 | 6/2007 | Andreiko |
| 7,234,936 B2 | 6/2007 | Lai |
| 7,244,121 B2 | 7/2007 | Brosius |
| 7,245,977 B1 | 7/2007 | Simkins |
| 7,283,891 B2 | 10/2007 | Butscher |
| 7,296,996 B2 | 11/2007 | Sachdeva |
| 7,347,688 B2 | 3/2008 | Kopelman et al. |
| 7,361,017 B2 | 4/2008 | Sachdeva |
| 7,585,172 B2 | 9/2009 | Rubbert |
| 7,590,462 B2 | 9/2009 | Rubbert |
| 7,621,743 B2 | 11/2009 | Bathen |
| 7,641,473 B2 | 1/2010 | Sporbert |
| 7,677,887 B2 | 3/2010 | Nicholson |
| 7,717,708 B2 | 5/2010 | Sachdeva |
| 7,726,968 B2 | 6/2010 | Raby et al. |
| 7,751,925 B2 | 7/2010 | Rubbert |
| 7,811,087 B2 | 10/2010 | Wiechmann |
| 7,837,466 B2 | 11/2010 | Griffith et al. |
| 7,837,467 B2 | 11/2010 | Butscher |
| 7,845,938 B2 | 12/2010 | Kim et al. |
| 7,850,451 B2 | 12/2010 | Wiechmann |
| 8,029,275 B2 | 10/2011 | Kesling |
| 8,047,034 B2 | 11/2011 | Butscher |
| 8,057,226 B2 | 11/2011 | Wiechmann |
| 8,082,769 B2 | 12/2011 | Butscher |
| 8,113,828 B1 | 2/2012 | Greenfield |
| 8,121,718 B2 | 2/2012 | Rubbert |
| 8,142,187 B2 | 3/2012 | Sporbert |
| 8,192,197 B2 | 6/2012 | Sporbert |
| 8,194,067 B2 | 6/2012 | Raby |
| 8,266,940 B2 | 9/2012 | Riemeir et al. |
| 8,297,970 B2 | 10/2012 | Kanomi |
| 8,366,440 B2 | 2/2013 | Bathen |
| 8,376,739 B2 | 2/2013 | Dupray |
| 8,382,917 B2 | 2/2013 | Johnson |
| 8,393,896 B2 | 3/2013 | Oda |
| 8,417,366 B2 | 4/2013 | Getto |
| 8,465,279 B2 | 6/2013 | Bathen |
| 8,485,816 B2 | 7/2013 | Macchi |
| 8,591,225 B2 | 11/2013 | Wu et al. |
| 8,678,818 B2 | 3/2014 | Dupray |
| 8,690,568 B2 | 4/2014 | Chapouland |
| 8,805,048 B2 | 8/2014 | Batesole |
| 8,936,464 B2 | 1/2015 | Kopelman |
| 8,961,172 B2 | 2/2015 | Dupray |
| 8,979,528 B2 | 3/2015 | Macchi |
| 8,992,215 B2 | 3/2015 | Chapouland |
| 9,089,386 B2 | 7/2015 | Hagelganz |
| 9,127,338 B2 | 9/2015 | Johnson |
| 9,144,473 B2 | 9/2015 | Aldo |
| 9,402,695 B2 | 8/2016 | Curiel et al. |
| 9,427,291 B2 | 8/2016 | Khoshnevis et al. |
| 9,439,737 B2 | 9/2016 | Gonzales et al. |
| 9,492,246 B2 | 11/2016 | Lin |
| 9,498,302 B1 | 11/2016 | Patel |
| 9,554,875 B2 | 1/2017 | Gualano |
| 9,585,733 B2 | 3/2017 | Voudouris |
| 9,610,628 B2 | 4/2017 | Riemeier |
| 9,622,834 B2 | 4/2017 | Chapouland |
| 9,707,056 B2 | 7/2017 | Machata et al. |
| 9,814,543 B2 | 11/2017 | Huang et al. |
| 9,867,678 B2 | 1/2018 | Macchi |
| 9,872,741 B2 | 1/2018 | Gualano |

(56) References Cited

U.S. PATENT DOCUMENTS

| | | | |
|---|---|---|---|
| 9,987,105 | B2 | 6/2018 | Dupray |
| 10,045,834 | B2 | 8/2018 | Gualano |
| 2003/0180689 | A1 | 9/2003 | Arx et al. |
| 2004/0072120 | A1 | 4/2004 | Lauren |
| 2004/0166459 | A1 | 8/2004 | Voudouris |
| 2004/0219471 | A1 | 11/2004 | Cleary et al. |
| 2005/0244781 | A1 | 11/2005 | Abels et al. |
| 2007/0031773 | A1 | 2/2007 | Scuzzo |
| 2007/0111154 | A1 | 5/2007 | Sampermans |
| 2007/0141525 | A1 | 6/2007 | Cinader, Jr. |
| 2007/0154859 | A1* | 7/2007 | Hilliard .................... A61C 7/02 433/20 |
| 2008/0032250 | A1 | 2/2008 | Kopelman et al. |
| 2008/0254403 | A1 | 10/2008 | Hilliard |
| 2009/0220907 | A1 | 9/2009 | Suyama |
| 2010/0105000 | A1 | 4/2010 | Scommegna |
| 2010/0179789 | A1 | 7/2010 | Sachdeva et al. |
| 2010/0304321 | A1 | 12/2010 | Patel |
| 2012/0148972 | A1 | 6/2012 | Lewis |
| 2013/0065193 | A1 | 3/2013 | Curiel et al. |
| 2013/0196281 | A1 | 8/2013 | Thornton |
| 2014/0120491 | A1 | 5/2014 | Khoshnevis et al. |
| 2014/0287376 | A1 | 9/2014 | Hultgren et al. |
| 2015/0064641 | A1 | 3/2015 | Gardner |
| 2015/0072299 | A1 | 3/2015 | Alauddin et al. |
| 2016/0074139 | A1 | 3/2016 | Machata et al. |
| 2016/0166357 | A1 | 6/2016 | Portalupi |
| 2017/0156823 | A1 | 6/2017 | Roein et al. |
| 2017/0165532 | A1 | 6/2017 | Khan et al. |
| 2017/0196660 | A1 | 7/2017 | Lee |
| 2017/0224444 | A1 | 8/2017 | Viecilli et al. |
| 2017/0296304 | A1 | 10/2017 | Tong et al. |

FOREIGN PATENT DOCUMENTS

| | | |
|---|---|---|
| RU | 133408 U1 | 10/2013 |
| WO | WO 01/80761 | 11/2001 |
| WO | WO 01/85047 | 11/2001 |
| WO | WO 2005/008441 | 1/2005 |
| WO | WO 2008/051774 | 5/2008 |
| WO | WO 2011/034522 | 3/2011 |
| WO | WO 2011/090502 | 7/2011 |
| WO | WO 2011/103669 | 9/2011 |
| WO | WO 2012/089735 | 7/2012 |
| WO | WO 2012/140021 | 10/2012 |
| WO | WO 2013/019398 | 2/2013 |
| WO | WO 2016/199972 | 12/2016 |
| WO | WO 2017198640 A1 | 11/2017 |

OTHER PUBLICATIONS

Coro, Jorge C. et al, "MEAW Therapy" MEAW Therapy-Orthodontic Products, accessed via http://www.orthodonticproductsonline.com/2012/11/meas-therapy/ on Mar. 14, 2016, published Nov. 12, 2012 in 6 pages.

ElSheikh, Moaaz Mohamed, et al. "A Forsus Distalizer: A Pilot Typodont Study". Jul.-Dec. 2004, KDJ, vol. 7, No. 2, pp. 107-115.

EP Search Report dated Jun. 23, 2016 in EP application No. 13850778.5 in 5 pages.

Glauser-Williams Orthodontics: Appliances, http://www.glauserwilliamsorthodontics.com/treatments/orthodontic-appliances.php, accessed Nov. 30, 2015, in 4 pages.

Korean Intellectual Property Office (ISA/KR), International Search Report and Written Opinion of the International Searching Authority, dated Feb. 14, 2014, for PCT Application No. PCT/US2013/067560, filed Oct. 30, 2013, entitled Orthodontic Appliance with Snap Fitted, Non-Sliding Archwire.

Mahony, Derek, "How We Got From There to Here and Back". Dental Learning Hub (Capture of web page dated Jun. 24, 2013 downloaded from http://web.archive.org/web/20130624145806/http://www.dental-learninghub.com/Clinical/Orthodontics.aspx, downloaded Feb. 7, 2014).

Miller, R.J. et al. "Validation of Align Technology's Treat III™ Digital Model Superimposition Tool and Its Case Application". Orthodontic Craniofacial Res.,2003, vol. 6 (Suppl 1): pp. 143-149.

SureSmile. 2013. About SureSmile. (Capture of web page dated Jun. 21, 2013 downloaded from http://web.archive.org/web/20130621031404/http://suresmile.com/About-SureSmile, downloaded Feb. 7, 2014).

Yang, Won-Sik, et al. "A Study of the Regional Load Deflection Rate of Multiloop Edgewise Arch Wire." Angle Orthodontist, 2001, vol. 7, No. 2, pp. 103-109.

International Search Report for International Application No. PCT/US2017/028180 dated Aug. 14, 2017.

Gilbert, Alfredo. An in-office wire-bending robot for lingual orthodontics. ResearchGate. Article in Journal of clinical orthodontics: JCO, Apr. 2011.

Jiang et al. Bending Process Analysis and Structure Design of Orthodontic Archwire Bending Robot. International Journal of Smart Home. vol. 7, No. 5 (2013), pp. 345-352. http://dx.doi.org/10.14257/ijsh.2013.7.5.33.

Jiang et al. A Review on Robot in Prosthodontics and Orthodontics. Hindawi Publishing Corporation. Advances in Mechanical Engineering. Article ID 198748. 2014. 11 pages.

Xia, et al. Development of a Robotic System for Orthodontic Archwire Bending. 2016 IEEE International Conference on Robotics and Automation (ICRA). Stockholm, Sweden, May 16-21, 2016. pp. 730-735.

International Search Report for International Application No. PCT/US2018/016293 dated May 10, 2018.

International Search Report and Written Opinion for International Application No. PCT/US 2017/064021 dated Mar. 2, 2018.

International Search Report for International Application No. PCT/US2018/028437 dated Aug. 9, 2018.

* cited by examiner

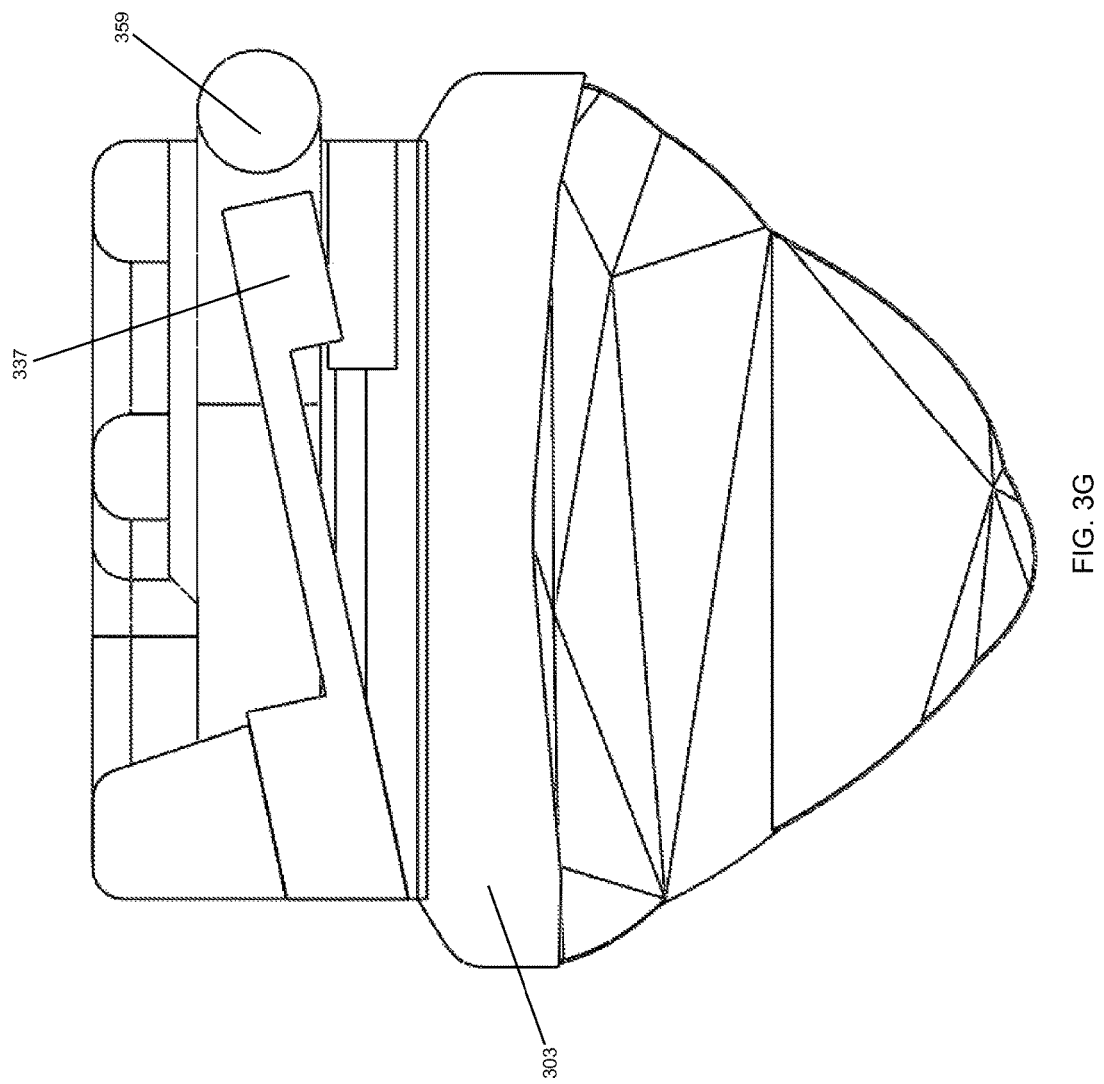

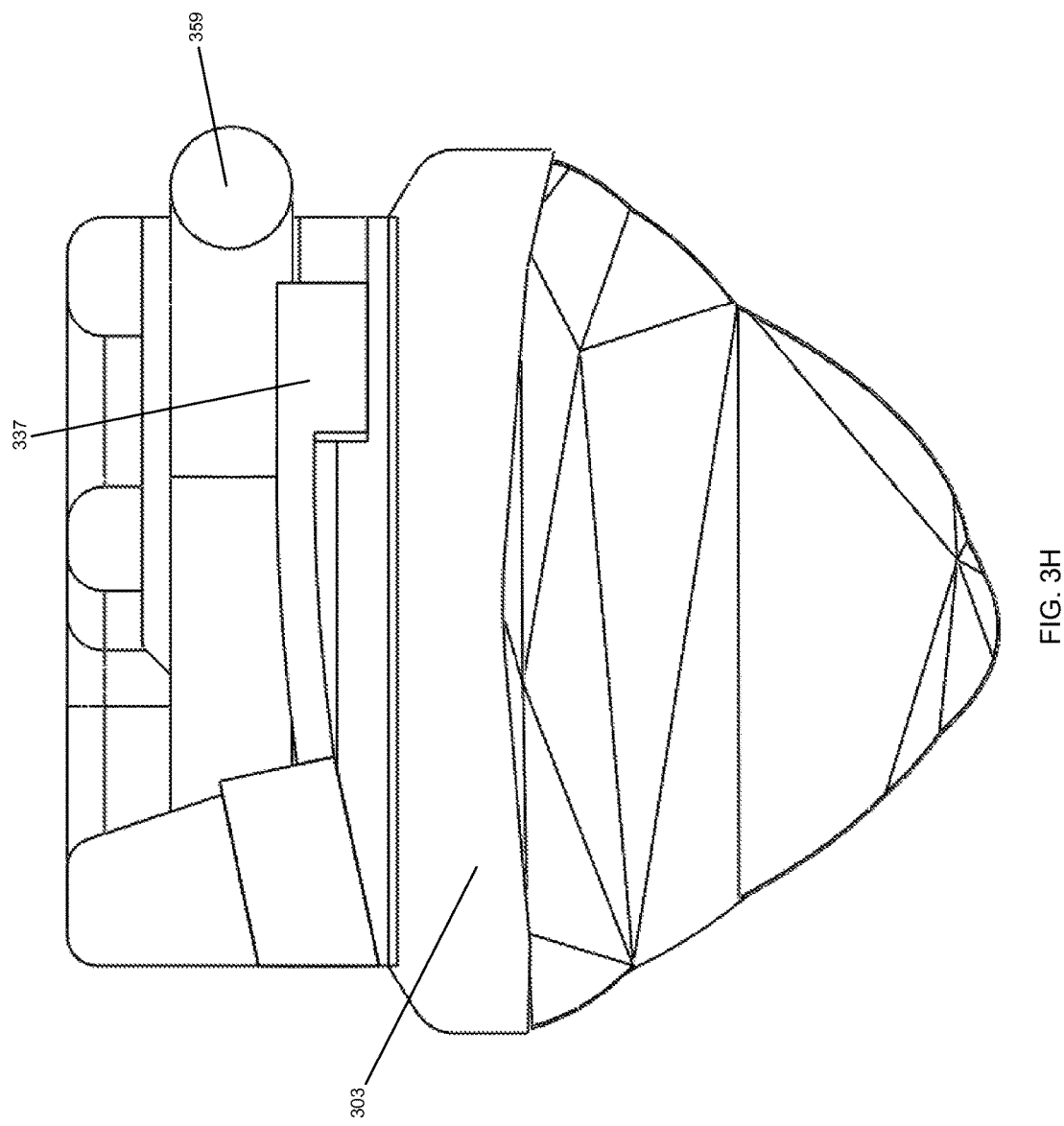

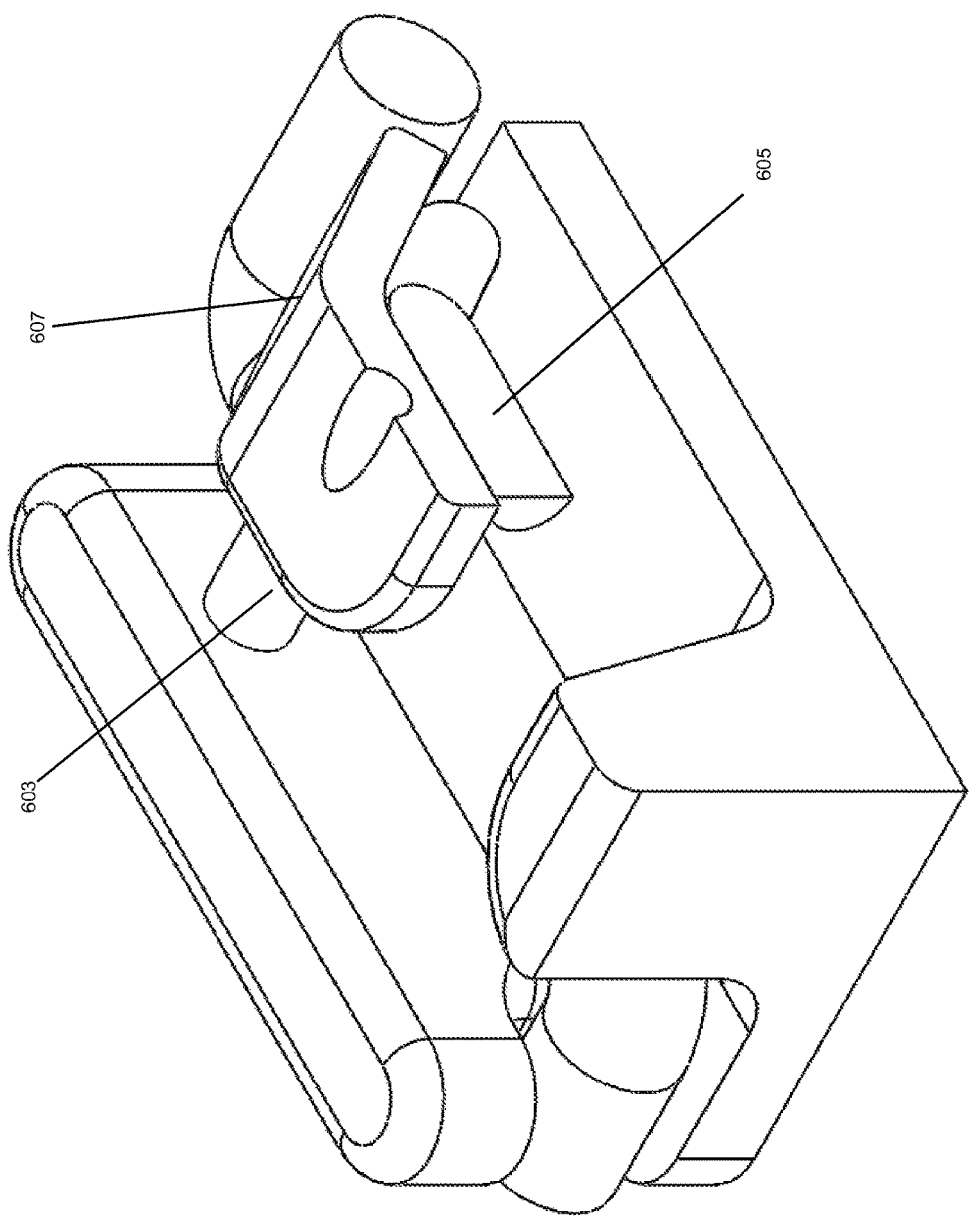

ORTHODONTIC APPLIANCE WITH SNAP FITTED, NON-SLIDING ARCHWIRE

CROSS-REFERENCE TO RELATED APPLICATIONS

This application claims the benefit as a continuation application of U.S. Pat. App. No. 14/067,690 filed on Oct. 30, 2013, which in turn claims priority to U.S. provisional patent application 61/720,263, entitled "Frictionless, Self-Activating, Self-Limiting, and Self-Contained Orthodontic Appliance " filed Oct. 30, 2012. The entire content of the foregoing applications are hereby incorporated herein by reference in their entireties.

BACKGROUND

Technical Field

This disclosure relates to orthodontic appliances, including archwires and associated orthodontic brackets.

Description of Related Art

Orthodontic appliances are commonly used to correct misaligned teeth.

There are many types of orthodontic appliances. However, each may have drawbacks, such as requiring too much time to prepare and/or install.

One type of orthodontic appliance is the pin and tube appliance. The pin and tube appliance can control the movement and position of each tooth in three-dimensional space. It can include an orthodontic archwire with a male "pin" that inserts into a female vertical "tube" that is attached to the tooth. The pin and tube do not move relative to each other. Interproximal loops can be placed in between the teeth to move the teeth to open or close spaces.

However, the pin and tube appliance can present challenges, including:
  Custom bends and interdental loops may have to be bent manually in the archwire for the pins to fit into the vertical tubes and for the archwire to move the teeth to the desired location. This process may need to be performed manually by a human and may be very demanding and tedious.
  The male pin may need to be soldered onto the orthodontic archwire with a needed inclination. As the teeth move, the pins may need to be unsoldered and re-soldered to new locations. This may also be a very demanding and tedious manual process.
  The solder joint between the male pin and orthodontic archwire may break.
  The orthodontic archwire may be difficult to insert and remove from the patient because the locking mechanism may require bending the male insert over the tube to lock and un-bending the male insert from the tube to unlock.
  Stainless steel wires may be needed. Because of elastic limitations of stainless steel, many different size wires with different properties may need to be used for each case. The may complicate wire bending, pin soldering, and locking, and unlocking procedures when changing wires.
  The device may be ineffective in dealing with axial rotations of teeth.

Another type of orthodontic appliances is the edgewise appliance. An edgewise appliance may include orthodontic brackets (with rectangular slots) that are bonded onto each tooth. An archwire that is rectangular in cross-section may fit into rectangular slots in the orthodontic brackets.

However, the edgewise appliance can present problems, including:
  It may require significant custom wire bending along three axis (or three orders) due to differences in tooth size and tooth position. These axis may include in-out (first order bend), up-down (second order bend), and faciolingual inclination (3rd order bend).
  The wire may need to be tied to an orthodontic edgewise orthodontic bracket. This can be time consuming, especially if the brackets are behind the teeth, also known as lingual braces.
  Sliding the archwire with respect to the orthodontic bracket can require application of external forces. Frequent appointments may be required to ensure that these external forces do not overcorrect or undercorrect the amount of desired movement.
  This system may depend heavily on sliding between the orthodontic bracket and archwire to move teeth. However, the amount of sliding that can be achieved can be difficult to predict due to the unpredictable nature of the amount of friction to overcome. This can again require frequent monthly appointments to ensure that the tooth moves in the desired amount.

Another type of orthodontic appliances is the pre-adjusted, straight-wire appliance that uses nickel-titanium wires. This appliance can minimize the amount archwire bending that is required in edgewise appliances. The shape memory, super-elasticity, and lower modulus of elasticity features of shape memory alloys can lower the amount of force delivered to the teeth and significantly reduce the pathologic lesions as a result of heavy force use from rigid stainless steel wires. The large range of movement for some of shape memory alloy archwires can reduce the number of archwires required for treatment and, as such, reduce the number of activation appointments that are needed.

However, the pre-adjusted straight-wire appliance can present challenges. For example, considerable time may be required to tie the archwire into the orthodontic bracket, especially when lingual braces are used. The appliance may also still rely heavily on sliding the orthodontic bracket relative to the archwire to open and close space. To overcome the unpredictable amount of friction that is generated, frequent monthly appointments may still be required to ensure that the correct amount of movement is achieved.

Another type of orthodontic appliance uses self-ligating orthodontic brackets. These may reduce the amount of time and effort required to tie a wire into an orthodontic straight-wire appliance. Various types of doors and latches may be provided to replace tying the orthodontic wire. These doors and latches can make it easier to deliver and change orthodontic archwires. They can also eliminate the unnecessary tying and untying of archwires at appointments when the archwire does not need to be changed. Self-ligating orthodontic brackets can also provide a metal-to-metal interface between the orthodontic slot and the wire, reducing the amount of friction when moving teeth.

However, self-ligating orthodontic brackets can present problems, including:
  Self-ligating orthodontic brackets can sacrifice torque control of the teeth because of a high degree of orthodontic slop that can be present between the orthodontic slot and the archwire.
  Self-ligating orthodontic brackets may rely heavily on sliding the orthodontic bracket relative to the archwire to open and close space. Thus, frequent monthly appointments can still be required to ensure that the correct amount of movement is achieved.

Self-ligating orthodontic brackets can be bulkier than other types of orthodontic brackets. This can make control of the teeth much more difficult when using the orthodontic brackets on the lingual surface (behind the teeth) because there may be less interdental space between the orthodontic brackets, resulting in a much more rigid wire that can be harder to control.

Self-ligating orthodontic brackets can have several moving parts that can break under wear from occlusal forces in the mouth or from normal use of the appliance.

CAD/CAM technology can also be used in connection with orthodontics. This technology can be used to create an expected desired end result prior to the starting of orthodontic treatment. Customized wires and orthodontic brackets can be designed based on the expected desired end result of the orthodontic treatment to reduce the amount of doctor intervention required at each appointment.

However, using CAD/CAM technology may not overcome all of the problems associated with the orthodontic appliances, such as:

These customized appliances can rely heavily on sliding the orthodontic bracket relative to the archwire to open and close space. Thus, frequent appointments may still be required to ensure that adequate force is delivered to achieve sufficient tooth movement.

Customized orthodontic brackets can also be difficult to tie in, especially when placed on the lingual surface of the teeth.

Customized self-ligating orthodontic brackets can be bulky, difficult to control, and damage prone.

SUMMARY

An orthodontic appliance may include an archwire and multiple orthodontic brackets. The archwire may fit within a human mouth and contain multiple male connectors. Each orthodontic bracket may have a configuration that facilitates attaching the bracket to a single tooth. Each orthodontic bracket may allow one of the male connectors to be locked into the orthodontic bracket with a snapping action. The male connector may be unable to slide with respect to the orthodontic bracket after being locked in the orthodontic bracket. A manual unlocking action may allow the male connector to disengage from the orthodontic bracket.

Each male connector may be a male loop, have a U or rectangular shape, and or may be an integral portion of the archwire.

The archwire may include an interproximal loop between each neighboring set of male loops. The interproximal loops may face in the same or the opposite direction as the male loops. Each interproximal loop may be an integral portion of the archwire.

Each orthodontic bracket may have a slot into which a male connector is inserted during the snapping action. Each slot may have an inclined surface across which a portion of the male loop slides during the snapping action. Each inclined surface may end in an edge over which a portion of the male loop slides at the end of the snapping action.

Each slot may have two parallel rails that surround and contact an exterior portion of the male loop and prevent the male loop from moving laterally with respect to the orthodontic bracket after the male loop is inserted into the orthodontic bracket and locked by the snapping action.

Each slot may have a floor that contacts a side of the male loop and that comes between the male loop and the tooth to which the orthodontic bracket is attached after the male loop is inserted into the orthodontic bracket and locked by the snapping action.

Each slot may have a bridge that contacts an opposite side of the male loop after the male loop is inserted into the orthodontic bracket and locked by the snapping action.

Each inclined surface may bend while the male loop is being inserted into the orthodontic bracket and unbend at the end of the snapping action. Each inclined surface may instead not bend while the male loop is being inserted into the orthodontic bracket.

The archwire may include two legs connecting each male connector to the archwire. Each slot may include two concave portions that each seat one of the two legs during the locking.

Each male loop may have side legs. Each orthodontic bracket may include a stop that prevents the side legs from collapsing when the male loop is locked in the orthodontic bracket.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 1A illustrates an enlarged two-teeth section of the archwire; and FIG. 1B illustrates the entire archwire.

FIG. 2A illustrates an enlarged two-teeth section of the archwire; and FIG. 2B illustrates the entire archwire.

FIGS. 3A-3H illustrate an orthodontic bracket into which a male loop of an archwire may be snap fitted. FIG. 3A illustrates the orthodontic bracket without any male loop; FIG. 3B illustrates the orthodontic bracket after a loop has been snapped into the orthodontic bracket; FIG. 3C is a cross-section of the view illustrated in FIG. 3B taken along the broken line 3C-3C' in FIG. 3B; FIG. 3D is an occlusal view; FIG. 3E is a cross-section of the view illustrated in FIG. 3A taken along the line 3C-3C' in FIG. 3A with a springboard removed; FIG. 3F illustrates the orthodontic bracket without any male loop; FIG. 3G is a cross-section of the view illustrated in FIG. 3B taken along the broken line 3G/H-3G/H' in FIG. 3B when the distance between a free end of a springboard and a bridge is less than half the diameter of the male loop wire; and FIG. 3H is a cross-section of the view illustrated in FIG. 3B taken along the broken line 3G/H-3G/H' in FIG. 3B when the distance between the free end of the springboard and the bridge is more than the diameter of the male loop wire.

FIG. 4A illustrates the orthodontic bracket without any male loop; FIG. 4B illustrates the orthodontic bracket after the male loop has been snapped into the orthodontic bracket; FIG. 4C is a cross-section of the view in FIG. 4B taken along the broken line 4C/D/E-4C/D/E' in FIG. 4B; FIG. 4D is a cross-section of the view in FIG. 4B taken along the broken line 4C/D/E-4C/D/E' in FIG. 4B when the distance between a free end of a springboard and a floor is less than half the diameter of the male loop wire; and FIG. 4E is a cross-section of the view in FIG. 4B taken along the broken line 4C/D/E-4C/D/E' in FIG. 4B when the distance between the free end of the springboard and the floor is more than the diameter of the male loop wire.

FIG. 5A illustrates the orthodontic bracket without any male loop; FIG. 5B illustrates the orthodontic bracket after a male loop has been snapped into the orthodontic bracket; FIG. 5C is a cross-section of the view in FIG. 5B taken along the broken line 5C/D/E-5C/D/E' in FIG. 5B; FIG. 5D is a cross-section of the view in FIG. 5B taken along the broken line 5C/D/E-5C/D/E' in FIG. 5B when the distance between a free end of a springboard and a floor is less than the half the diameter of the male loop wire; and FIG. 5E is a cross-section of the view in FIG. 5B taken along the broken line 5C/D/E-5C/D/E' in FIG. 5B when the distance between the free end of the springboard and the floor is more than the diameter of the male loop wire.

FIGS. 6A-6F illustrate a different configuration of an orthodontic bracket into which a male loop of an archwire may be snap fitted. FIG. 6A illustrates the orthodontic bracket without any male loop; FIG. 6B illustrates the orthodontic bracket after the male loop has been snapped into the orthodontic bracket; FIG. 6C is a bottom view of a bridge and springboard in FIG. 6B; FIG. 6D is a cross section of the view in FIG. 6B taken along the broken line 6D/E/F-6D/E/F' in FIG. 6B; FIG. 6E is a cross-section of the view in FIG. 6B taken along the broken line 6D/E/F-6D/E/F' in FIG. 6B when the distance between a free end of the springboard and a floor is less than the half the diameter of the male loop wire; and FIG. 6F is a cross-section of the view in FIG. 6B taken along the broken line 6D/E/F-6D/E/F' in FIG. 6B when the distance between the free end of the springboard and the floor is more than the diameter of the male loop wire.

FIG. 7A illustrates the orthodontic bracket without any male loop; FIG. 7B illustrates the orthodontic bracket after the male loop has been snapped into the orthodontic bracket; FIG. 7C is a cross-section of the view in FIG. 7B taken along the broken line 7C/E/F-7C/E/F' in FIG. 5B; FIG. 7D is a cross-section of the view in FIG. 7A taken along the broken line 7D-7D' in FIG. 7A; FIG. 7E is a cross-section of the view in FIG. 7B taken along the broken line 7C/E/F-7C/E/F' in FIG. 7B when the height of the springboard blocks the withdraw of the male loop; and FIG. 7F is a cross-section of the view in FIG. 7B taken along the broken line 7C/E/F-7C/E/F' in FIG. 7B when the male loop is lifted beyond the height of the springboard to allow withdraw of the male loop.

FIG. 8A illustrates the orthodontic bracket without any male loop; FIG. 8B illustrates the orthodontic bracket after the male loop has been snapped into the orthodontic bracket; FIG. 8C is a cross-section of the view in FIG. 8B taken along the broken line 8C/D/E-8C/D/E' in FIG. 8B; FIG. 8D is a cross-section of the view in FIG. 8B taken along the broken line 8C/E/F-8C/E/F' in FIG. 8B when the height of the springboard blocks the withdraw of the male loop; and FIG. 8F is a cross-section of the view in FIG. 8B taken along the broken line 8C/E/F-8C/E/F' in FIG. 8B when the male loop is lifted beyond the height of the springboard to allow withdraw of the male loop.

FIG. 9A illustrates the orthodontic bracket and archwire in a snapped position; and FIG. 9B is a cross-section of the view in FIG. 9A taken along the broken line 9B-9B'.

FIG. 10A illustrates the different configuration of the archwire with a protuberance; FIG. 10B illustrates an example a self-ligating bracket that is modified to have a compartment; and FIG. 10C is a view of the bracket in FIG. 10A with a self-ligating door removed.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1A:
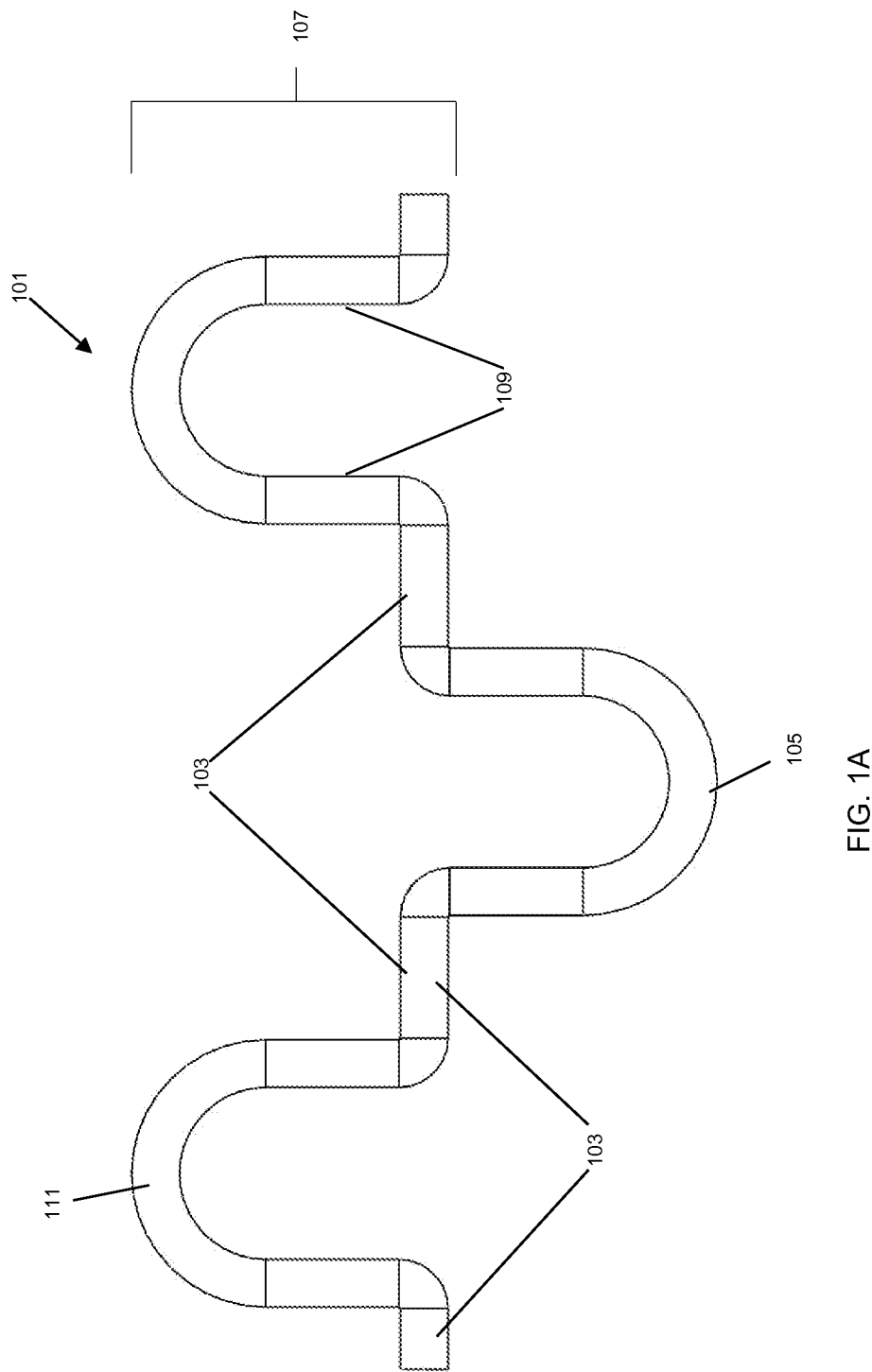
FIGS. 1A and 1B illustrate an archwire that includes male loops that are configured to be inserted from the gingival direction and that are separated by interproximal loops.
Figure 1B:
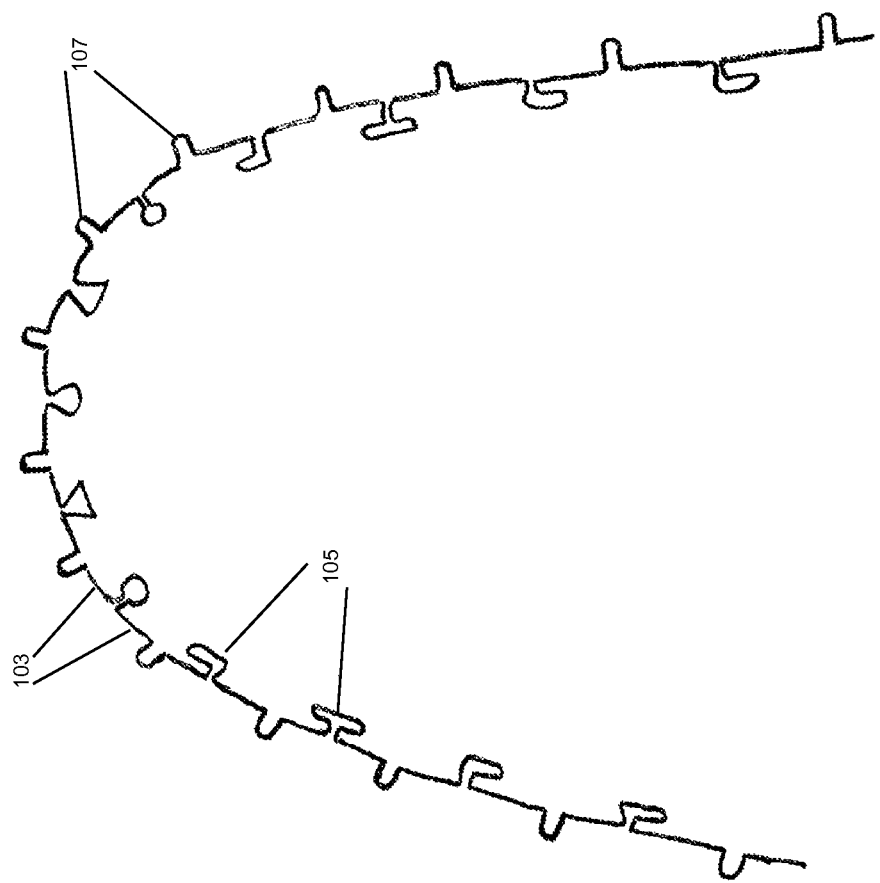

FIGS. 1A and 1B illustrate an archwire 101 that includes male loops 107 that each include legs 103, sidebars 109, and an arc portion 111. The male loops 107 may be configured to be inserted gingivally and may be separated by interproximal loops 105. The legs 103 may interconnect the male loops 107 and the interproximal loops 105. FIG. 1A illustrates an enlarged two-teeth section of the archwire 101; and FIG. 1B illustrates the entire archwire 101.

The male loops 107 of the archwire 101 may be configured to snap fit into an orthodontic bracket such that it will not slide with respect to the orthodontic bracket after it has been snap fit to the bracket. Examples of orthodontic brackets that may be used for this purpose are discussed below in connection with the discussion of FIGS. 1-9. Each orthodontic bracket may be bonded to a tooth and may serve to couple one of the male loops 107 to the tooth to which the orthodontic bracket is bonded and thus force the tooth to move in accordance with force that is applied to it by its male loop. The orthodontic force for moving teeth may come from the archwire 101 after it is deflected within its elastics limits and when each of its male loops are snapped into a corresponding orthodontic bracket.

The archwire 101 may be custom designed based on the position of the teeth when they are set in an expected finished alignment. The archwire 101 may be fabricated such that when the archwire 101 is deflected within its elastic range, the archwire 101 may return to its original shape reflecting the expected finished alignment of the teeth.

To engage the archwire 101 into an orthodontic bracket on a misaligned tooth, temporary deflections of the archwire 101 may take place. The archwire can be made of any material, such as a shape memory alloy, beta-titanium, or stainless steels.

Between each neighboring set of the male loops 107 may be one of the interproximal loops 105 located to correspond to an interdental space after installation. The male loops 107 may be connected to the interproximal loops 105 by the archwire legs 103. The archwire defines a longitudinal axis and each interproximal loop may comprise a mesial point on the longitudinal axis, a distal point on the longitudinal axis, and an incomplete loop between the mesial point and the distal point extending away from the longitudinal axis, the incomplete loop thereby may define a gap along the longitudinal axis forming an opening into the incomplete loop which may face in a gingival or occlusal direction.

Each male loop 107 may be configured in a U or rectangular shape so as to match a U or rectangular shape of a springboard that is part of the orthodontic bracket. Examples of springboards are also discussed below. Each of the male loops 107 may have two substantially parallel side bars 109 and the arc portion 111. The interproximal loops 105 located in the interdental space may have a different shape, such as U, T, tear-drop, triangular, rectangular, or boot shape. The archwire legs 103 may be parallel to the bite plane when they are left in a passive position. The directions of the male loops 107 may reflect the mesio-distal angulation and facio-lingual inclination of the teeth in the expected finishing setup of the teeth. The interproximal loops 105 may point towards the gingival direction, although they may not be all parallel to one another. Interproximal loops 105 may be oriented to be very close to but not touching the gums. One or more of the male loops 107 and/or interproximal loops 105 may be omitted and replaced by a straight wire, such as in the case of missing teeth or when their respective functions are not necessary. All of the legs 103, the interproximal loops 105, and the male loops 107 may be part of a single continuous wire, bent to form these sub-components. The single wire may not have any component attached to it prior to snapping it into the orthodontic brackets.

The male loops 107 may point to the occlusal direction when the orthodontic brackets are oriented in such a way as to allow the archwire 101 to be inserted from the gingival to the occlusal direction.

Users may instead wish to insert the archwire 101 from the occlusal to the gingival direction, in which case the male loops 107 may point to the gingival direction and the orthodontic brackets may be bonded to the tooth 180 degrees from the orientation needed for the insertion in the occlusal description.

Figure 2A:
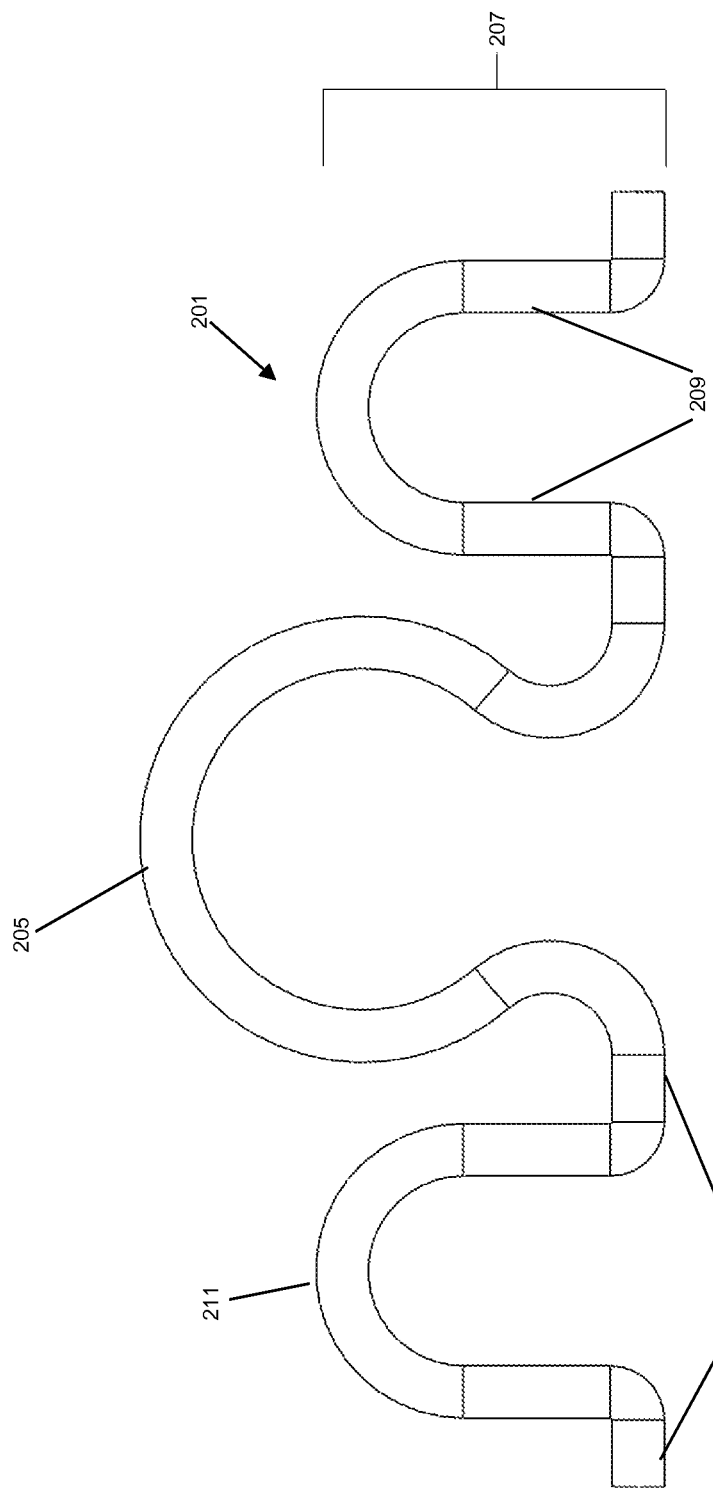
FIGS. 2A and 2B illustrate a different archwire that includes male loops that may be inserted from the occlusal direction and that are separated by interproximal loops.
Figure 2B:
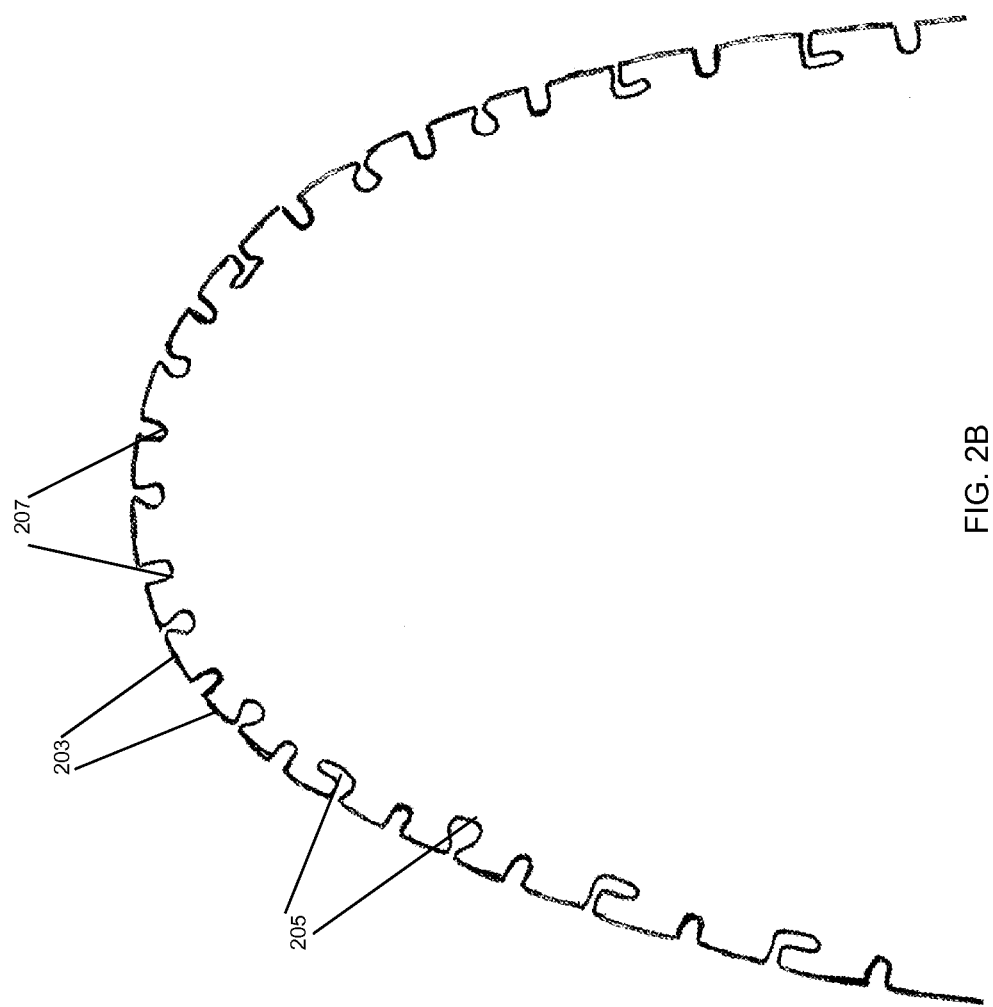

FIGS. 2A and 2B illustrate a different archwire 201 that may include male loops 207 that each includes legs 203, side bars 209, and an arc portion 211. The male loops 207 may be configured to be inserted from the occlusal direction and may be separated by interproximal loops 205. FIG. 2A illustrates an enlarged two-teeth section of the archwire 201; and FIG. 2B illustrates the entire archwire 201.

Each orthodontic bracket may be bonded to a tooth, oriented so that it has a mesial side towards the midline of the dental arch; a distal side that is away from the midline of the dental arch; a gingival side that is toward the gingivae; an occlusal side that is toward the biting surface of the teeth; a tooth side that is toward the tooth; and a non-tooth side that is away from the tooth. With respect to the descriptions of different orthodontic brackets that follow in connection with FIGS. 1-9, the descriptions assume use of the archwire 101 so that the male loops are inserted from the gingival to the occlusal direction. However, all of these orthodontic brackets may also be used with the archwire 201, in which case the male loops may be inserted from the occlusal to gingival direction. Each orthodontic bracket merely needs to be rotated by 180 degrees with respect to the tooth to which it is bonded.

Figure 3A:
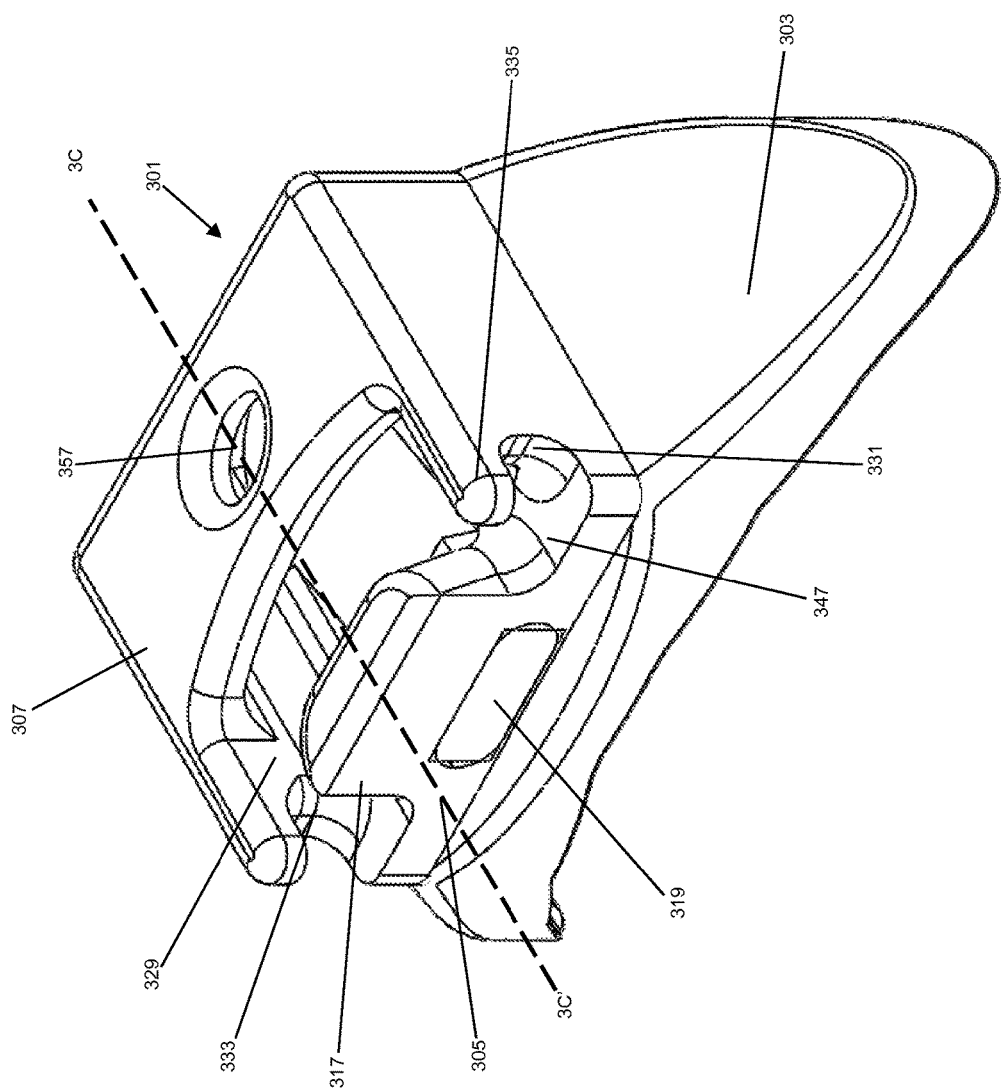
Figure 3B:
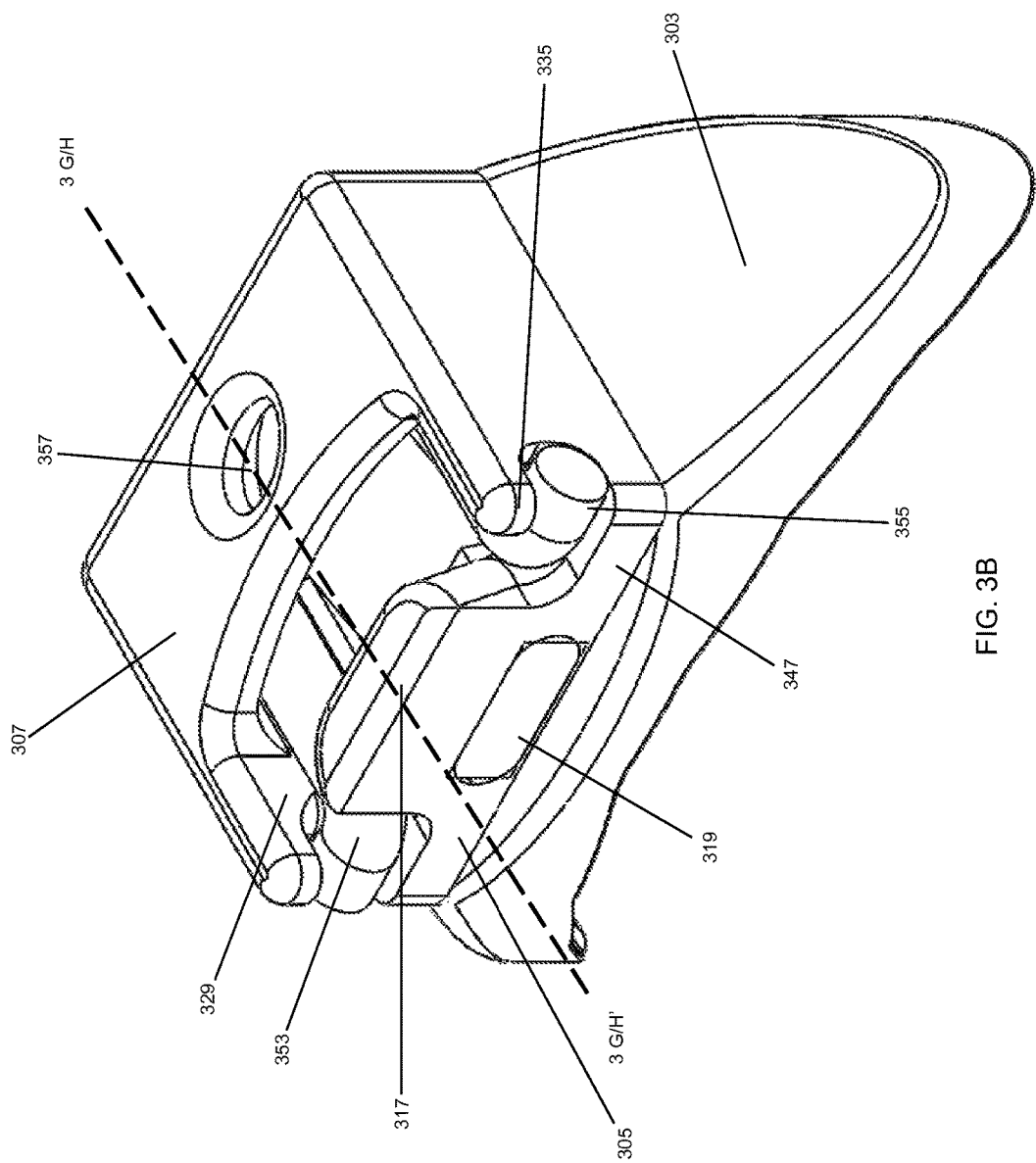
Figure 3C:
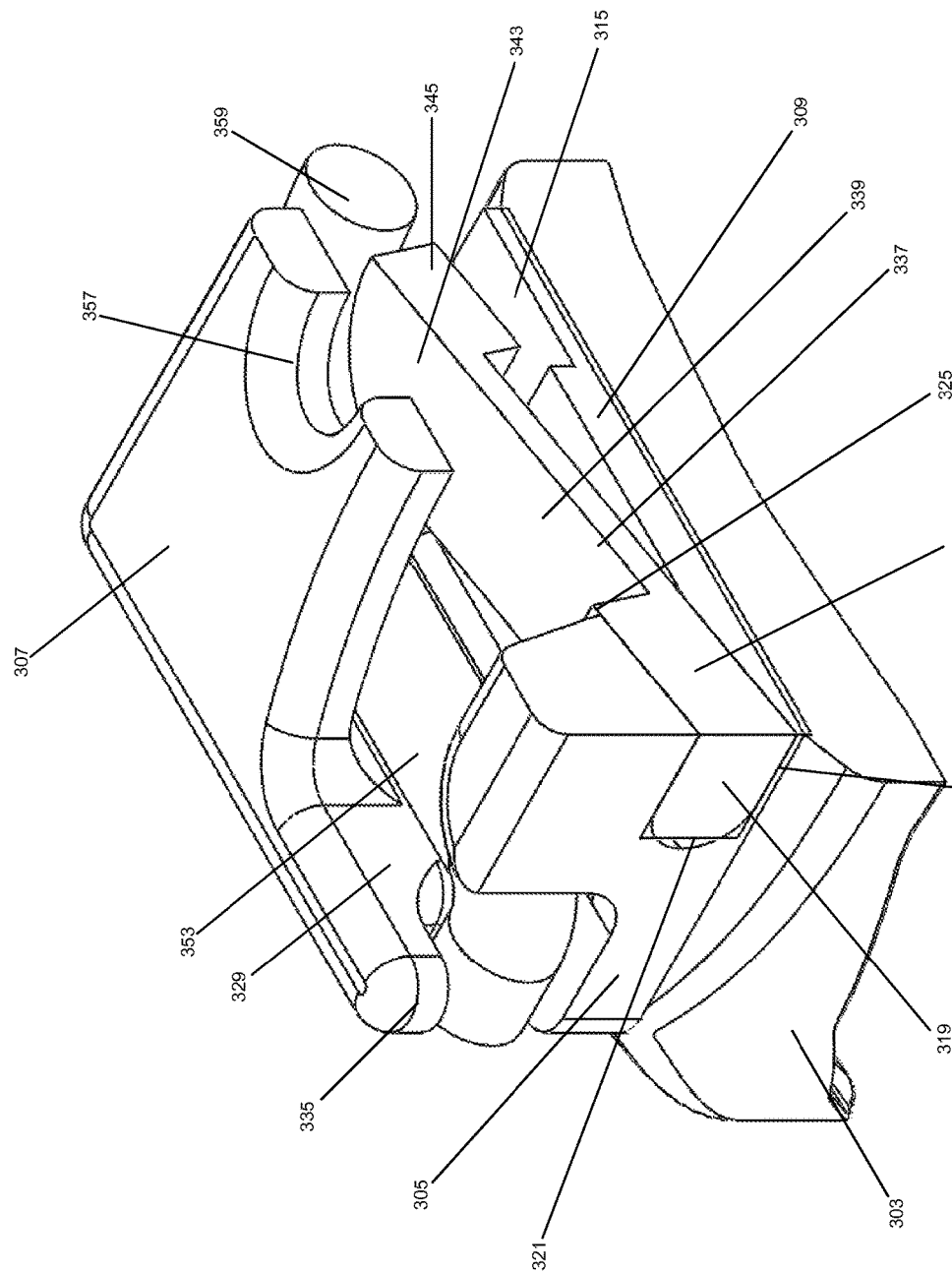
Figure 3D:
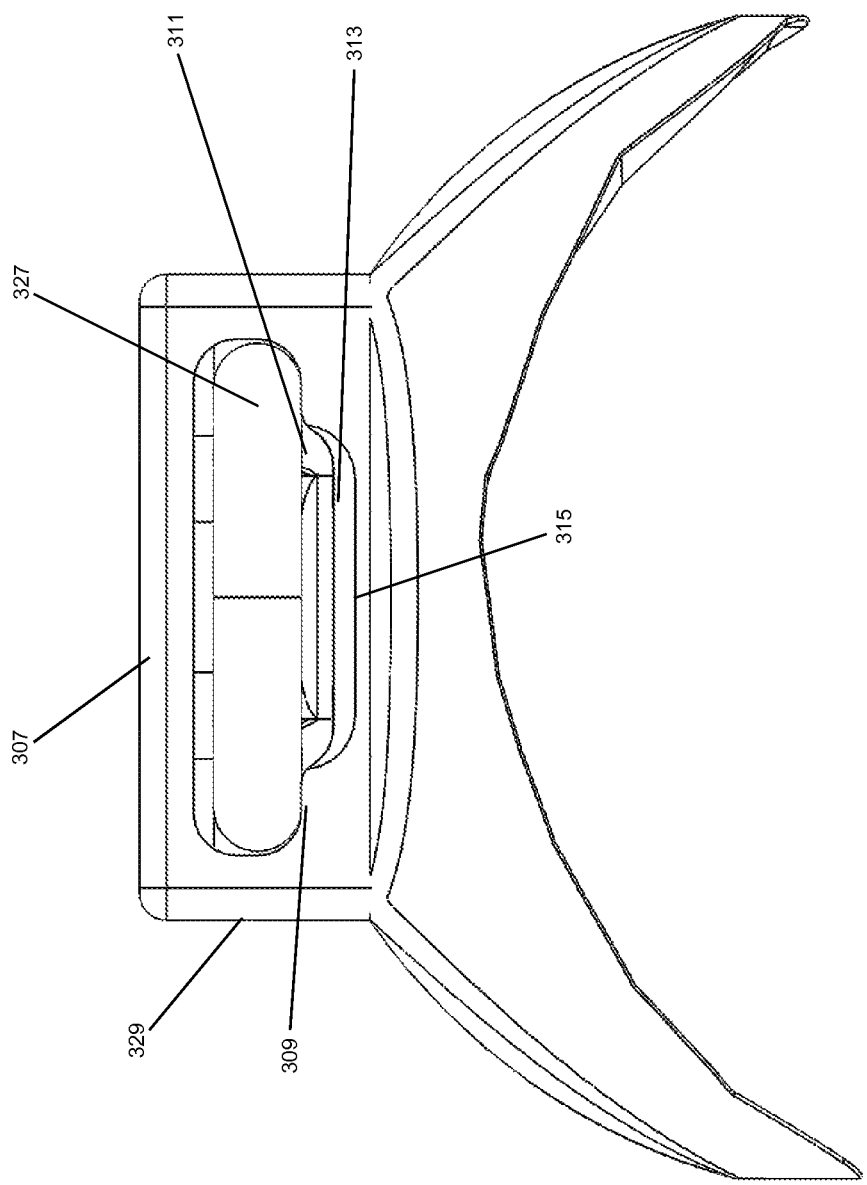
Figure 3E:
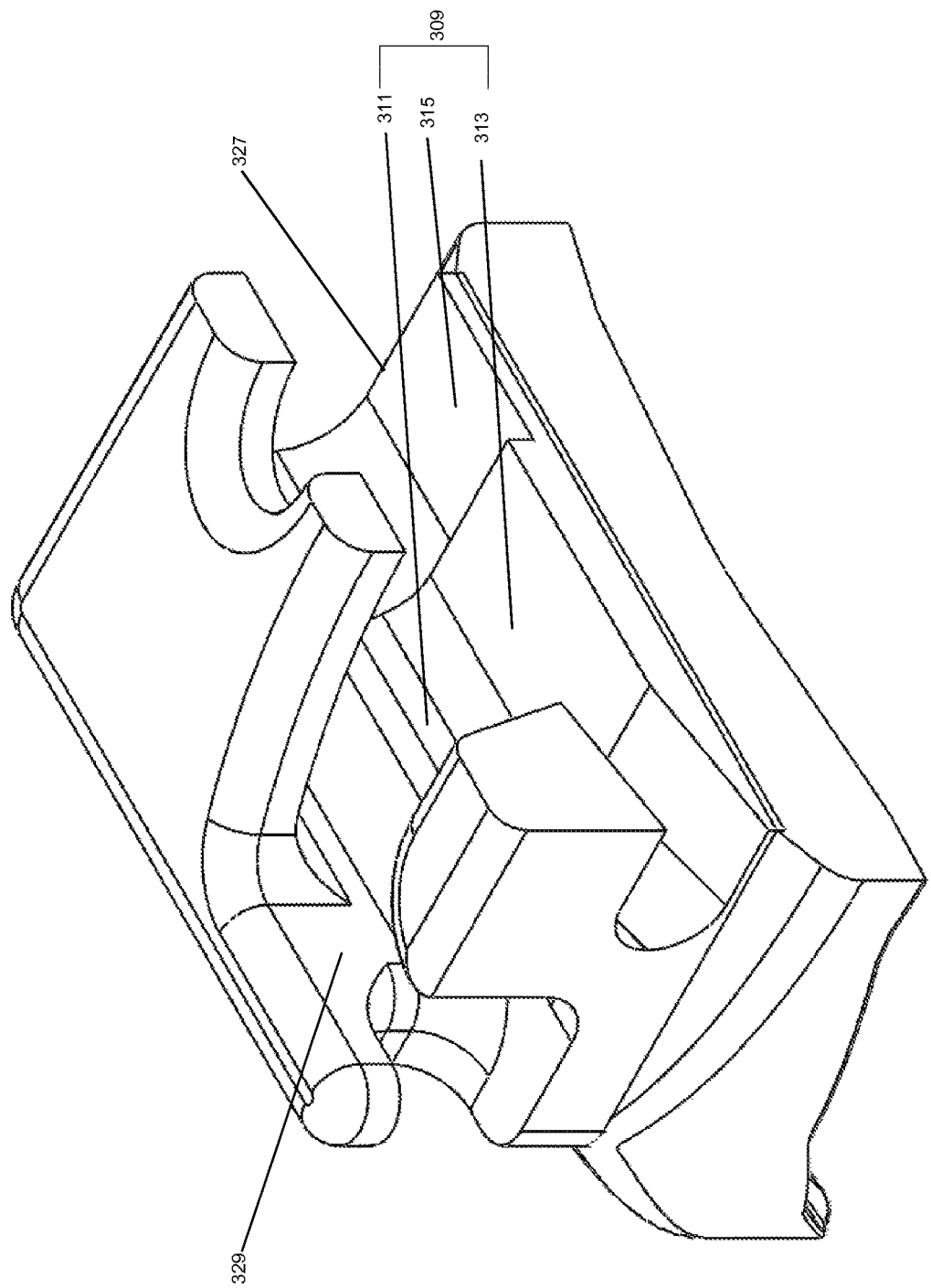
Figure 3F:
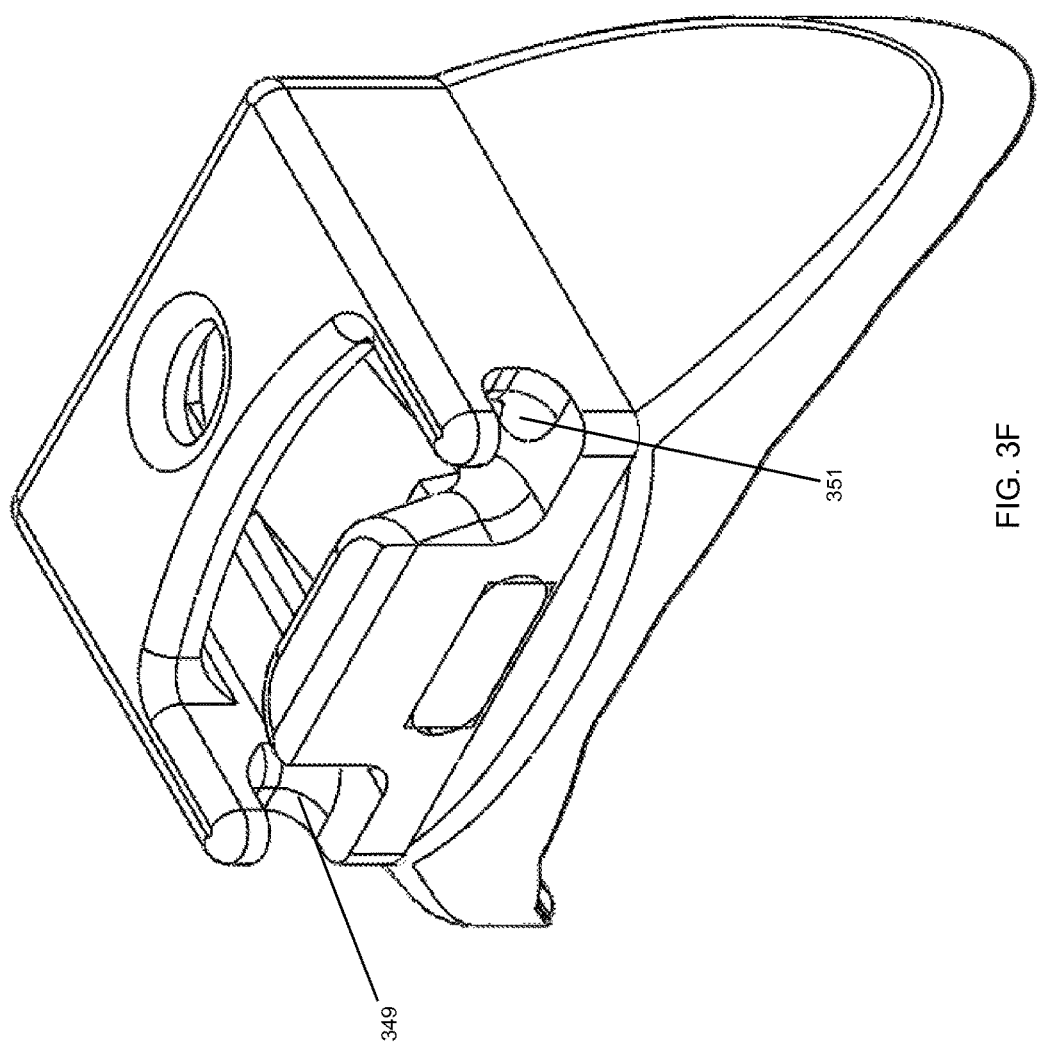

FIGS. 3A-3H illustrate an orthodontic bracket 301 into which a male loop 359 of an archwire 353 may be snap fitted. FIG. 3A illustrates the orthodontic bracket 301 without any male loop; FIG. 3B illustrates the orthodontic bracket after the male loop 359 has been snapped into the orthodontic bracket; FIG. 3C is a cross-section of the view illustrated in FIG. 3B taken along the broken line 3C-3C' in FIG. 3B; FIG. 3D is an occlusal view; FIG. 3E is a cross-section of the view illustrated in FIG. 3A taken along the line 3C-3C' in FIG. 3A with a springboard 337 removed; FIG. 3F illustrates the orthodontic bracket 301 without any male loop; FIG. 3G is a cross-section of the view illustrated in FIG. 3B taken along the broken line 3G/H-3G/H' in FIG. 3B when the distance between a free end 343 of the springboard 337 and a bridge 307 is less than half the diameter of the male loop 359 wire; and FIG. 3H is a cross-section of the view illustrated in FIG. 3B taken along the broken line 3G/H-3G/H' in FIG. 3B when the distance between the free end 343 of the springboard 337 and the bridge 307 is more than the diameter of the male loop 359 wire.

The orthodontic bracket 301 may include an orthodontic bracket body 305, the springboard 337, and a base 303. The orthodontic bracket body 305 may include six sides: the bridge 307 on a non-tooth side, a floor 309 on the base 303, a stop 317 on the gingival side, an opening 327 on the occlusal side, and orthodontic bracket rails 329, one on the mesial side and one on the distal side.

The opening 327 may be on the occlusal side of the orthodontic bracket body 305. The opening 327 may allow access for machining the internal components of the orthodontic bracket body 305.

The stop 317 may be on the gingival side of the orthodontic bracket body 305. The stop 317 may combine with other structures to form an archwire insertion slot 347, a vertical archwire slot 349, and a horizontal archwire slot 351. The stop 317 may serves one or more functions in increasing effective and efficient force transfer of the archwire 353 to the orthodontic bracket 301 to move teeth. Examples of these functions are discussed below. The archwire 353 may be of any type, such as the archwire 101 or 201.

The mesial and distal sides of the orthodontic bracket body 305 may include a vertical portion 331 of the orthodontic bracket rails 329. The vertical portion 331 of the orthodontic bracket rails 329, together with the bridge 307 and the floor 309, may form the vertical archwire slot 349 for receiving a male loop 359. The male loop 359 may be of any type, such as the male loop 107 or 207.

A non-tooth side of the orthodontic bracket body 305 may include the bridge 307 that may connect the mesial and the distal orthodontic bracket rails 329. The bridge 307 may combine with other structures to form the archwire insertion slot 347, the vertical archwire slot 349, and the horizontal archwire slot 351. The bridge 307 may also serve functions in increasing effective and efficient force transfer of the archwire 353 to the orthodontic bracket 301 to move teeth. Examples of these functions are discussed further below.

The tooth-side of the orthodontic bracket body 305 may include the floor 309. The floor 309 may combine with other structures to form the archwire insertion slot 347, the vertical archwire slot 349, and the horizontal archwire slot 351.

The floor 309 may have three levels.

A first floor level 311 may be the portion of the floor 309 level that is closest to the bridge 307. The first floor level 311 may combine with the bridge 307 and the vertical component of the orthodontic bracket rail 329 to form the vertical archwire slot 349. The side bars of the male loop 359 may ride along the first floor level 311 when the archwire 353 is inserted and removed from the orthodontic bracket 301.

A second floor level 313 may be located between the first floor level 311 and a third floor level 315. It may accommodate a springboard body 339 when the springboard 337 is in an active unlocking position, as shown in FIG. 3H.

The third floor level 315 may be the portion of the floor 309 that is closest to the orthodontic bracket base 303. The third floor level 315 may have a depth that is slighter larger than the depth of a springboard protuberance 345 such that it allows the springboard 337 to flex when the archwire 353 is inserted into the orthodontic bracket 301 (locking) or when an instrument is pressed against the springboard body 339 (unlocking).

The bridge 307 may have an access port 357 in the middle to allow an instrument to access and press down on the springboard 337.

The stop 317 may have a springboard slot 321. The springboard slot 321 may be angulated such that a springboard slot outside opening 323 is closer to the base 303 than a springboard slot inside opening 325.

The archwire insertion slot 347 may include a space bordered on three sides by the bridge 307, the floor 309, and the stop 317. The archwire insertion slot 347 may be large enough to allow seating and insertion of the arc of the male loop 359.

The vertical archwire slot 349 may include a space bordered on three sides by the bridge 307, the floor 309, and the vertical portion 331 of the orthodontic bracket rail 329. The vertical archwire slot 349 may be large enough to allow seating of the side bars of the male loop 359.

The horizontal archwire slot 351 may include a space bordered on three sides by an orthodontic bracket leg 335, the floor 309, and the horizontal component 333 of the orthodontic bracket rail 329. The horizontal archwire slot 351 may be large enough to allow seating of the orthodontic bracket legs 335.

The springboard 337 may be a movable member of the orthodontic bracket body 305. It may have a U or rectangular shape with the springboard body 339 that has two parallel sides, a springboard plug 341 that is fixed to the springboard slot 321, and a springboard free end 343. The springboard free end 343 may have the half-disc shaped springboard protuberance 345 facing the floor 309. The springboard 337 may be held at a position such that at the point where the springboard 337 exits the springboard slot 321, the bridge 307 side of the springboard 337 may be slightly closer to the base 303 of the orthodontic bracket than the first floor level 311 is to the base 303 of the orthodontic bracket 301. This may ease snapping and unsnapping the archwire 353 from the orthodontic bracket 301. The occlusal end of the springboard 337 may be closer to the bridge 307 than the gingival end of the springboard 337, such that the space between the springboard free end 343 and the bridge 307 may be less than half the diameter of the archwire 353 when the springboard 337 is in the passive locked position (FIG. 3G). This configuration may provide a locking mechanism to keep the archwire 353 in place when the orthodontic bracket 301 is in the snapped position.

The base 303 may provide more surface area and thus better bonding retention of the orthodontic bracket 301 to the tooth. The base 303 may be larger than the floor 309 of the orthodontic bracket body 305. It may have a tooth side that touches and bonds to the tooth. The tooth side may be custom made to fit to a particular patient's particular tooth, it may be made to fit a certain type of teeth for all patients, or it may be made to fit all teeth indiscriminately. The orthodontic bracket side of the base 303 may be connected to the base side of the floor 309. The outline of the base 303 may be rounded and smooth. The transition between the orthodontic bracket body 305 and the base 303 and between the base 303 and the tooth surface may be gradual and seamless. Alternatively, the base 303 may be omitted and the tooth-side of the floor 309 can be bonded directly to the tooth.

To snap the archwire 353 into the orthodontic bracket 301, the male loop 359 may be seated into the archwire insertion slot 347 and pushed occlusally. The side bars of male loop 359 may be made to slide along the vertical archwire slot 349. As the side bars of male loop 359 slide along the vertical archwire slot 349, the arc of male loop 359 may glide over the springboard body 339 towards the springboard free end 343, causing the springboard body 339 to be depressed from its passive locking position (FIG. 3G) towards the floor 309 into an active unlocking position (FIG. 3H). The springboard body 339 active unlocking position may allow the arc of the male loop 359 to pass through. Once the arc of male loop 359 is pushed off the springboard free end 343, the springboard body 339 may move from the active depressed unlocking position (FIG. 3H) back to the passive locking position (FIG. 3G) to snap the male loop 359 in place. The male loop 359 may remain in the passive locked position (FIG. 3G) as the archwire 353 couples forces to the orthodontic bracket 301 to move the teeth. The archwire 353 may thus be held firmly and rigidly in place by the orthodontic bracket rails 329, the bridge 307, the first floor level 311, the side of the springboard body 339, the side of the stop 317, and the orthodontic bracket legs 335 when it is fully inserted, seated, and snapped in place. This rigid fixation may help ensure the effective and efficient transfer of force between the archwire 353 and the orthodontic bracket 301 to produce predictable orthodontic forces.

Figure 4A:
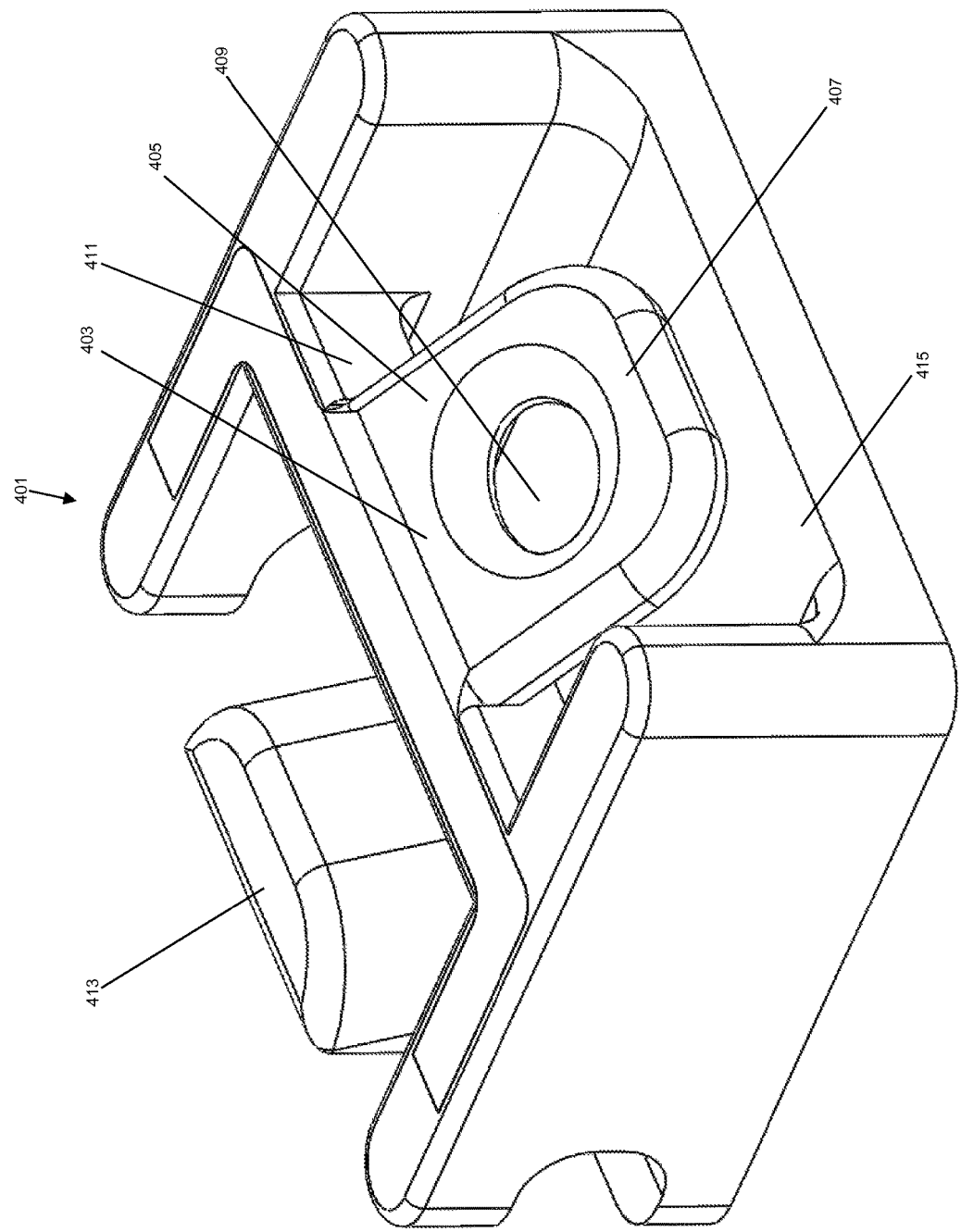
FIGS. 4A-4E illustrate a different configuration of an orthodontic bracket into which a male loop of an archwire may be snap fitted.
Figure 4B:
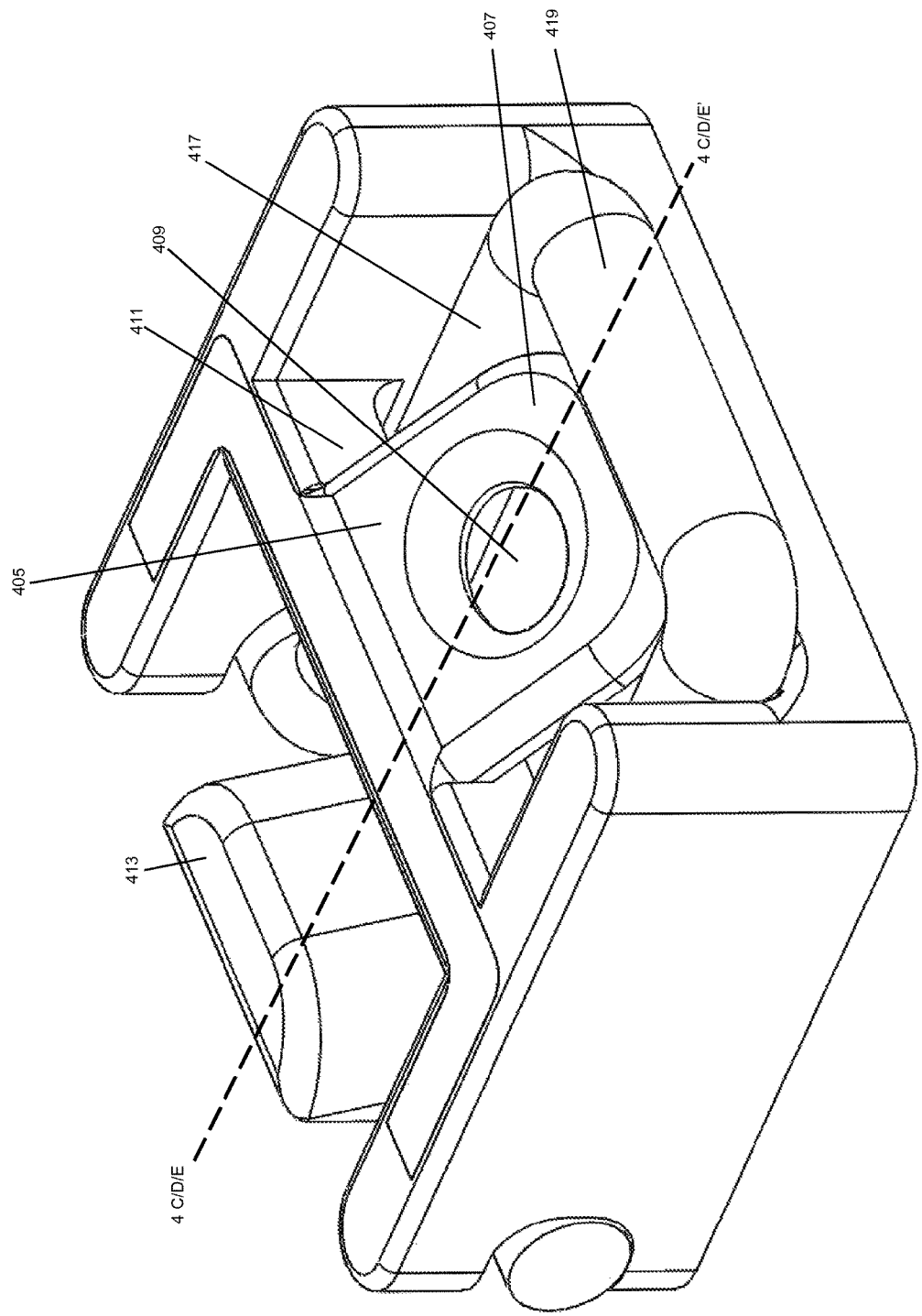
Figure 4C:
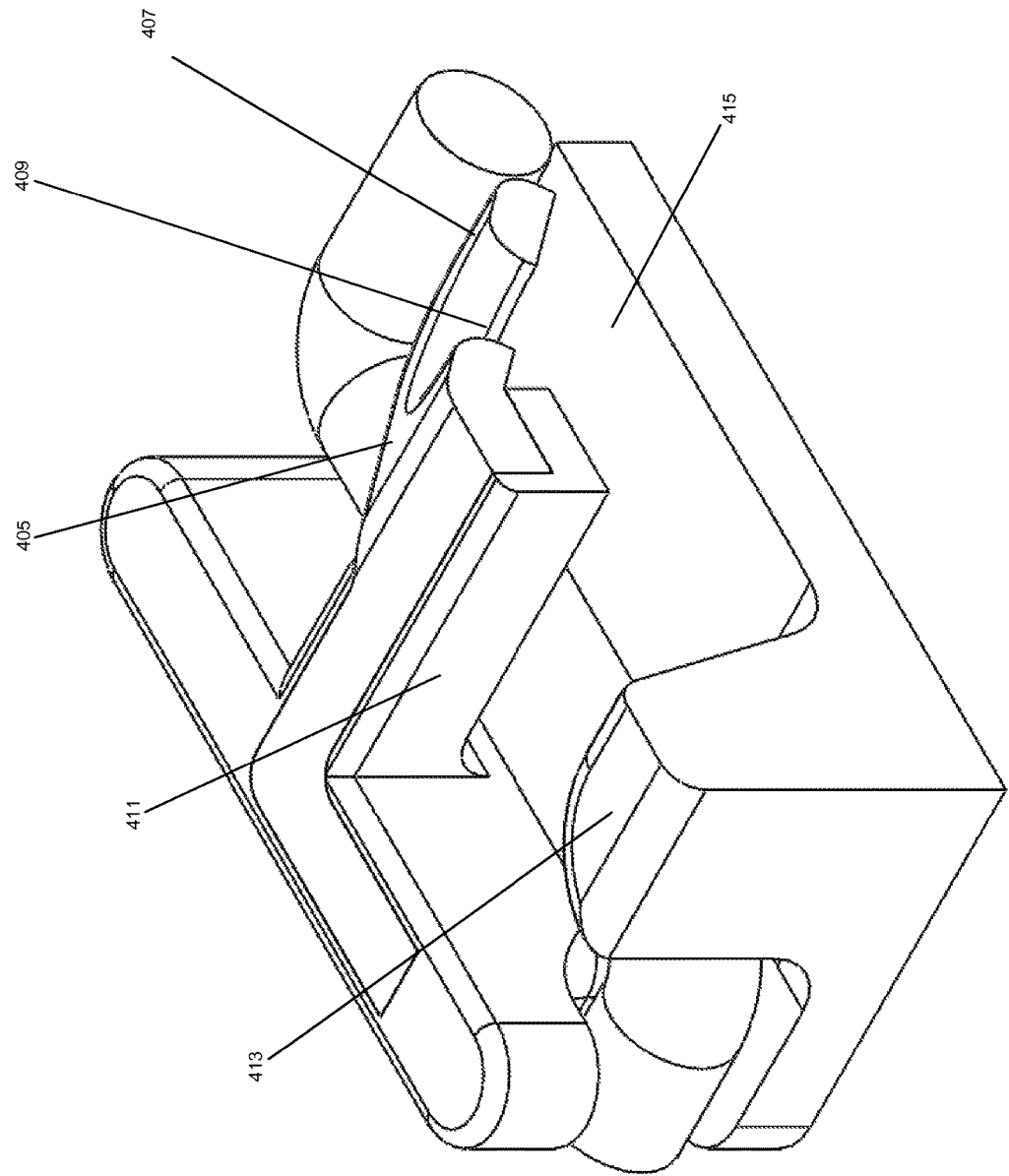
Figure 4D:
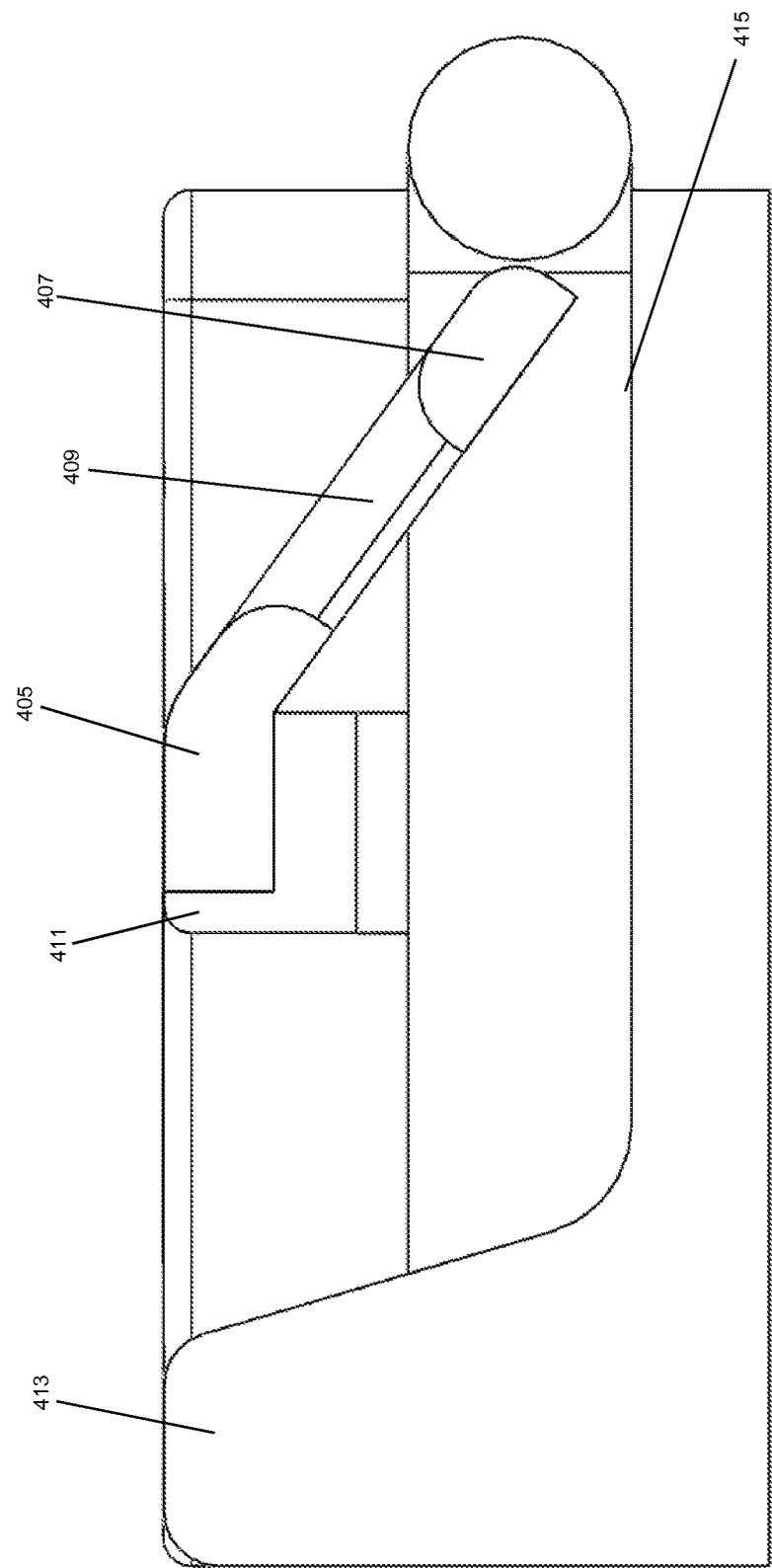
Figure 4E:
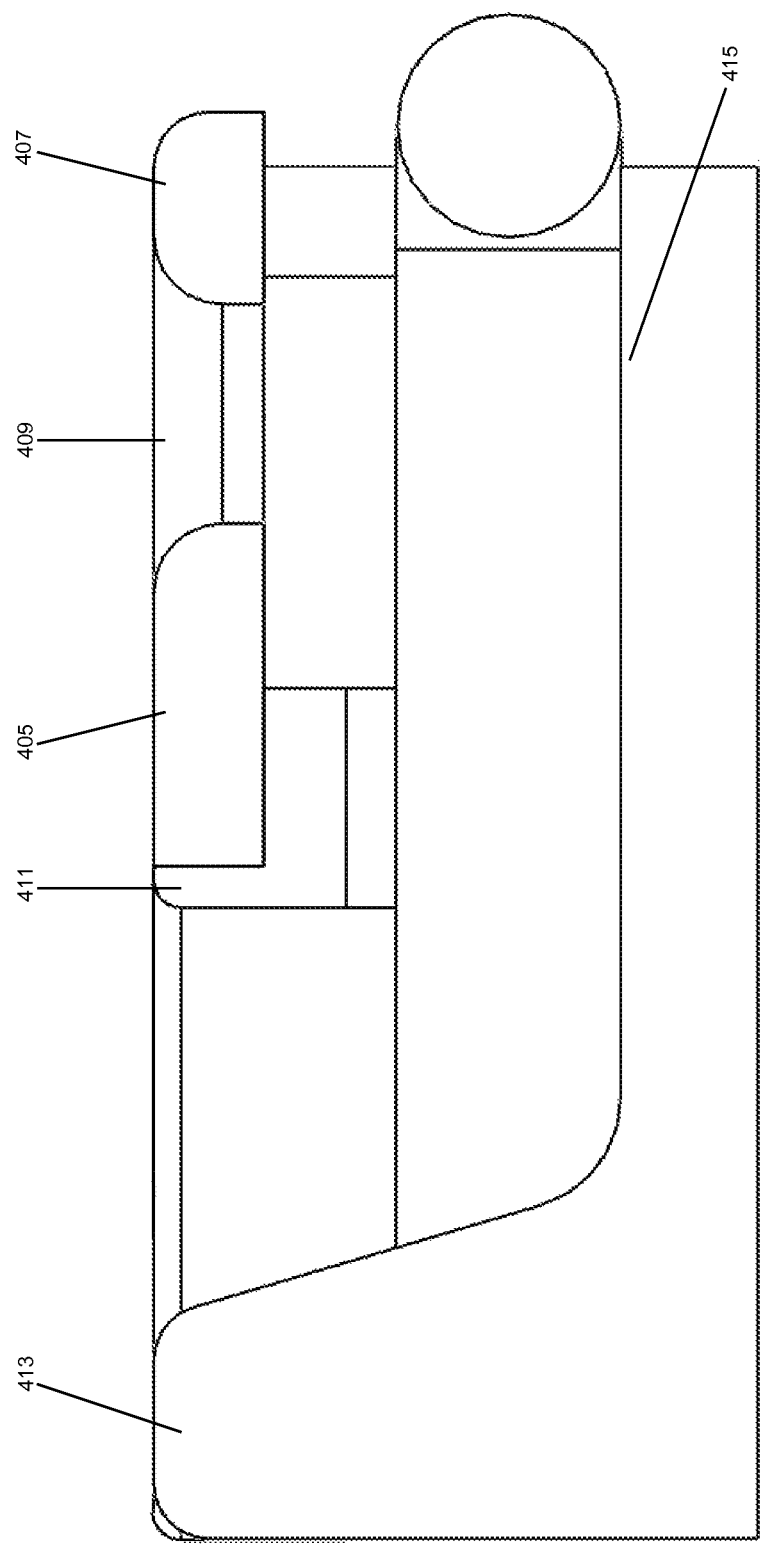

To unsnap the archwire 353 from the orthodontic bracket 301, the springboard body 339 may be depressed with an instrument through the access port 357. The free end 343 of the springboard 337 may then move toward the floor 309 of the orthodontic bracket until the springboard protuberance 345 touches the third floor level 315, thereby clearing the male loop 359 for withdrawal. This is the active unlocking position (FIG. 3H). After the male loop 359 is withdrawn from the orthodontic bracket 301, the springboard may move from the active unlocking position (FIG. 3H) back to the passive locking FIGS. 4A-4E illustrate a different configuration of an orthodontic bracket 401 into which a male loop 419 of an archwire 417 may be snap fitted. FIG. 4A illustrates the orthodontic bracket 401 without any loop; FIG. 4B illustrates the orthodontic bracket 401 after the male loop 419 has been snapped into the orthodontic bracket 401; FIG. 4C is a cross-section of the view in FIG. 4B taken along the broken line 4C/D/E-4C/D/E' in FIG. 4B; FIG. 4D is a cross-section of the view in FIG. 4B taken along the broken line 4C/D/E-4C/D/E' in FIG. 4B when the distance between a free end 407 of a springboard 403 and a floor 415 is less than half the diameter of the male loop 419; and FIG. 4E is a cross-section of the view in FIG. 4B taken along the broken line 4C/D/E-4C/D/E' in FIG. 4B when the distance between the free end 407 of the springboard 403 and the floor 415 is more than the diameter of the male loop 419.

The components in FIGS. 4A-4E may be the same as the corresponding components in FIGS. 3A-3H, except as now noted.

One difference between the embodiment shown in FIGS. 4A-4E and in FIGS. 3A-3H may be how the springboard 403 functions to snap fit the archwire 417 (which may be of any type, such as the archwire 101 or 202) into place. The springboard 403 may be a movable member that is connected to a bridge 411 at an angle less than 180 degrees. The springboard 403 may have an access port 409 in the middle to allow an instrument to access and lift the springboard body 405 away from the floor 415. When the springboard 403 is in a passive locked position (FIG. 4D), the distance between the free end 407 of the springboard 403 and the floor 415 may be less than half of the diameter of the archwire 417. When an instrument is inserted through the access port 409 to lift the springboard body 405 away from the floor 415, the point at which the distance between the free end 407 of the springboard 403 and the floor 415 may be more than the diameter of the archwire 417 is an active unlocking position (FIG. 4E).

The bridge 411 may be narrower in the occlusal-gingival direction than the bridge 307. The bridge 411 may not contain the access port 409.

A stop 413 may not contain the springboard opening 319, the springboard slot 321, the springboard slot outside opening 323, or the springboard slot inside opening 325.

The floor 415 may have only one level.

To snap the archwire 417 into the orthodontic bracket 401, the operator may take the same steps as described in connection with FIGS. 3A-3H. The snap fitting mechanism may differ in that, as the side bars of a male loop 419 (which may be of any type, such as the male loop 107 or 207) slides along a vertical archwire slot 421, the arc of the male loop 419 may glide under the springboard body 405 towards the free end 407 of the springboard, causing the springboard body 405 to be lifted from its passive locking position (FIG. 4D) away from the floor 415 into an active unlocking position (FIG. 4E). Once the arc of the male loop 419 is pushed off the free end 407 of the springboard 405, the springboard body 405 may move from the lifted active unlocking position (FIG. 4E) back to the passive locking position (FIG. 4D) to snap the male loop 419 in place.

To unsnap the archwire 417, the free end 407 of the springboard 403 may move from the passive locking position (FIG. 4D) to the active unlocking position (FIG. 4E). This may be accomplished by lifting the springboard body 405 with an instrument through the access port 409 so that the free end 407 of the springboard 403 moves towards the bridge 411 of the orthodontic bracket 401 until the springboard 403 is in the active unlocking position (FIG. 4E). After the male loop 419 is withdrawn from the orthodontic bracket 401, the springboard 403 may move from the active unlocking position (FIG. 4E) back to the passive locking position (FIG. 4D).

Figure 5A:
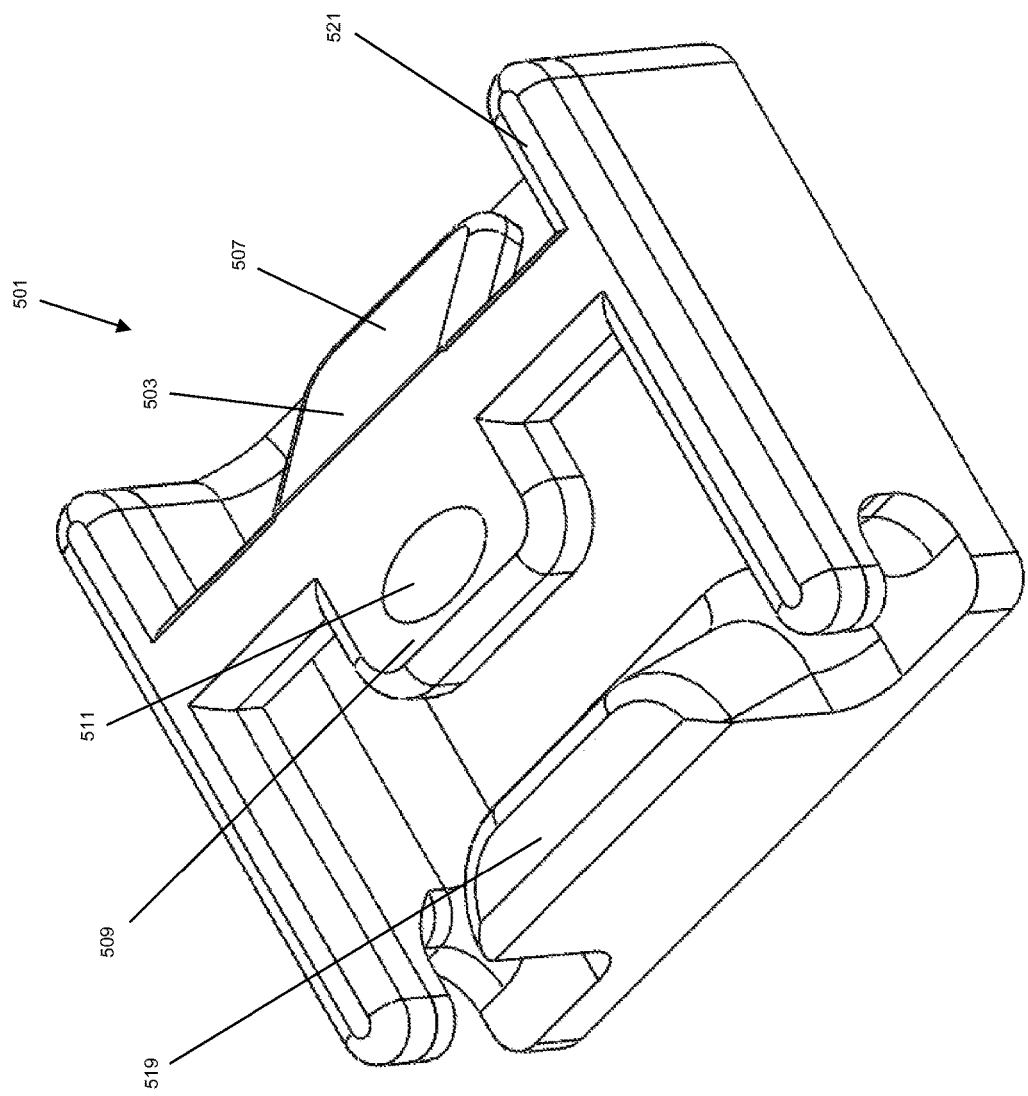
FIGS. 5A-5E illustrate a different configuration of an orthodontic bracket into which a male loop of an archwire may be snap fitted.
Figure 5B:
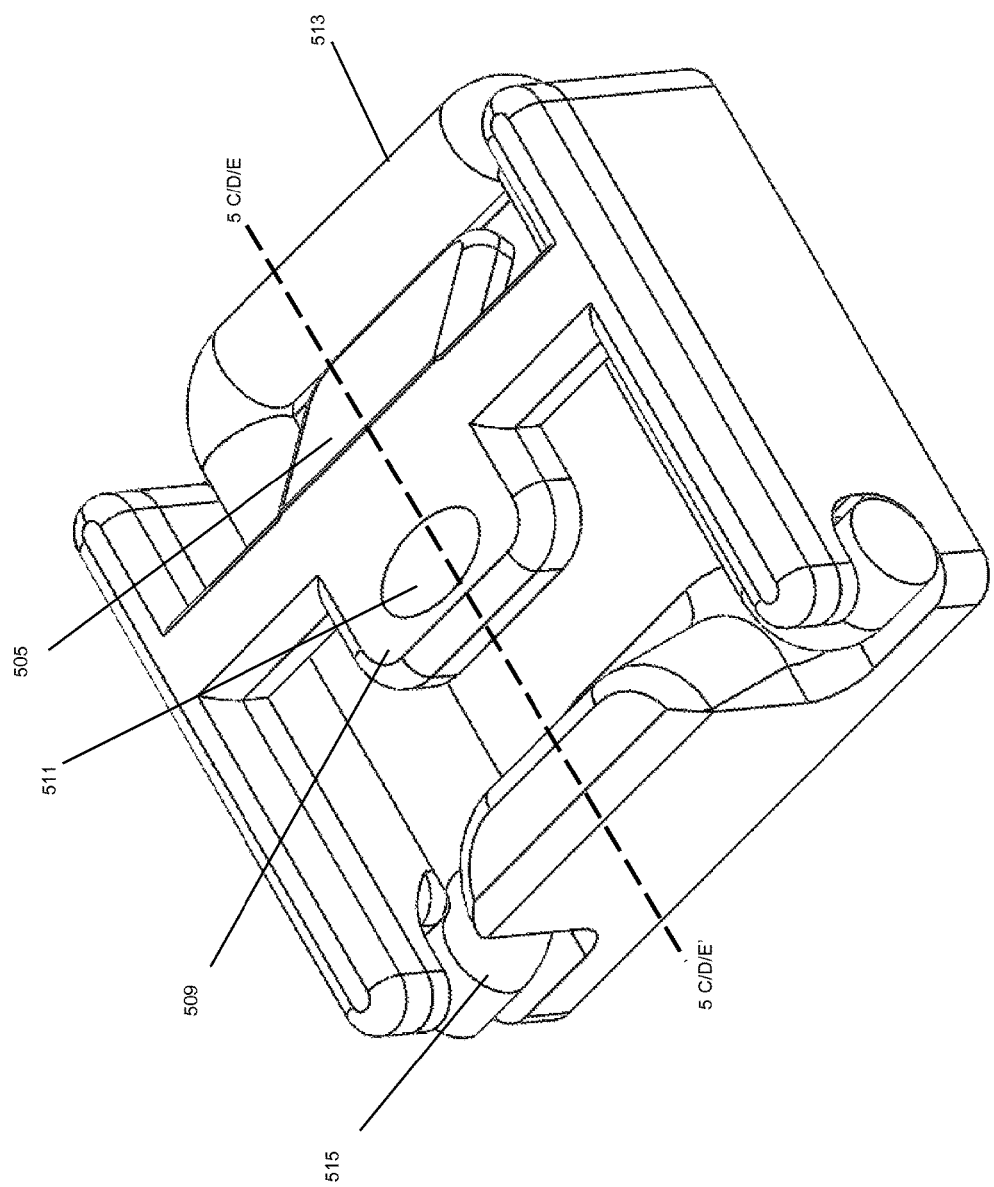
Figure 5C:
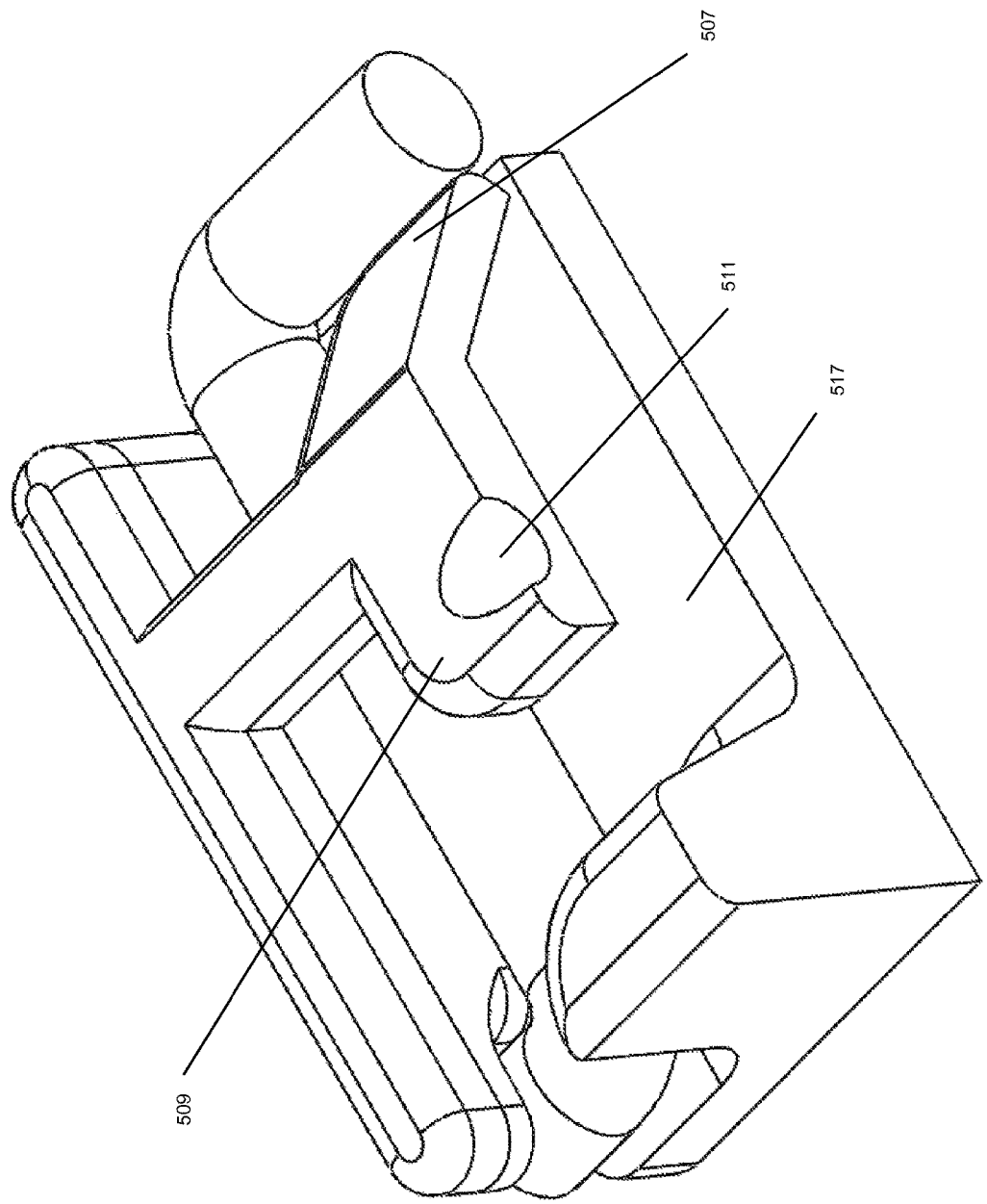
Figure 5D:
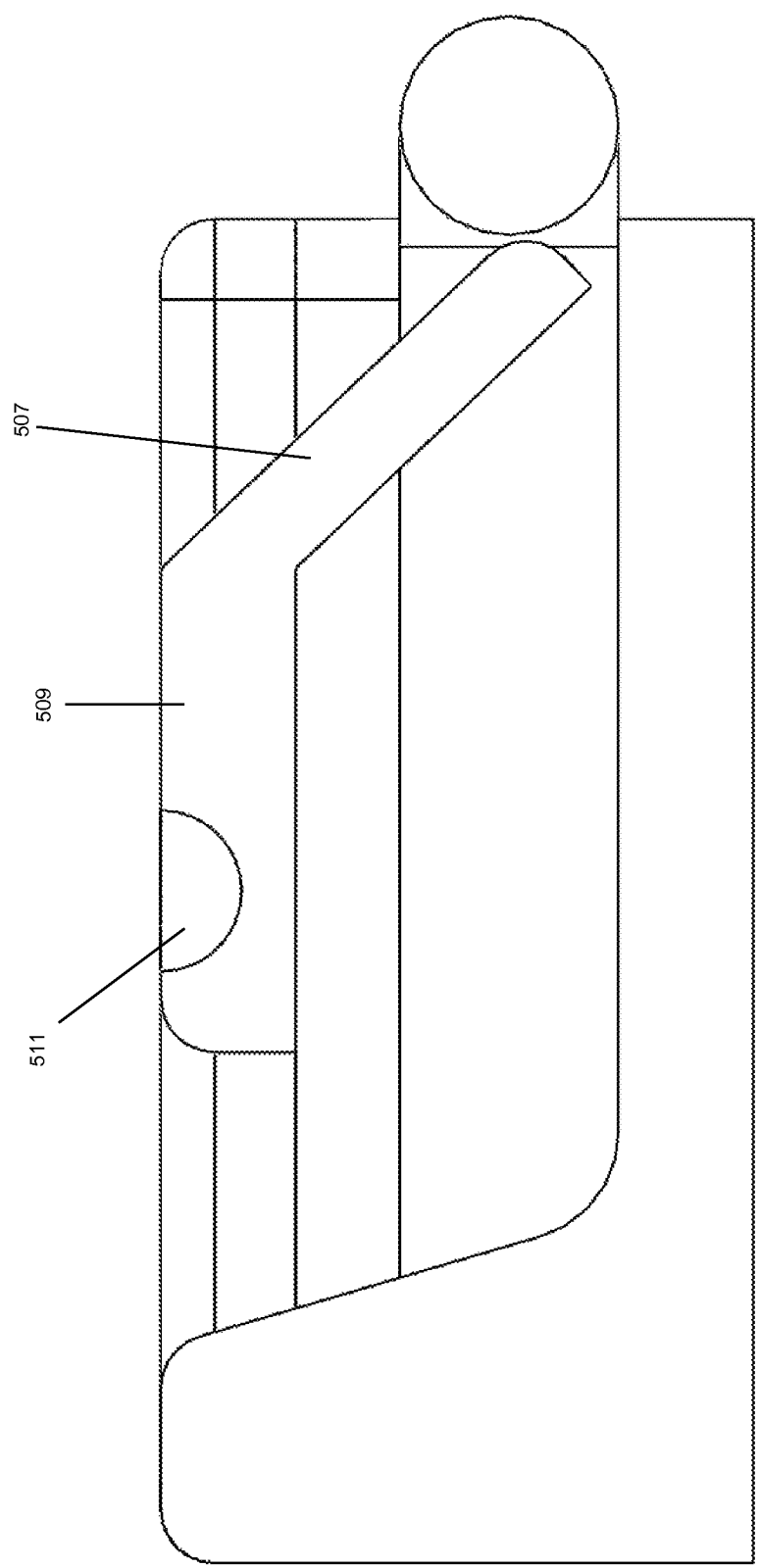
Figure 5E:
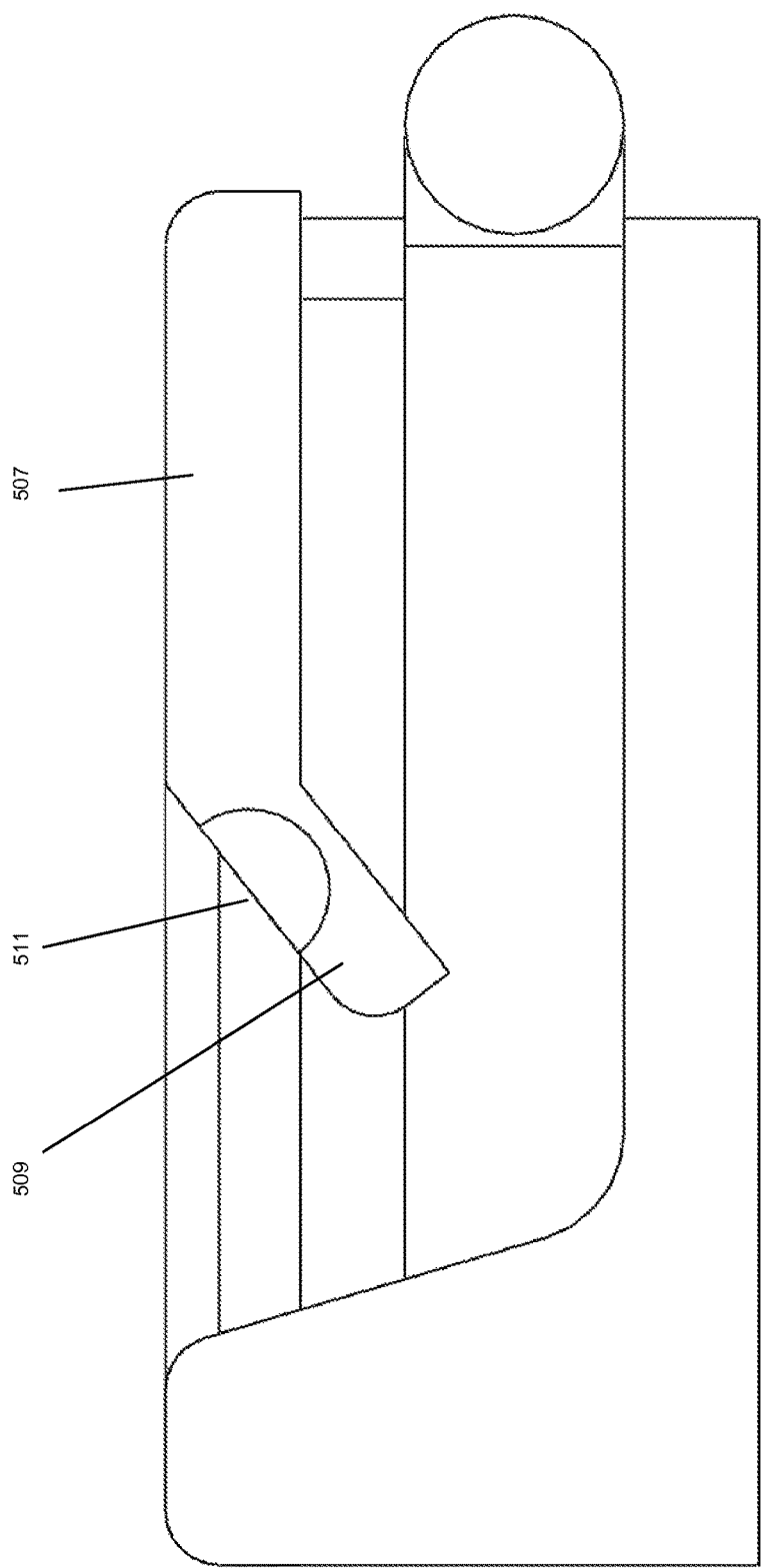

FIGS. 5A-5E illustrate a different configuration of an orthodontic bracket 501 into which a male loop 513 of an archwire 515 may be snap fitted. FIG. 5A illustrates the orthodontic bracket 501 without any male loop; FIG. 5B illustrates the orthodontic bracket 501 after the male loop 513 has been snapped into the orthodontic bracket; FIG. 5C is a cross-section of the view in FIG. 5B taken along the broken line 5C/D/E-5C/D/E' in FIG. 5B; FIG. 5D is a cross-section of the view in FIG. 5B taken along the broken line 5C/D/E-5C/D/E' in FIG. 5B when the distance between a free end 507 of a springboard 503 and a floor 517 is less than the half the diameter of the male loop 513; and FIG. 5E is a cross-section of the view in FIG. 5B taken along the broken line 5C/D/E-5C/D/E' in FIG. 5B when the distance between the free end 507 of the springboard 503 and the floor 517 is more than the diameter of the male loop 513.

The components in FIGS. 5A-5E may be the same as the corresponding components in FIGS. 4A-4E, except as now noted.

One functional difference between the embodiment shown in FIGS. 5A-5E and in FIGS. 4A-4E may be how the operator unsnaps the archwire 515 from the orthodontic bracket 501.

The springboard 503 may have a springboard extension 509 that extends towards a stop 519. The springboard extension 509 may be along a plane that is parallel with orthodontic bracket rails 521. The springboard extension 509 may include a depression groove 511 that allows an instrument to press down and depress the springboard extension 509 towards the floor. There may not be any access port.

To snap the archwire 515 into the orthodontic bracket 501, the same steps may be taken as discussed above in connection with FIGS. 4A-4E.

To unsnap the archwire 515 from the orthodontic bracket 501, the free end 507 of the springboard 503 may be moved from a passive locking position to an active unlocking position. This may be accomplished by depressing an instrument against the depression groove 511, causing the springboard extension 509 to depress towards the floor 517. As the springboard extension 509 depresses towards the floor 517, the free end 507 may be concurrently lifted away from the floor 517 until the springboard 503 is in the active unlocking position. After the male loop 513 is withdrawn from the orthodontic bracket 501, the springboard 503 may move from the active unlocking position (FIG. 5E) back to the passive locking position (FIG. 5D).

Figure 6A:
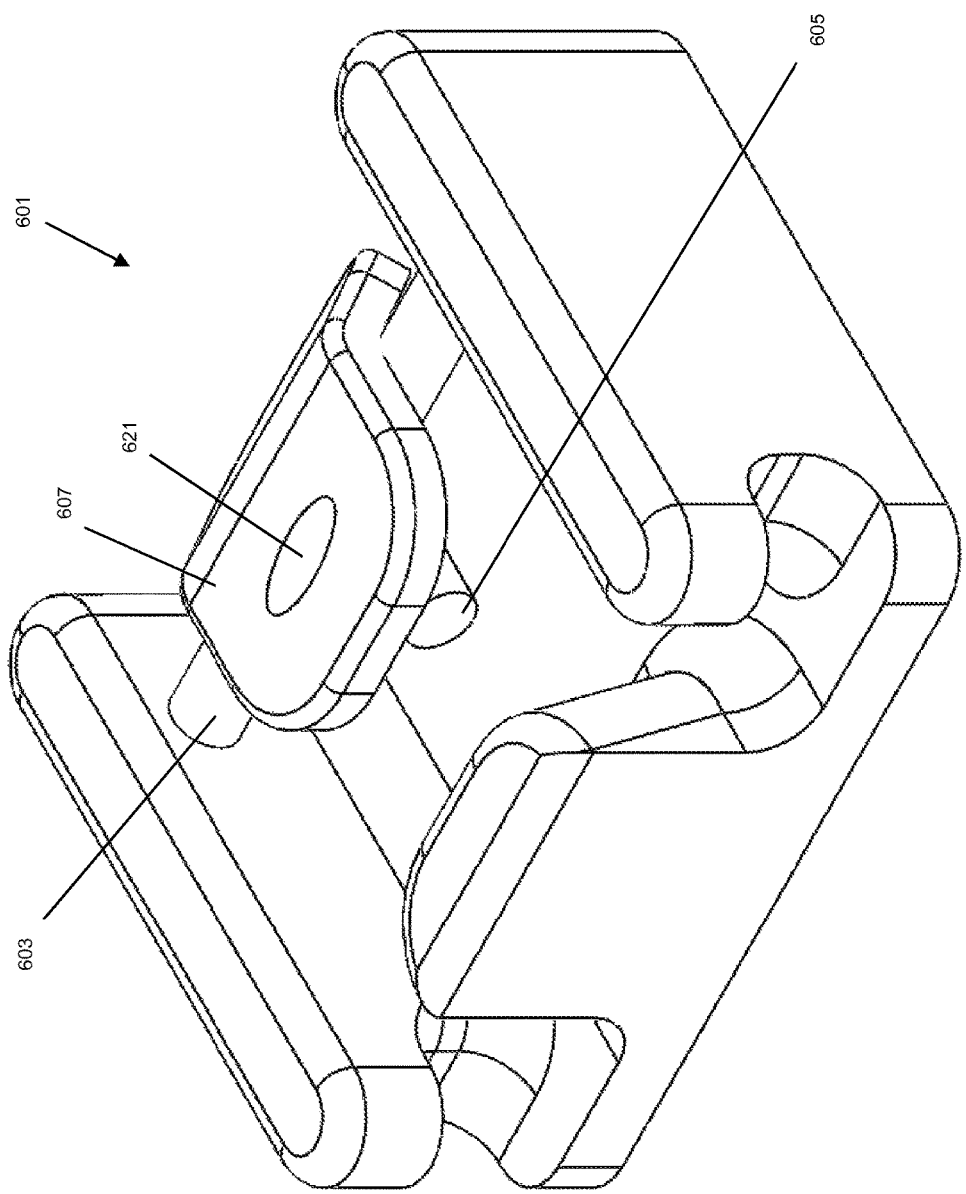
Figure 6B:
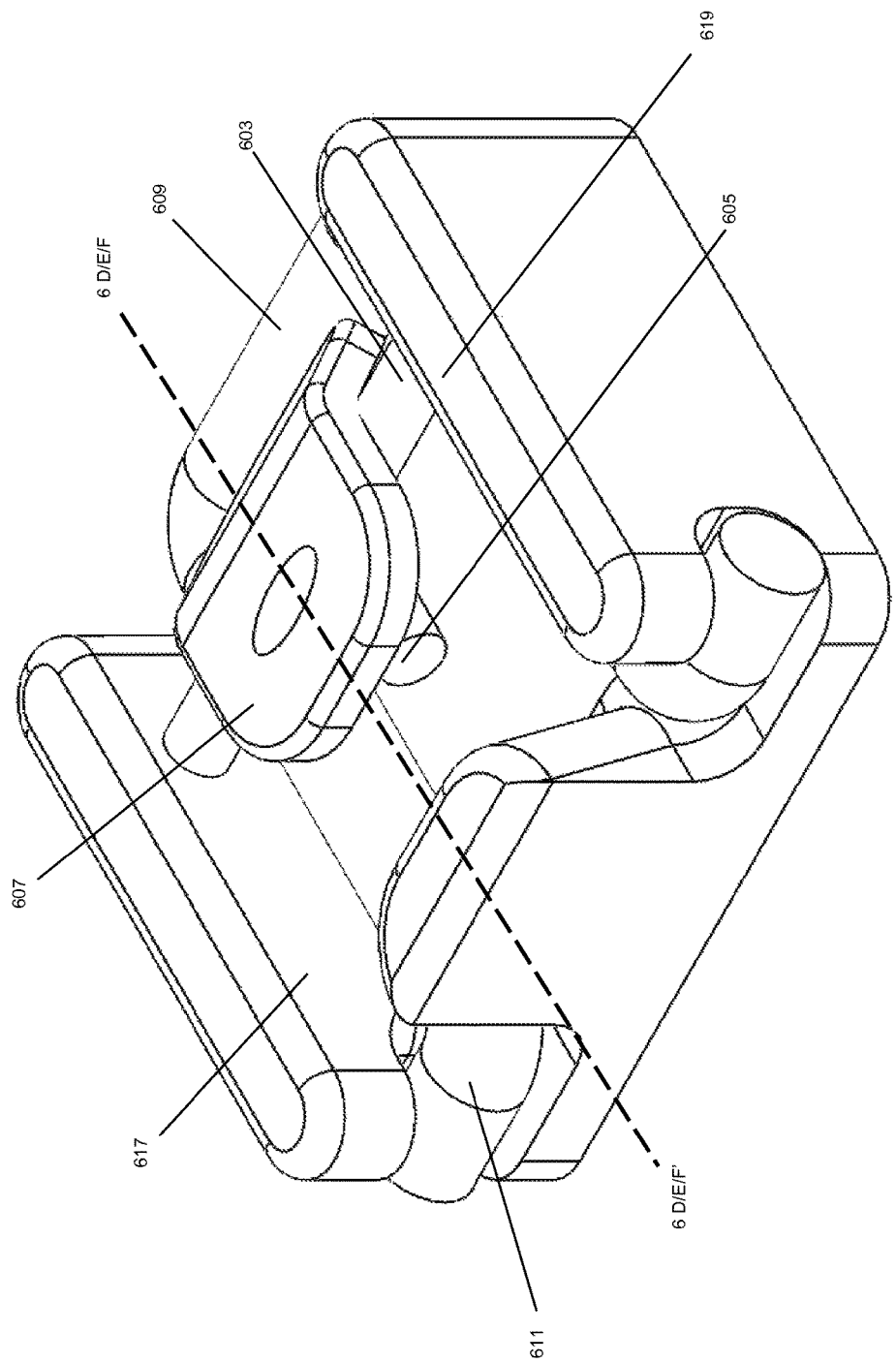
Figure 6C:
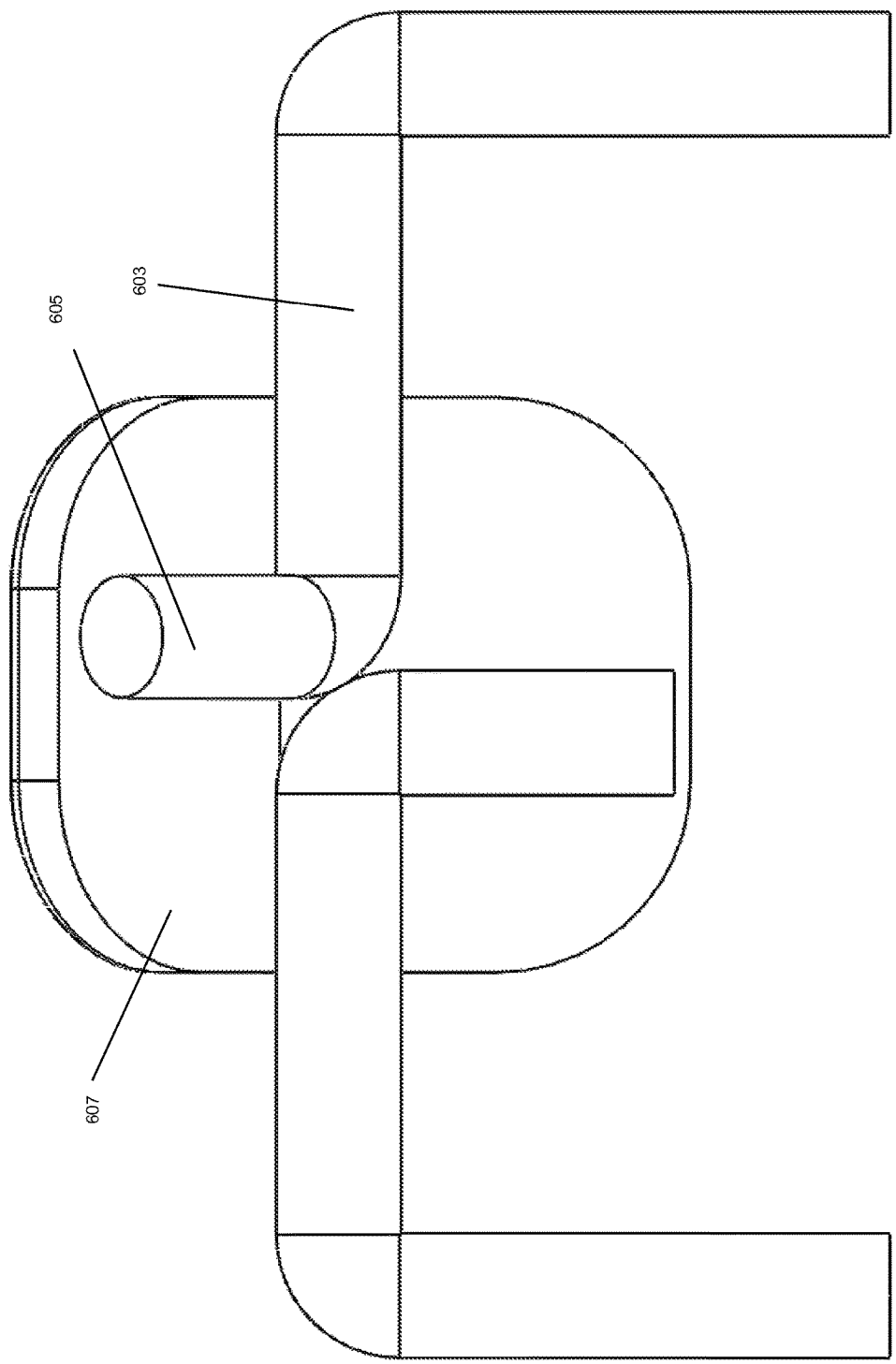
Figure 6E:
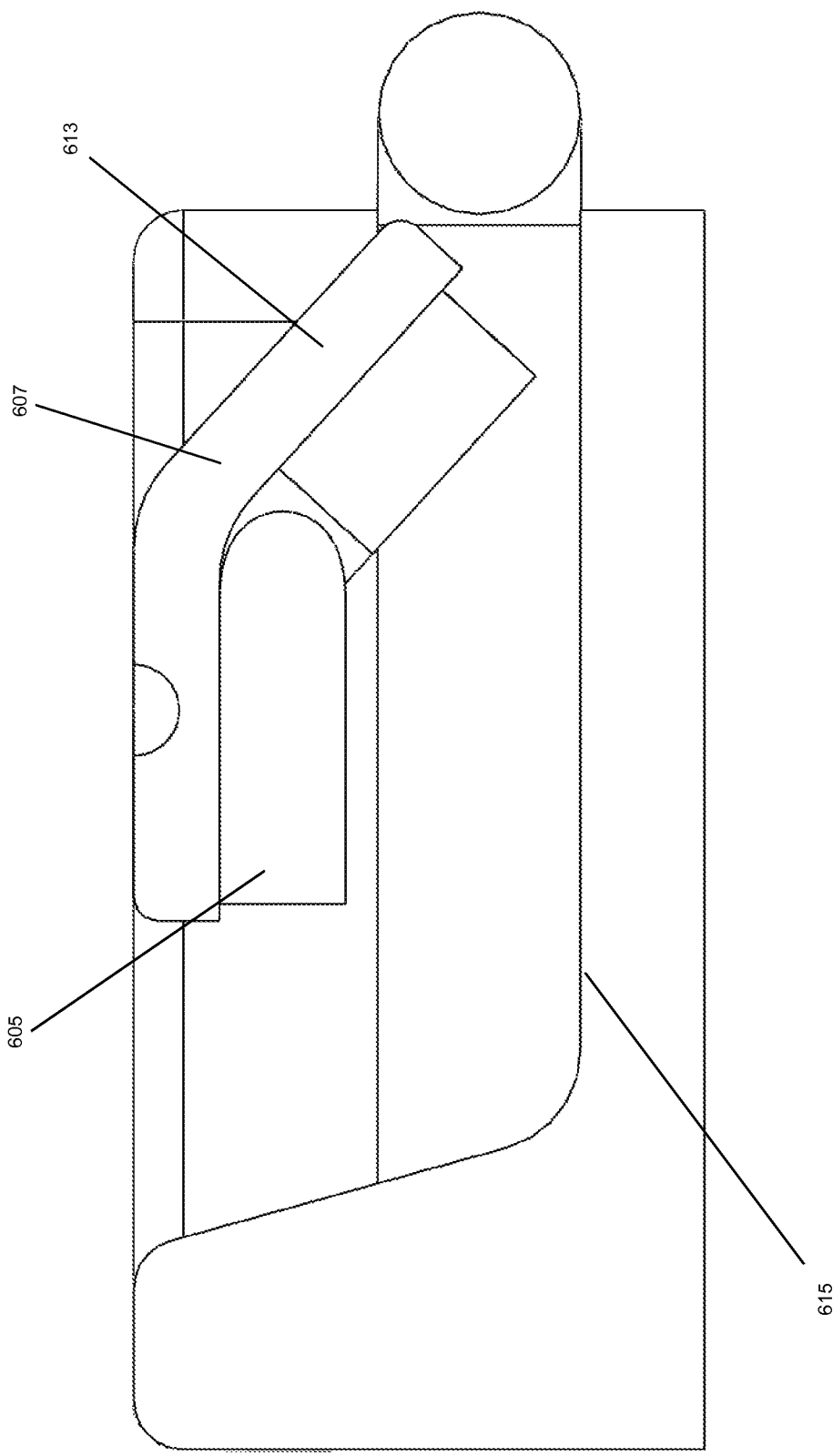
Figure 6F:
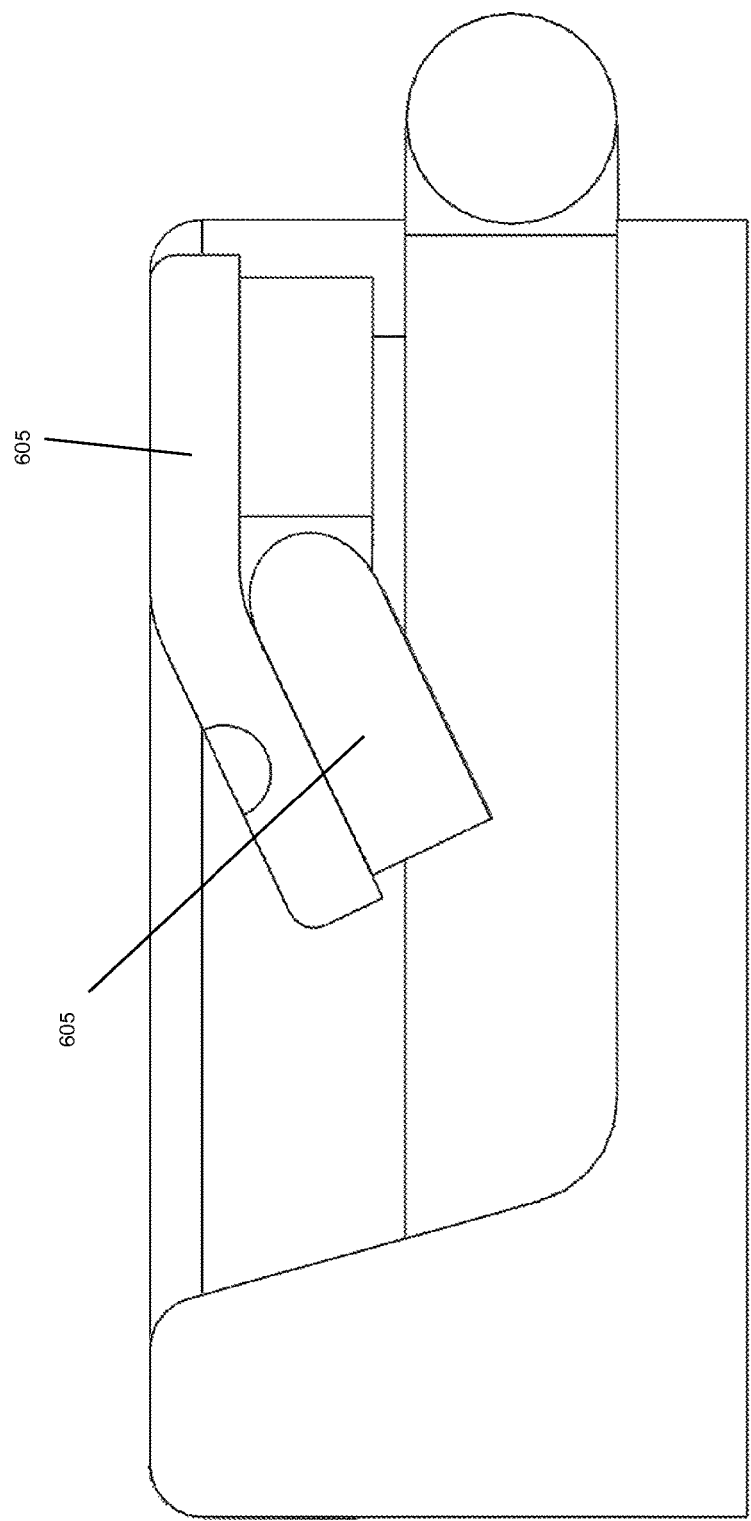

FIGS. 6A-6F illustrate a different configuration of an orthodontic bracket 601 into which a male loop 609 of an archwire 611 may be snap fitted. FIG. 6A illustrates the orthodontic bracket 601 without any male loop; FIG. 6B illustrates the orthodontic bracket 601 after the male loop 609 has been snapped into the orthodontic bracket 601; FIG. 6C is a bottom view of a bridge 603 and springboard 607 in FIG. 6B; FIG. 6D is a cross section of the view in FIG. 6B taken along the broken line 6D/E/F-6D/E/F' in FIG. 6B; FIG. 6E is a cross-section of the view in FIG. 6B taken along the broken line 6D/E/F-6D/E/F' in FIG. 6B when the distance between a free end 613 of the springboard 607 and a floor 615 is less than the half the diameter of the male loop 609 wire; and FIG. 6F is a cross-section of the view in FIG. 6B taken along the broken line 6D/E/F-6D/E/F' in FIG. 6B when the distance between the free end 613 of the springboard 607 and the floor 615 is more than the diameter of the male loop 609.

The components in FIGS. 6A-5F may be the same as the corresponding components in FIGS. 5A-5E, except as now noted.

The bridge 603 may be formed by an orthodontic bracket wire extension 605 that extends from the mesial orthodontic bracket rail 617 and the orthodontic bracket wire extension 605 that extends from the distal orthodontic bracket rail 619. Both orthodontic bracket wire extensions 605 may extend and meet at the center of the orthodontic bracket where one orthodontic bracket wire extension 605 may take a 90 degree turn and extend towards the occlusal end of the orthodontic bracket 601 and the other orthodontic bracket wire extension 605 may take a 90 degree turn and extend towards the gingival end of the orthodontic bracket 601. These orthodontic bracket wire extensions 605 may be movable members such that when the springboard 607 is attached to the orthodontic bracket wire extension 605 and a depression groove 621 is depressed towards the floor 615, the free end 613 of the springboard 607 may move from a passive locking position (FIG. 6E) to an active unlocking position (FIG. 6F).

The springboard 607 may be a separate piece that is attached to the bridge 603 through bonding, welding, or any other technique.

To snap and unsnap the male loop 609 into the orthodontic bracket 601, the same steps may be taken as described above in connection with FIGS. 5A-5E.

Figure 7A:
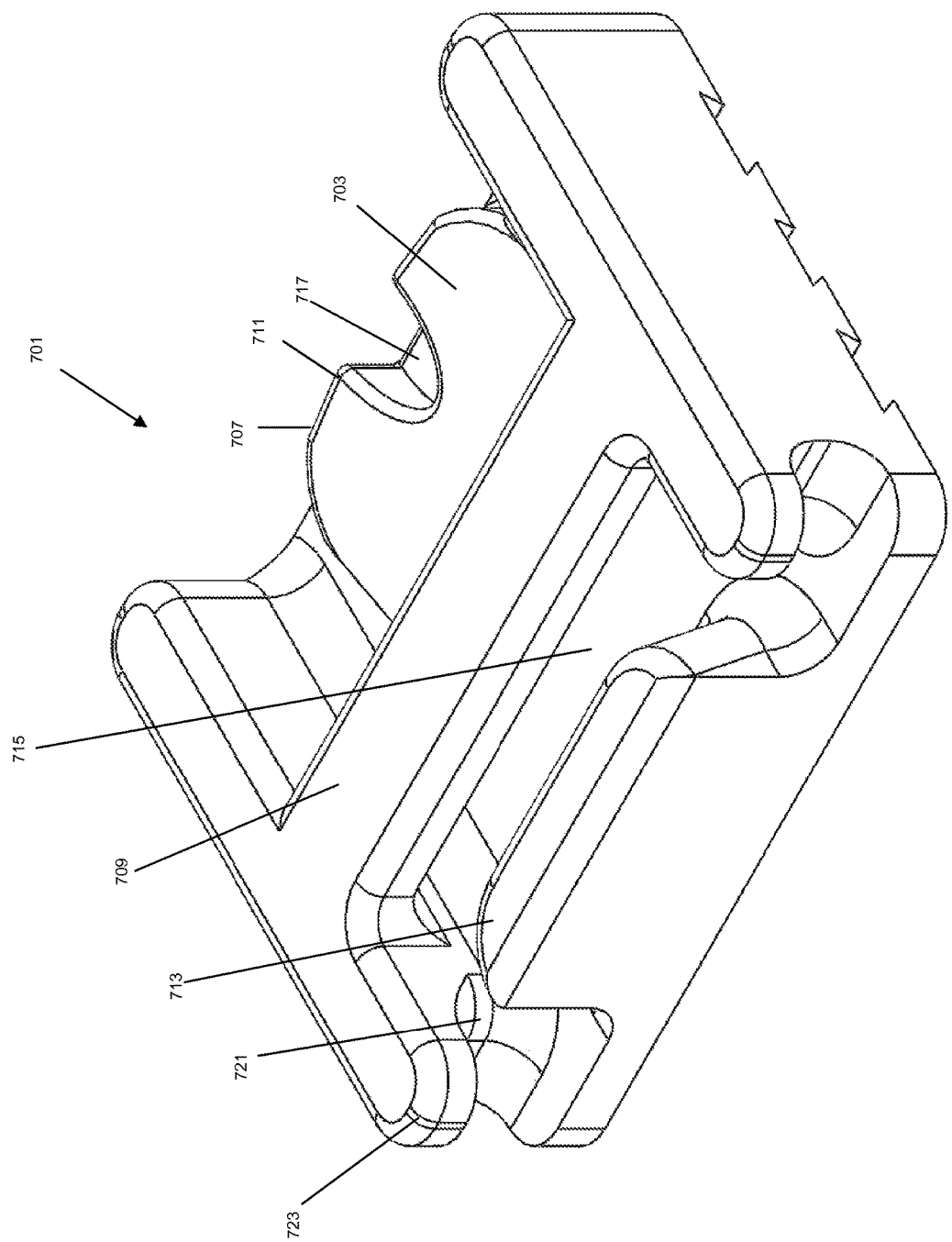
FIGS. 7A-7F illustrate a different configuration of an orthodontic bracket into which a male loop of an archwire may be snap fitted.
Figure 7B:
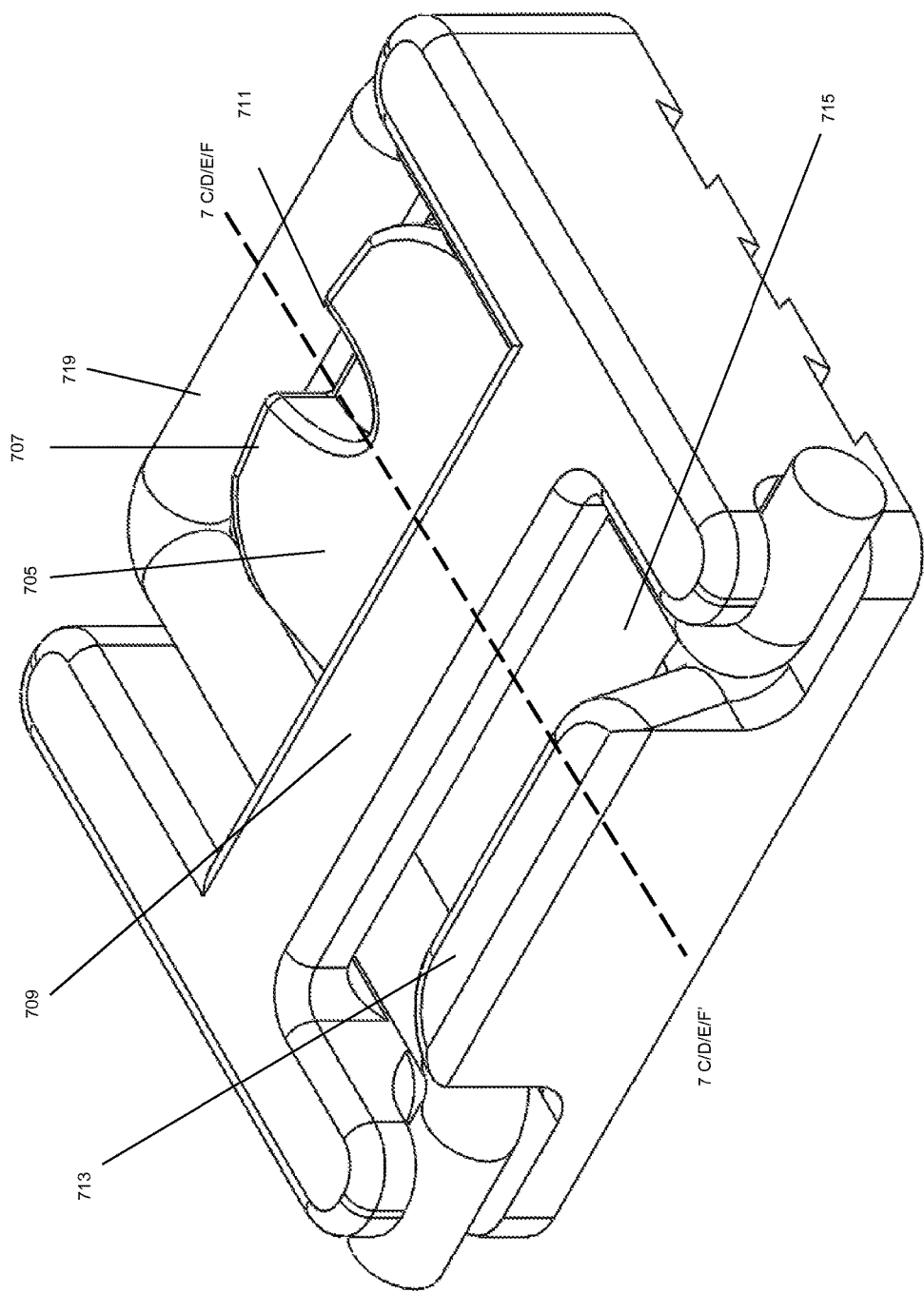
Figure 7C:
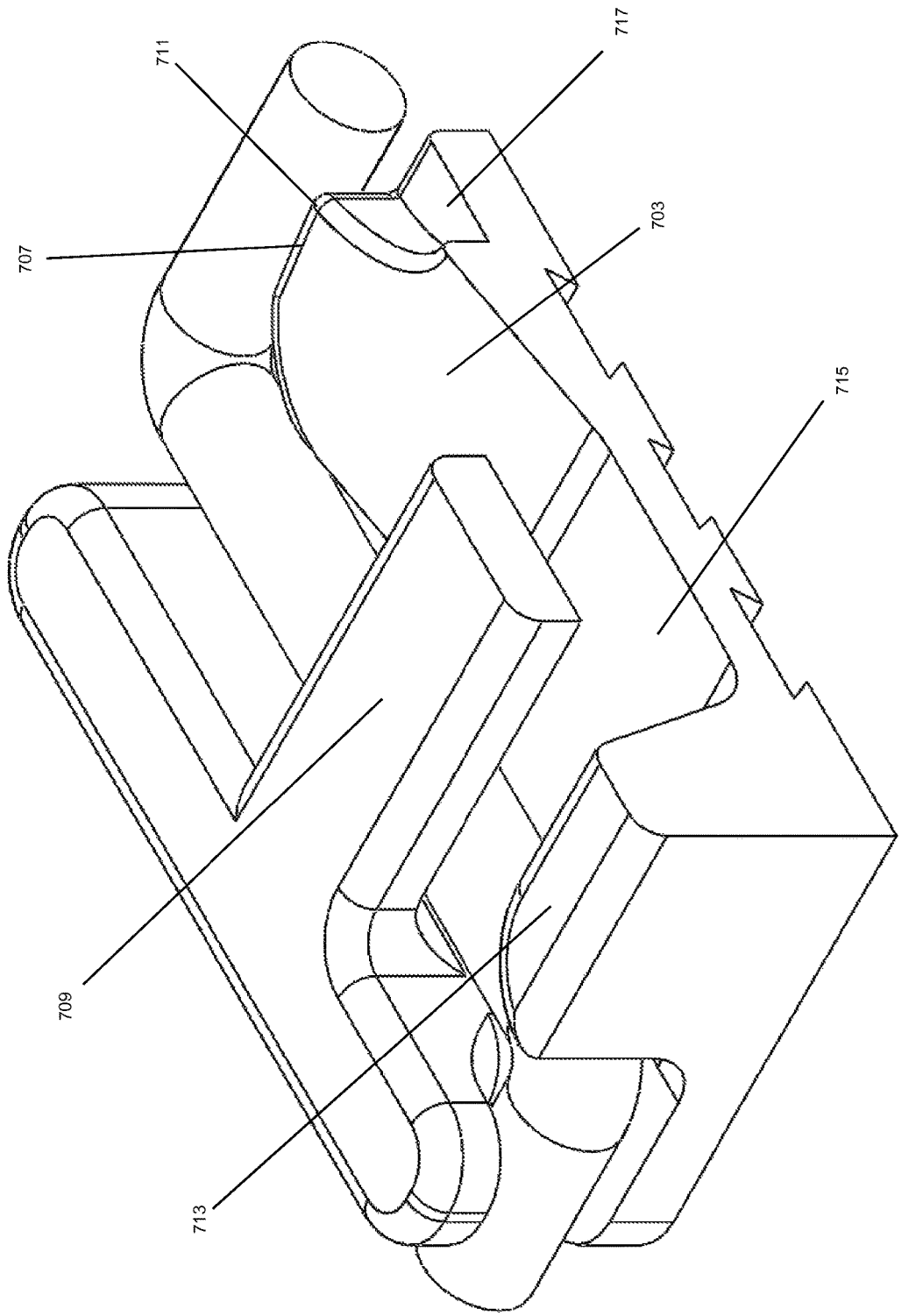
Figure 7D:
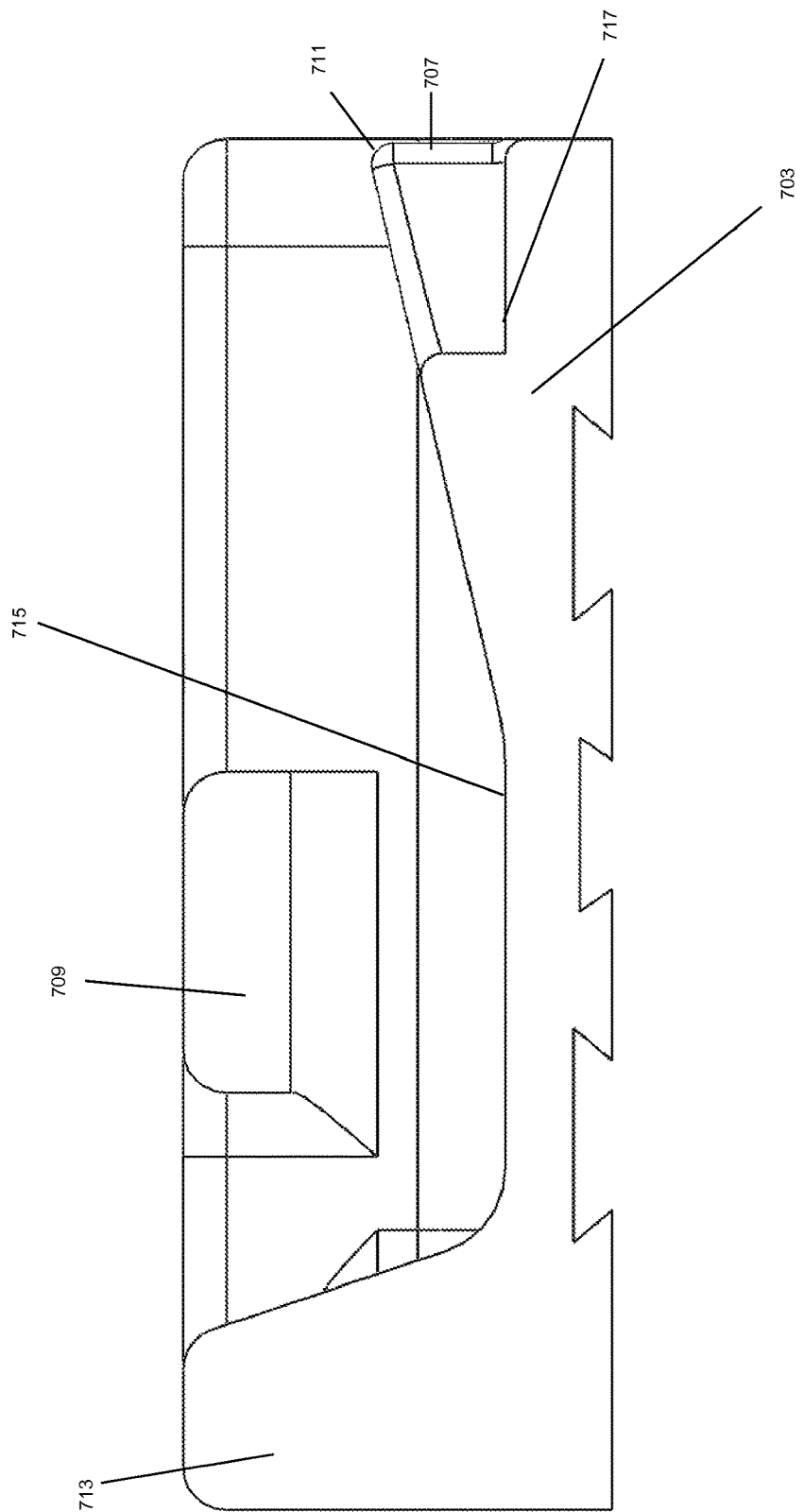
Figure 7E:
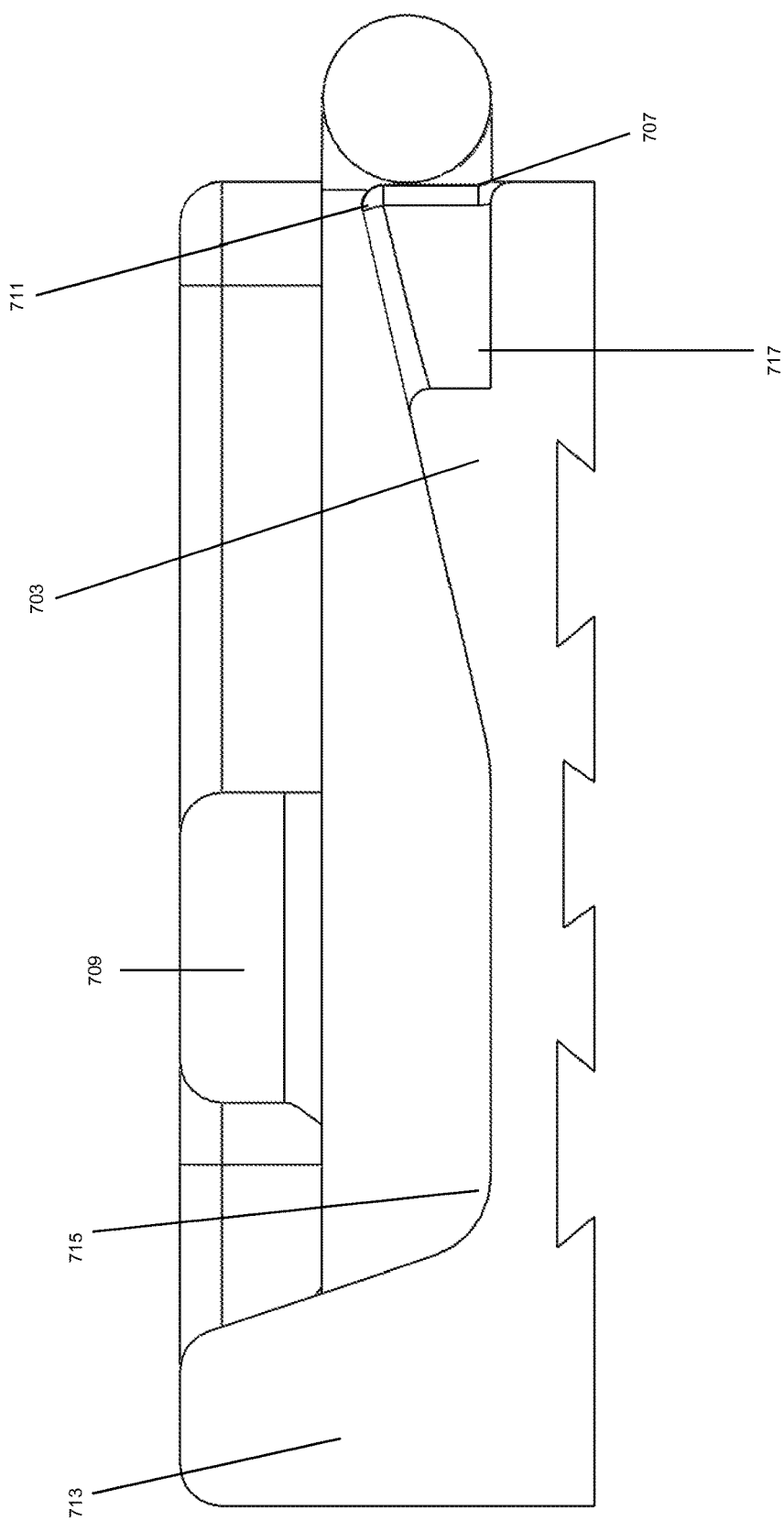
Figure 7F:
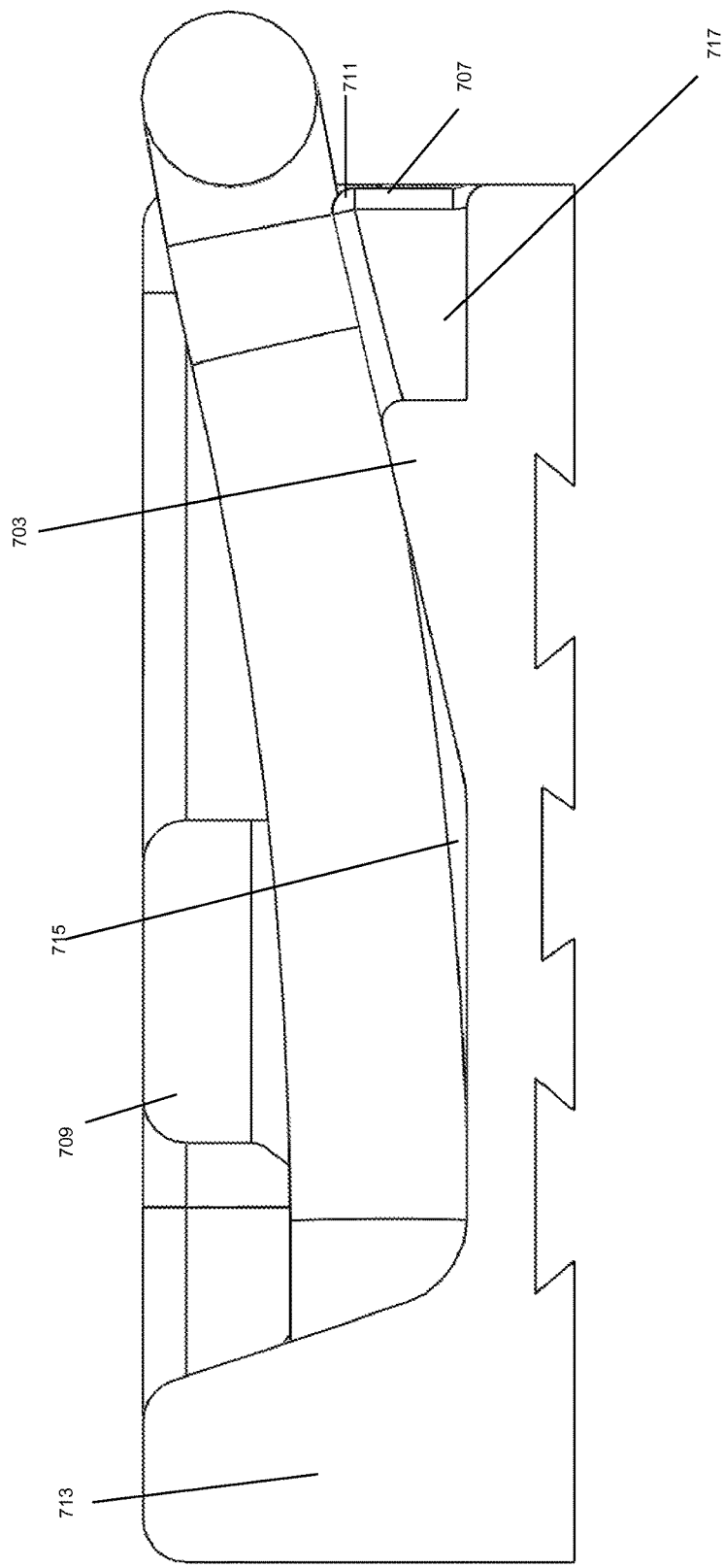

FIGS. 7A-7F illustrate a different configuration of an orthodontic bracket 701 into which a male loop 719 of an archwire may be snap fitted. FIG. 7A illustrates the orthodontic bracket 701 without any male loop; FIG. 7B illustrates the orthodontic bracket 701 after the male loop 719 has been snapped into the orthodontic bracket 701; FIG. 7C is a cross-section of the view in FIG. 7B taken along the broken line 7C/E/F-7C/E/F' in FIG. 7B; FIG. 7D is a cross-section of the view in FIG. 7A taken along the broken line 7D-7D' in FIG. 5A; FIG. 7E is a cross-section of the view in FIG. 7B taken along the broken line 7C/E/F-7C/E/F' in FIG. 7B when a height 711 blocks the withdraw of the male loop 719; and FIG. 7F is a cross-section of the view in FIG. 7B taken along the broken line 7C/E/F-7C/E/F' in FIG. 7B when the male loop 719 is lifted beyond the height 711 to allow withdraw of the male loop 719.

The components in FIGS. 7A-7F may be the same as the corresponding components in FIGS. 3A-3H, except as now noted.

One functional difference between the embodiments in FIGS. 7A-7F and 5A-5E may be that the springboard 703 may be a nonmoving member. To snap fit the loop male 719 into the orthodontic bracket 701, the male loop 719 may be deflected within its elastic limit as it rides over the springboard 703 during its insertion path. A description of this mechanism is provided below.

The springboard 703 may be a non-movable member. The most occlusal portion of the springboard 703 may be a springboard end 707. The springboard end 707 may have an access port 717 that allows an instrument to access underneath the archwire when it is in the snapped position. The springboard end 707 may be in a position that is always occlusal to a bridge 709. The distance between the floor 715 and the edge of the springboard end 707 that is furthest away from the floor 715 may be the height 711 of the springboard 703. The angle between the springboard 703 and the floor 715 may be such that: (1) the distance between the floor 715 and the height 711 of the springboard 703 is more than the distance between the floor 715 and the base side of the bridge 709; (2) the distance between the floor 715 and the base side of the bridge 709 is more than the diameter of the archwire, allowing for the male loop 719 to pass through during insertion of the archwire 353; and (3) the minimum distance between the floor 715 and the height 711 of the springboard 703 is half the diameter of the male loop 719.

The bridge 709 may be narrower in the occlusal-gingival direction than in what is shown in FIGS. 3A-3H. The bridge 709 may not contain the access port 717.

The stop 713 may not contain a springboard opening, a springboard slot, a springboard slot outside opening, or a springboard slot inside opening.

The floor 715 may have only one level.

To snap an archwire into the orthodontic bracket 701, the operator may take the same steps as described in connection with the embodiment in FIGS. 3A-3H. However, side bars of the male loop 719 may slide along a vertical archwire slot 723, and the arc of the male loop 719 may glide over the springboard body 705 towards the springboard end 707, causing the male loop 719 to deflect within its elastic limits to the active archwire unlocking state. Once the arc of male loop 719 is pushed past the height 711 of the springboard 703 located at the springboard end 707, the male loop 719 may move from the active archwire unlocking state to the passive archwire locking state.

To unsnap the male loop 719, an instrument may be inserted into the access port 717 to lift the male loop 719 from the passive archwire locking position (FIG. 7E) to the active archwire unlocking position (FIG. 7F). When the male loop 719 is in the active archwire unlocking position (FIG. 7F), a force may be exerted in the gingival direction upon the orthodontic bracket legs 725 or the arc of the male loop 719, disengaging the male loop 719 from the orthodontic bracket 701. As the male loop 719 is disengaged from the orthodontic bracket 701, the male loop 107 may return to the passive archwire locking position (FIG. 7E).

Figure 8A:
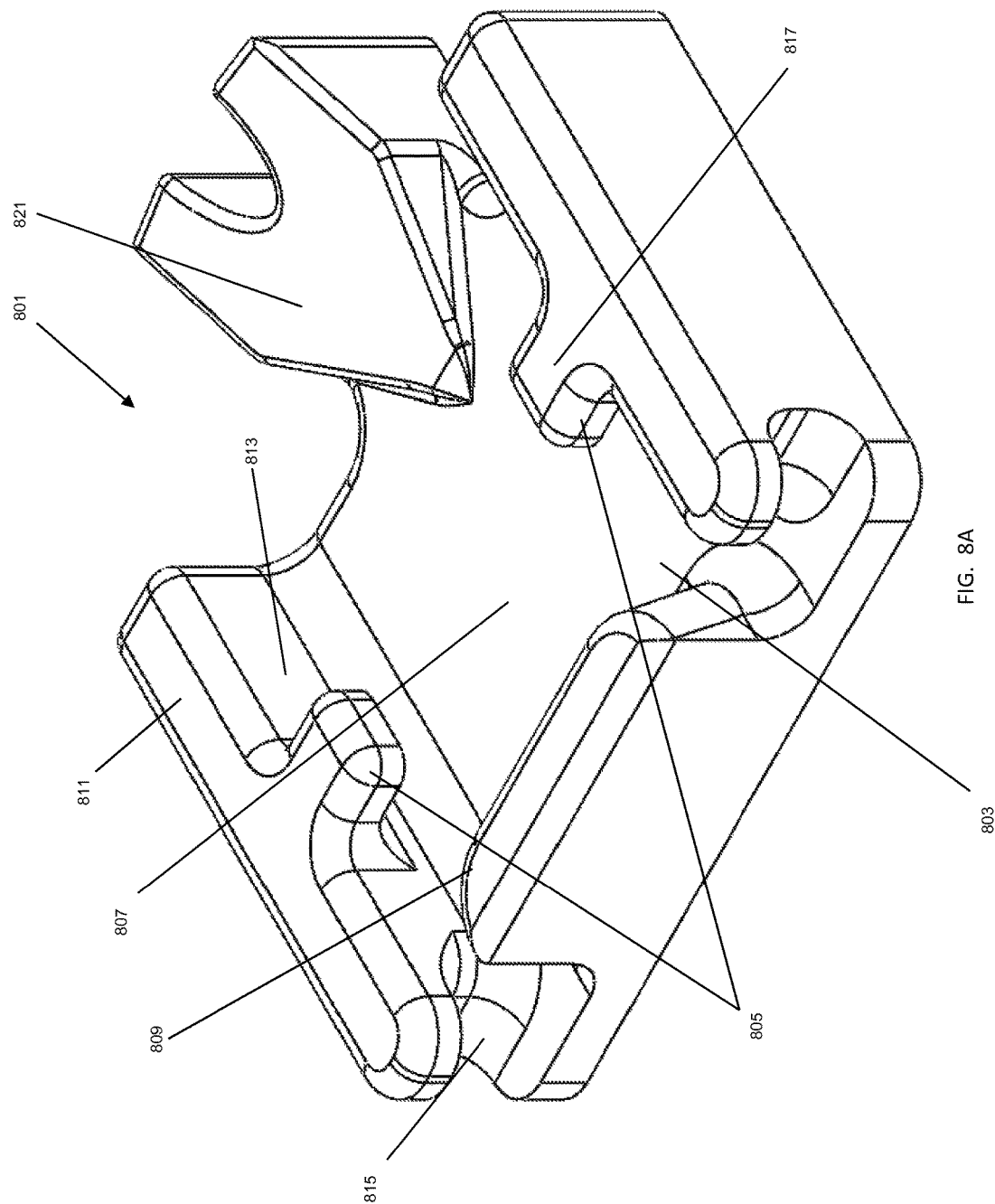
FIGS. 8A-8E illustrate a different configuration of an orthodontic bracket into which a male loop of an archwire may be snap fitted.
Figure 8B:
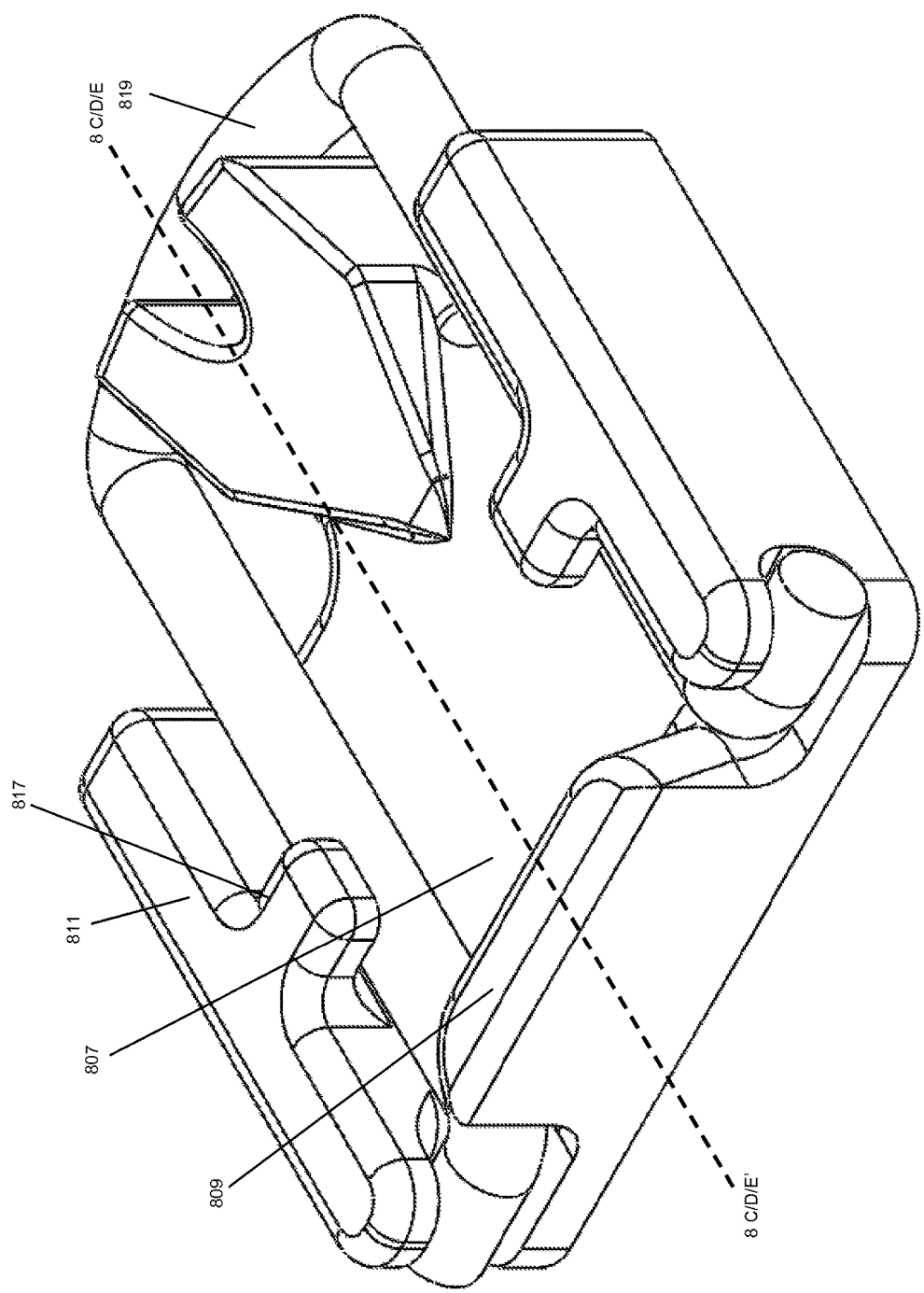
Figure 8C:
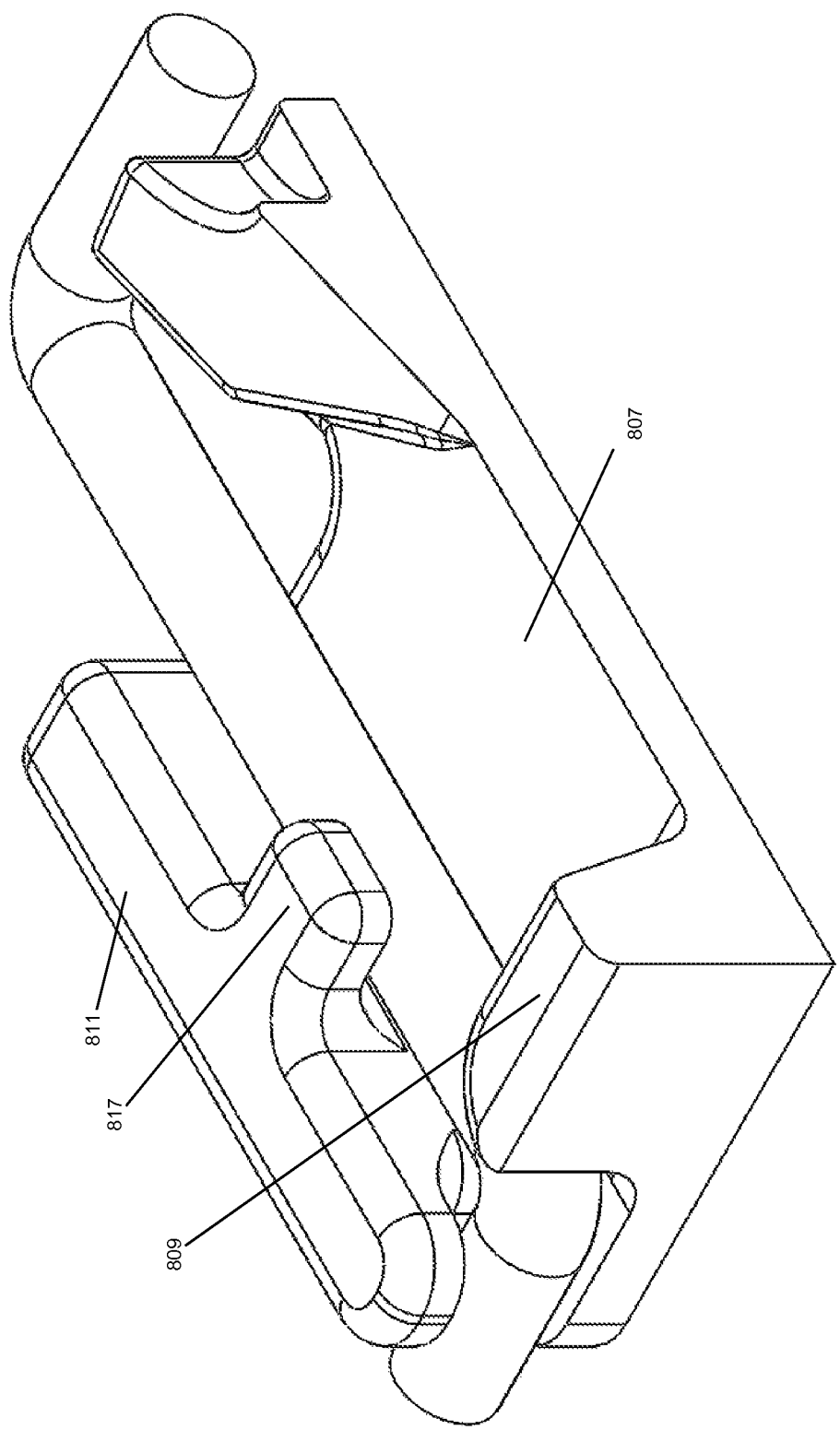
Figure 8D:
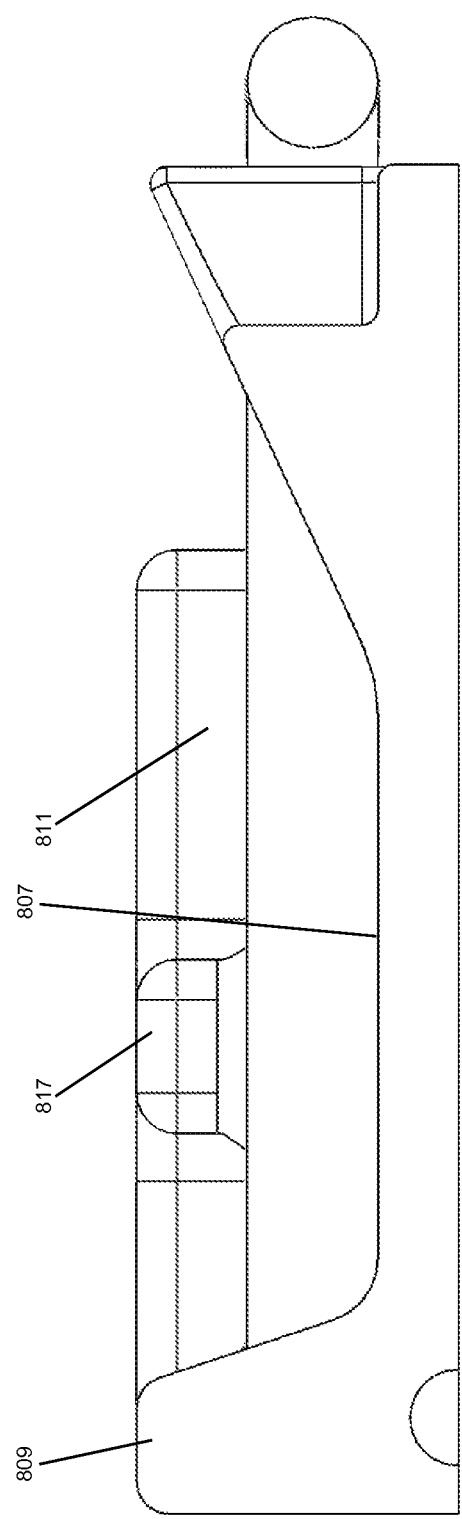
Figure 8E:
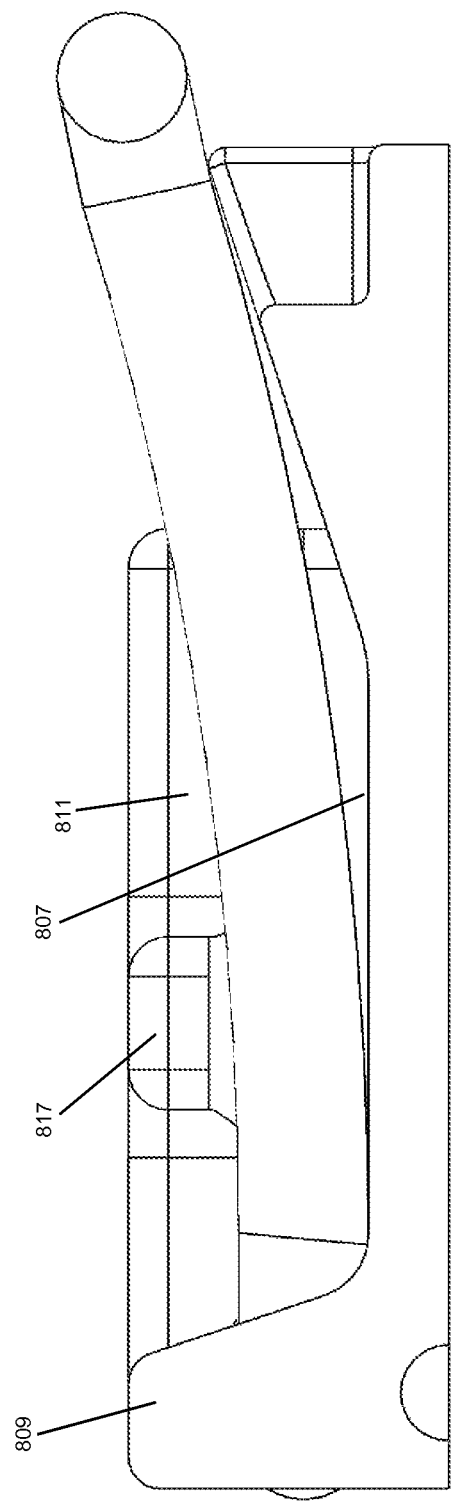

FIGS. 8A-8E illustrate a different configuration of an orthodontic bracket 801 into which a male loop 821 of an archwire may be snap fitted. FIG. 8A illustrates the orthodontic bracket 801 without any male loop; FIG. 8B illustrates the orthodontic bracket 801 after the loop 821 has been snapped into the orthodontic bracket; FIG. 8C is a cross-section of the view in FIG. 8B taken along the broken line 8C/D/E-8C/D/E' in FIG. 8B; FIG. 8D is a cross-section of the view in FIG. 8B taken along the broken line 8C/E/F-8C/E/F' in FIG. 8B when the height 822 blocks the withdraw of the male loop 821; and FIG. 8F is a cross-section of the view in FIG. 8B taken along the broken line 8C/E/F-8C/E/F' in FIG. 8B when the male loop 821 is lifted beyond the height 822 to allow withdraw of the male loop 821.

The components in FIGS. 8A-8E may be the same as the corresponding components in FIGS. 7A-7F, except as now noted.

The bridge 805 may be formed by an orthodontic bracket rail protuberance 819 that extends from a mesial orthodontic bracket rail 813 and an orthodontic bracket rail protuberance 819 that extends from the distal orthodontic bracket rail 813. Both orthodontic bracket rail protuberances 819 may extend towards but may not join at the center of the orthodontic bracket 801.

The area of the orthodontic bracket body 803 located near the occlusal end of the springboard 703 may be cut away to reduce bulk of the orthodontic bracket base.

To snap and unsnap the loop 821 into or out of the orthodontic bracket 801, the same steps may be taken that are discussed above in connection with 7A-7F.

Figure 9A:
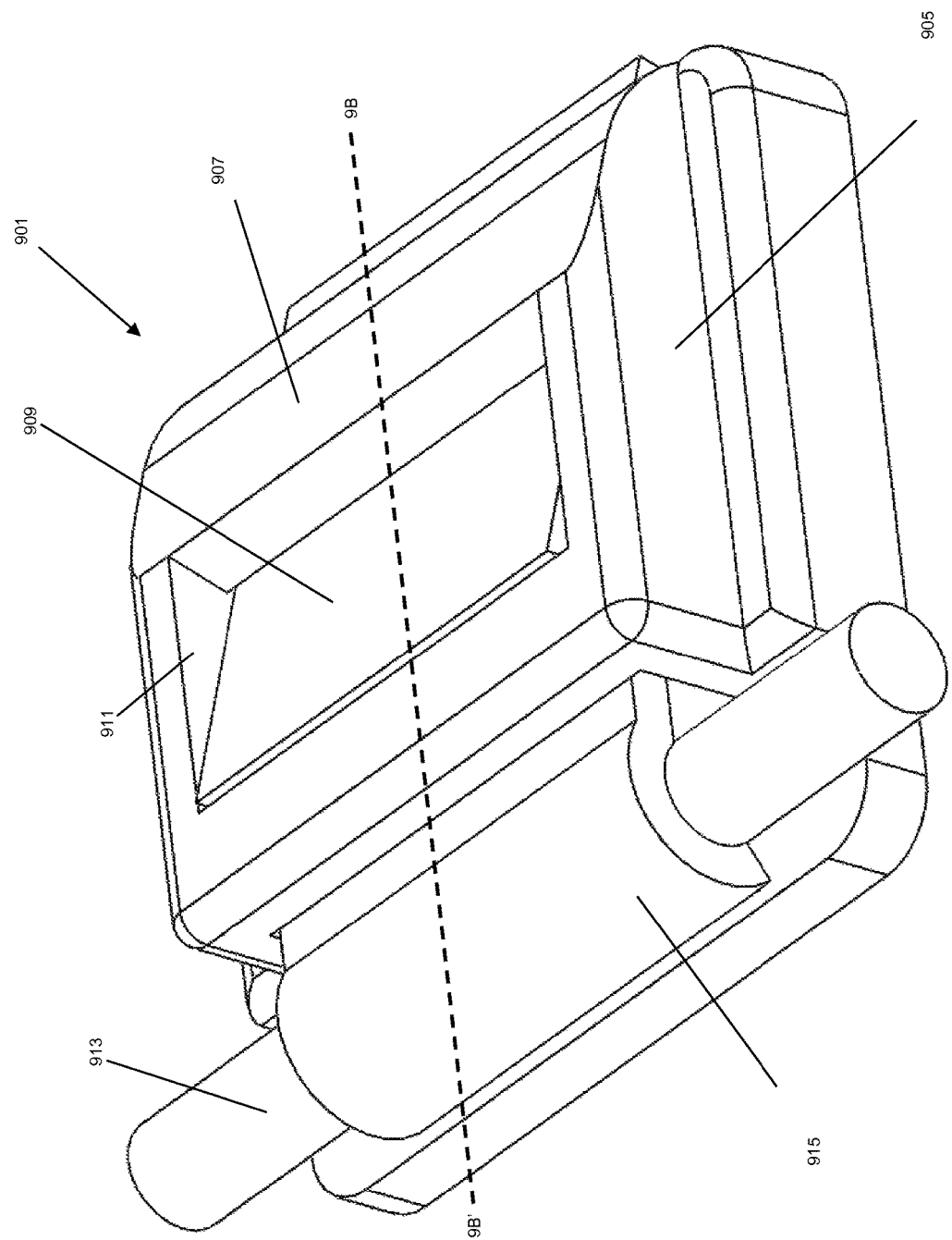
FIGS. 9A-9B illustrate a different configuration of an orthodontic bracket and a different configuration of an archwire.
Figure 9B:
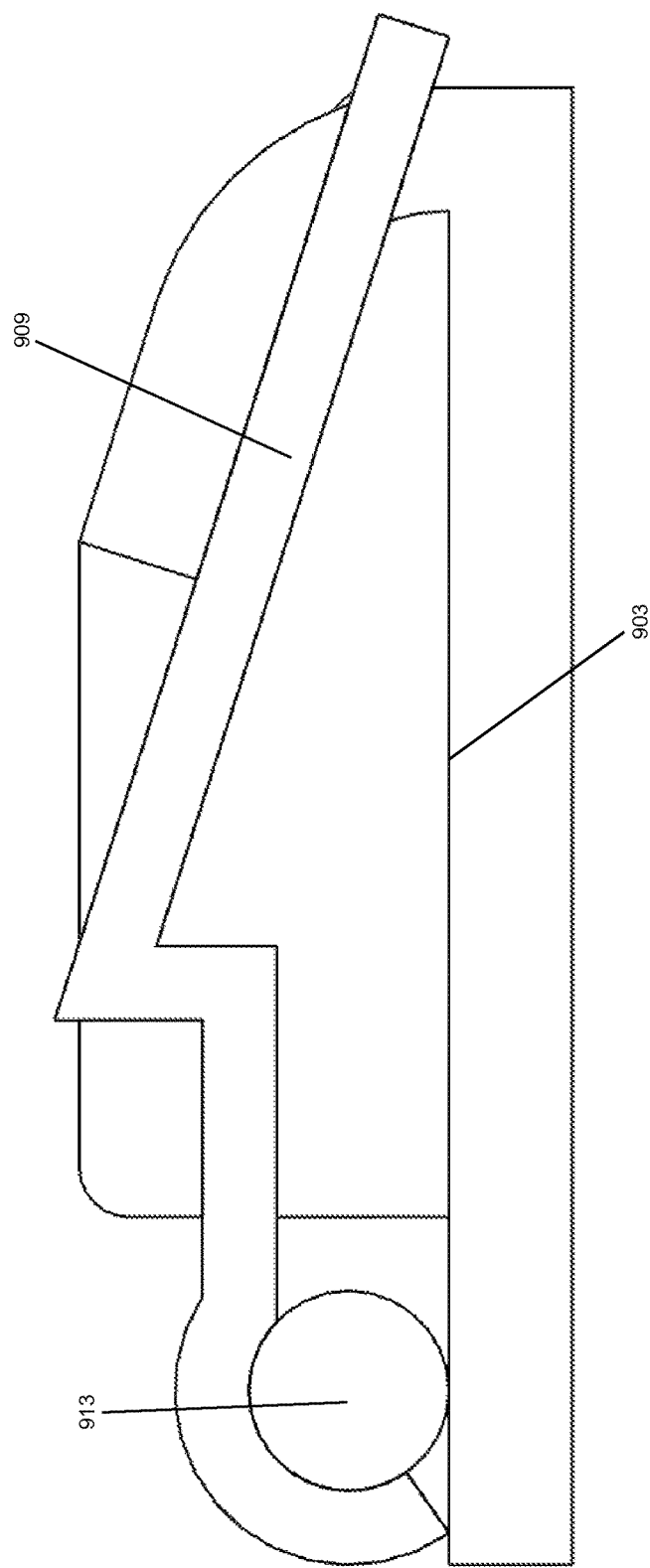

FIGS. 9A-9B illustrate a different configuration of an orthodontic bracket 901 and a different configuration of an archwire 913. FIG. 9A illustrates the orthodontic bracket 901 and the archwire 913 in snapped position. FIG. 9B is a cross-section of the view in FIG. 9A taken along the broken line 9B-9B'.

The male loops discussed above may be replaced with a male locking insert 915. This insert 915 may have various shapes, such as a triangular cross section. The male locking insert 915 may cooperate with a springboard 909.

The orthodontic bracket 901 may have a space to receive the male locking insert 915 that is surrounded by four walls: a floor 903, mesial and distal side walls 905, and a bridge 907. The opening 911 may be in about the middle of the bridge 907. The bridge 907 on the side where the insert 915 enters the orthodontic bracket 901 may be level with the floor 903. The bridge 907 on the opposite side may be slanted to meet with the floor 903. That bridge 907 may match the slant of the springboard 909.

To snap the archwire 913 in place, the springboard 909 may be inserted into the orthodontic bracket 901 with its height facing a rectangular opening 911. The insertion may force the height to deflect, causing the lowering of its profile and allowing it to snap into the orthodontic bracket 901. Once the height of the springboard 909 passes the bridge 907 on the gingival side of the opening 911, the springboard 909 may recover from the deflection, returning the profile of the springboard 909 to its original height and locking the insert 915 in place.

To unsnap the insert 915, an instrument may be used to press on the height of the springboard 909 through the opening 911 to cause the springboard 909 to deflect. The profile of the springboard 909 may be lowered until the height is below the bridge 907 to allow withdrawal of the insert 915.

Figure 10A:
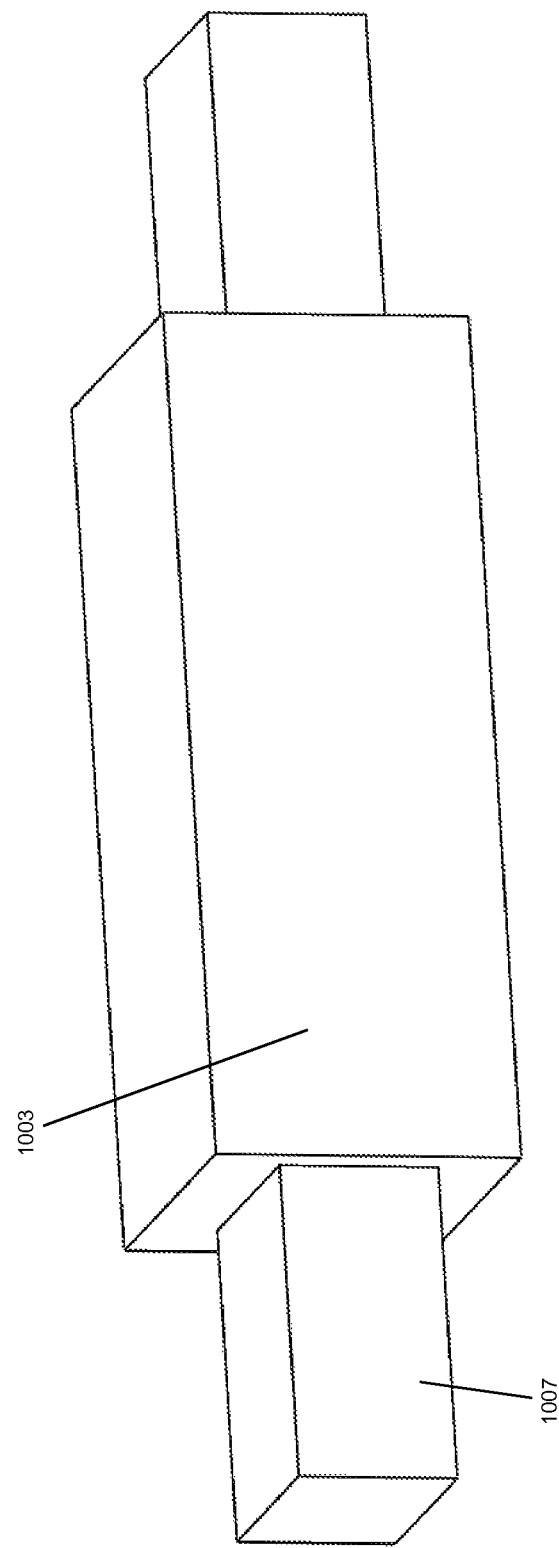
FIGS. 10A-10C illustrate a different configuration of an orthodontic bracket and a different configuration of an archwire.
Figure 10B:
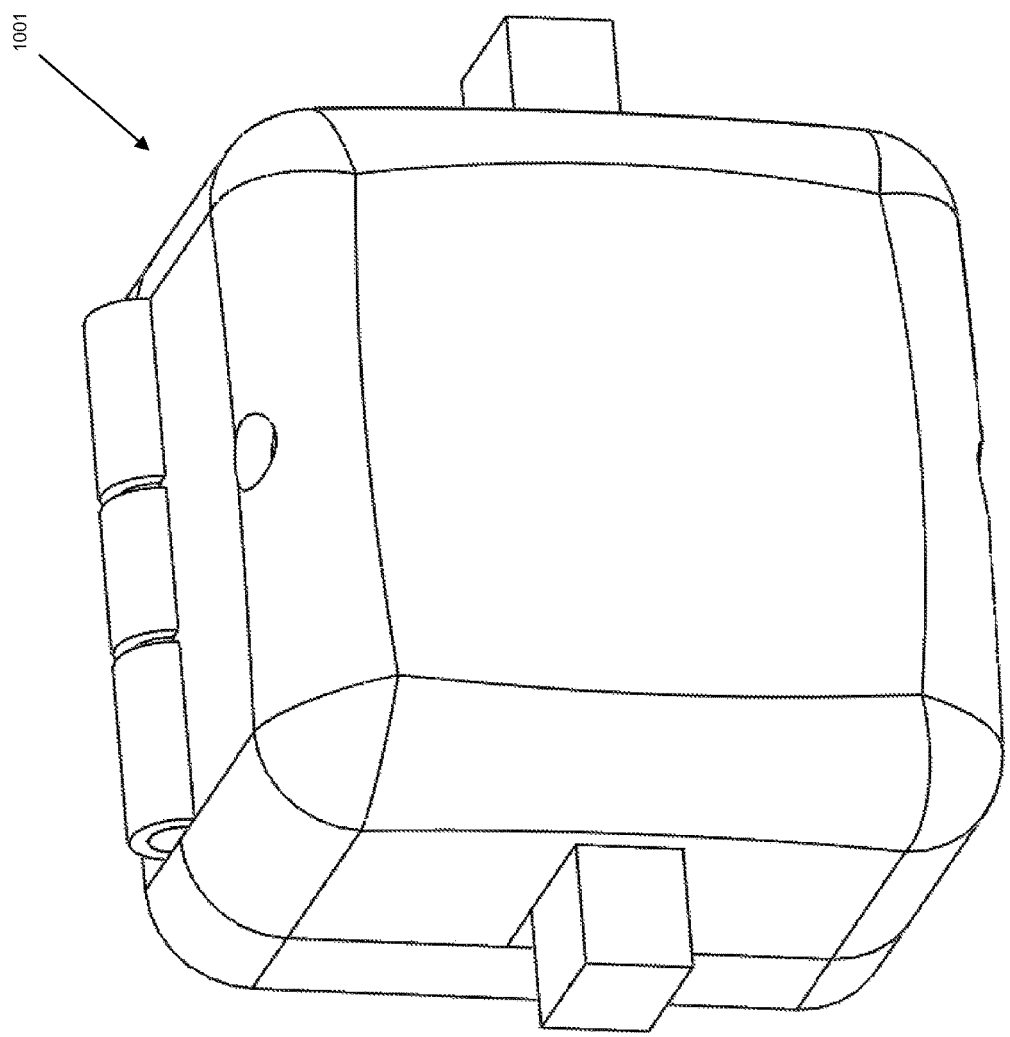
Figure 10C:
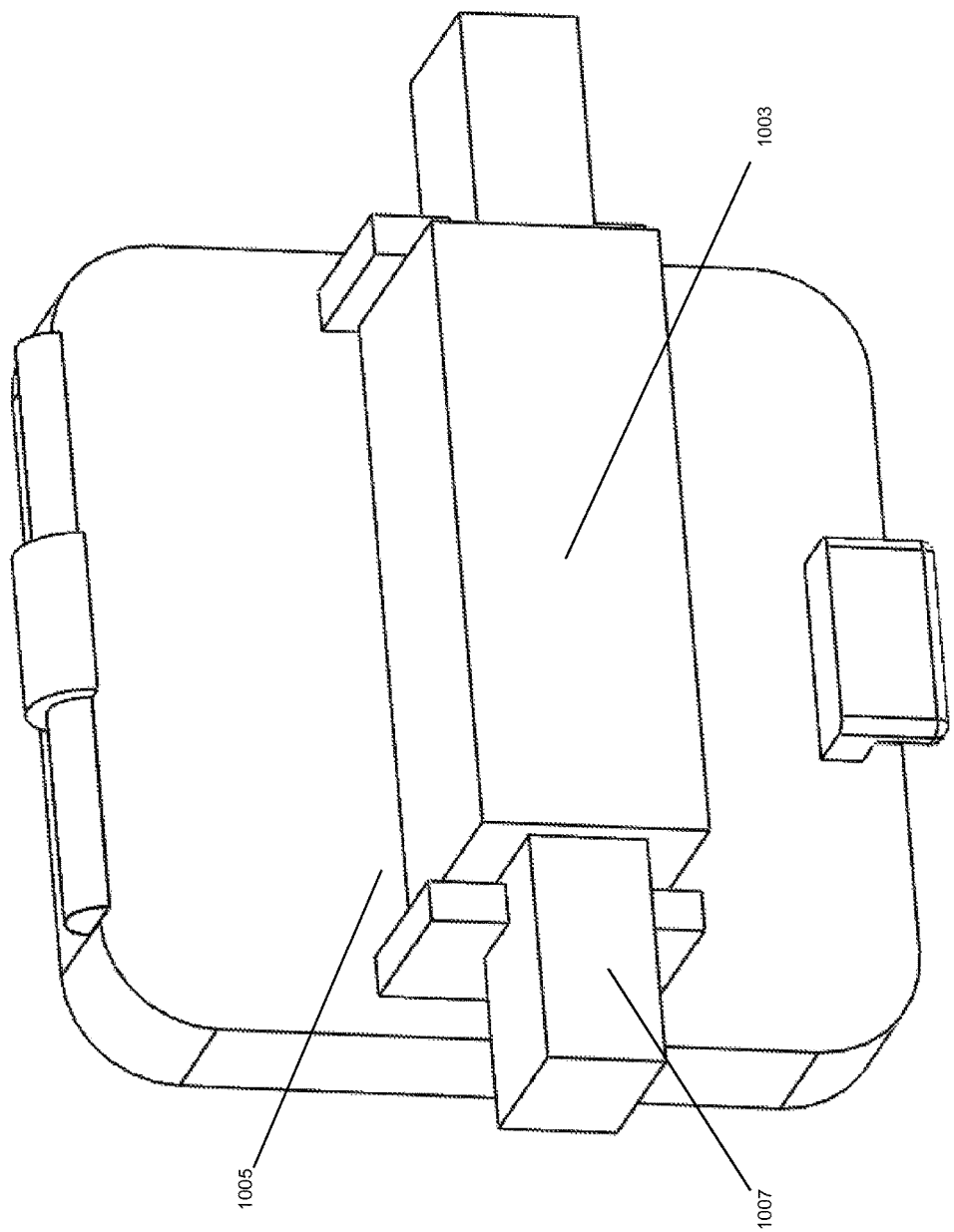

FIGS. 10A-10C illustrate a different configuration of an orthodontic bracket 1001 and a different configuration of an archwire 1007. FIG. 10A illustrates the archwire 1007 with a protuberance 1003. FIG. 10B illustrates an example of the orthodontic bracket 1001 that may be a self-ligating bracket modified to have the compartment 1005. Other types of orthodontic brackets could similarly be modified to have the compartment 1005, such as a twin bracket, a single wing bracket, or a ribbon arch bracket. FIG. 10C shows the orthodontic bracket 1001 in FIG. 10A with the self-ligating door removed.

The male loops may be replaced with stops, eyelets, indentations, or any type of protuberance 1003 that allows control of the orthodontic bracket 1001 in three dimensions, while also preventing the archwire 1007 from sliding after it is engaged with the orthodontic bracket 1001. A vertical tube can be added to the protuberance 1003 to allow auxiliaries such as hooks to be added when necessary.

The orthodontic bracket 1001 may be in the form of any orthodontic bracket, such a self-ligating bracket, a twin bracket, a single wing bracket, or a ribbon arch bracket. The orthodontic bracket 1001 may be modified such that there is the compartment 1005 in the internal aspect of the orthodontic bracket 1001 to receive the protuberance 1003 in such a way that allows the protuberance 1003 to couple forces with the orthodontic bracket 1001 in three dimensions in a non-sliding manner.

Figure 11:
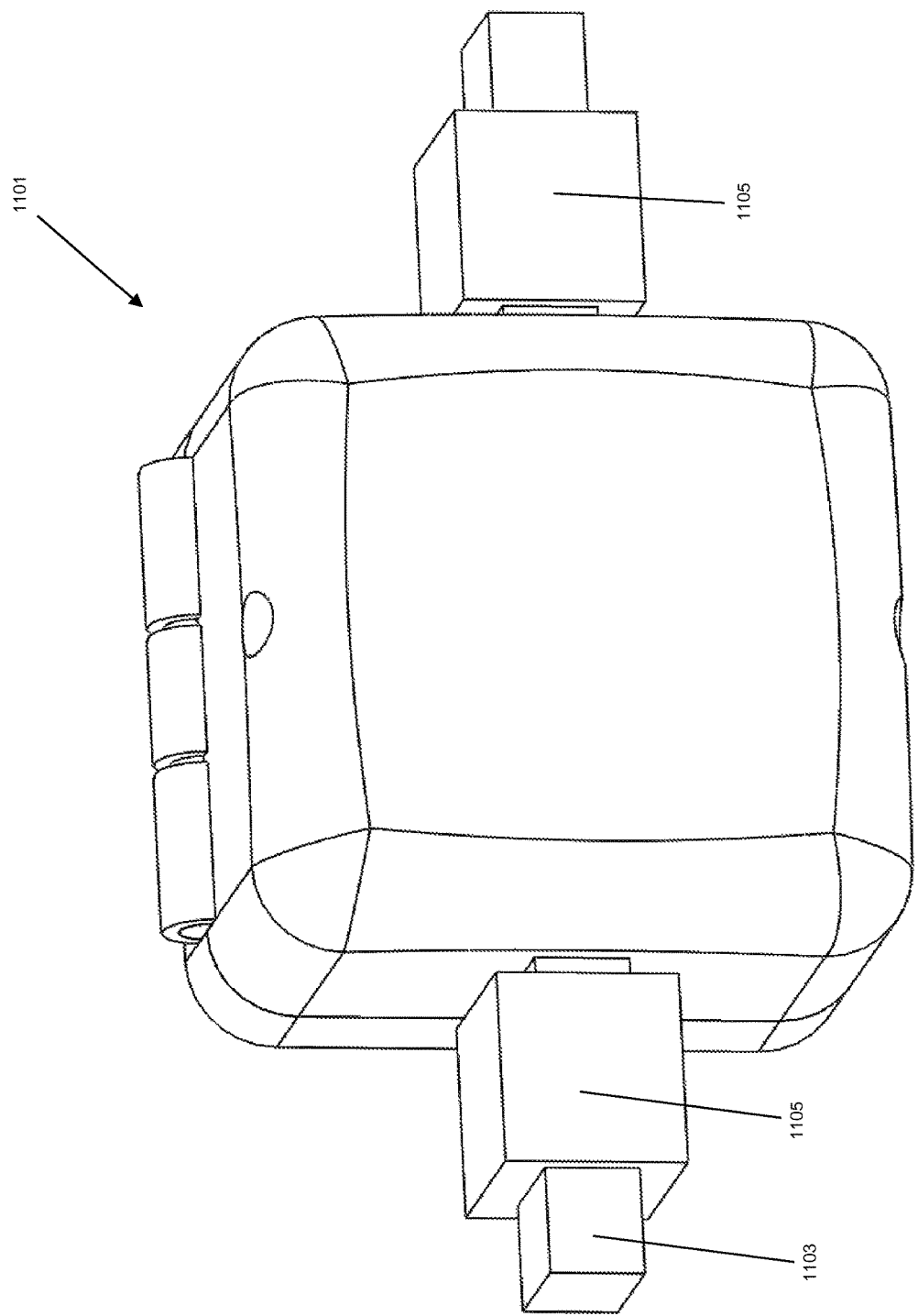
FIG. 11 illustrates a different configuration of an orthodontic bracket and a different configuration of an archwire.

FIG. 11A illustrates a different configuration of an orthodontic bracket 1101 and a different configuration of an archwire 1103.

Archwire male loops may be removed and replaced with stops, eyelets, indentations, or any type of protuberance 1105 on the mesial and distal aspects of the orthodontic bracket 1101. These protuberances may act as stops to prevent the archwire 1103 from sliding.

The bracket 1101 may be any type orthodontic bracket, such as a self-ligating bracket, a twin bracket, a single wing bracket, or a ribbon arch bracket.

An archwire may be activated by deflecting it away from its default position and inserting into a snapped position within an orthodontic bracket that is bonded to a tooth. When this elastic deflection occurs, the archwire may exert a reaction force in the direction that returns the archwire to the designed configuration, thereby transferring forces to the tooth and causing orthodontic tooth movement.

This archwire activation may completely control any tooth movement in three-dimensional space.

For mesio-distal tooth movement, if there is space between adjacent teeth, snap fitting an archwire into an orthodontic bracket may cause an interproximal loop to open, which may cause the archwire to be activated, leading to closing of space in the mesial-distal direction. Whereas, if there is overlap between adjacent teeth, archwire snap fitting into an orthodontic bracket may cause an interproximal loop to close, which may cause the archwire also to be activated, this time leading to opening of space in the mesial-distal direction.

For occlusal-gingival tooth movement, if the adjacent teeth are not at the same level, an archwire snap fitting into an orthodontic bracket may cause connecting archwire legs and interproximal loops to deflect in a slanted manner which may cause the archwire to be activated, leading to tooth correction in the occlusal-gingival direction.

For facio-lingual tooth movement, archwire snap fitting into an orthodontic bracket may cause the wire to be pushed away from its original position which may cause the archwire to be activated, leading to tooth correction in the facio-lingual direction.

The various configurations of archwires and orthodontic brackets that have been discussed may provide one or more advantages. These are now discussed.

There may be superior mesio-distal angulation and facio-lingual inclination orthodontic control because the vertical male loop may offer a longer arm for coupling forces to the orthodontic bracket when compared to the rectangular dimensions of an edgewise appliance. Moreover, the spread of the two parallel side bars of the male loop may make them function like a twin orthodontic bracket in providing a force couple in dealing with any axial rotation.

The interproximal loops may allow the operator to adjust the rigidity of the archwire, which may provide versatility for the same archwire diameter to be used in a wide array of cases.

The interproximal loops can be designed to allow patients to easily floss while undergoing orthodontic treatment.

The interproximal loops may be designed to have a certain type of shape (such as a "boot" or a "tear"). These shapes can be used to hold elastic rubber bands.

The archwire may be designed such that it can be activated to move the teeth. This type activation may be self-activating and self-limiting because it may not require use of external forces such as power chain and coil springs to move the teeth. This type of activation may also be self-limiting because the archwire may only exert forces that return the archwire to its original shape, negating the need for frequent appointments.

This approach may also not permit sliding of the archwire with respect to the orthodontic bracket, thus making movement of the teeth much more predictable.

The orthodontic bracket can be manufactured using casting, metal injection molding, 3D printing, micromachining, any combination of generic mass production and customization techniques, and/or any direct digital manufacturing technique. The archwire can be bent by the operator, through a wire-bending robot, and/or through any other process that can set the shape of the wire to a pre-determined shape.

The orthodontic appliances that have been described may be used in various ways.

If the system has a base that is fully customized to the tooth, the steps are may include:

Images of teeth may be obtained by using a digital intra-oral scanner, a cone-beam computed tomography (CBCT) X-ray scanner, or by taking polyvinyl siloxane (PVS) impressions, followed by pouring of study models and scanning of the study model. Digital images of teeth can be rendered in imaging software where each tooth image can be segmented from the whole dental arch image and then re-arranged in an expected alignment, a process known as virtual set-up of teeth.

Baseless orthodontic bracket images may be digitally placed onto teeth in locations that fit the preference of the user. Bases of orthodontic brackets may be custom designed with the tooth side of the bases fitting perfectly to the tooth surfaces where orthodontic brackets are to be bonded, and the orthodontic bracket side of the bases may merge and connect with the base side of the orthodontic bracket. At this point, orthodontic bracket positioning jigs may also be custom designed. Orthodontic bracket positioning jigs may be used to register the orthodontic bracket correctly to the tooth surface during bonding or rebonding of orthodontic brackets clinically.

Archwires may be custom designed to connect the generic male loops inside the orthodontic brackets with interproximal loops and the connecting archwire legs. The type and size of the interproximal loops may vary according to the required functions. The archwire legs may be designed to be parallel to the biting surface.

After designing custom orthodontic brackets, the positioning jigs and archwires may be complete. The virtual teeth set-up with the virtually designed orthodontic brackets, positioning jigs, and archwires may be sent to the user for approval and adjustments may be made according to the user's request.

Once finalized, the CAD model of the orthodontic brackets, positioning jigs, and archwires may be fabricated and shipped to the user.

On receiving the custom made orthodontic brackets and positioning jigs, the user can bond individual orthodontic brackets on the teeth directly by using the positioning jigs as a guide. Alternatively, orthodontic brackets can be bonded to the teeth via an orthodontic indirect bonding method, which may allow bonding of many orthodontic brackets at the same time. When indirect bonding with the help of the positioning jigs, orthodontic brackets may be bonded onto a physical model of patients' teeth obtained either through 3D printing or via a dental impression.

An indirect bonding tray may be fabricated using a process which transfers the exact location of the orthodontic brackets on the physical model to the indirect bonding tray.

After removal of orthodontic brackets from model teeth, the orthodontic brackets may undergo processes such as sandblasting to remove debris from the orthodontic bracket base as well as increasing bonding strength.

The orthodontic archwire and indirect bonding tray with orthodontic brackets intact may be shipped to user.

User may receive the orthodontic brackets imbedded in the indirect bonding trays and a number of standard indirect bonding procedures can be performed to bond the orthodontic brackets to the patients' teeth clinically.

If orthodontic brackets with semi-custom made bases or completely generic baseless orthodontic brackets are used, users may choose to bond them directly to the teeth. However, positioning jigs may need to be custom made in the event of rebonding to position the orthodontic brackets back to the exact position as the initial bonding. Archwires may also be custom made. Therefore, images of teeth after initial bonding may be obtained via intra-oral scanning and CBCT scanning. Alternatively, the lower profile of the orthodontic brackets may allow use of PVS impression for image acquisition. Again, the images may be rendered in an imaging software program where each tooth image can be segmented from the whole dental arch image so that teeth can be reset virtually in expected alignment.

The design and fabrication of custom positioning jigs and archwires may be carried out in the same way as described previously. Once received by user, the first set of archwires can be delivered to the patients' teeth with orthodontic brackets already bonded. The positioning jigs may be kept in case an orthodontic bracket breaks from the tooth and needs to be rebounded. Alternatively, instead of waiting for the fabrication of custom archwires, a semi-custom made initial archwires may be delivered immediately after initial bonding. These archwires may only be used temporarily until the user receives the fully custom-made archwires. The generic archwires may be made to fit teeth of a number of different sizes in a few common alignments.

The various portions of the various brackets that have been described may be all part of a single integration piece of material, such as steel, aluminum, nickel-titanium, any other shape memory alloy, or any other metal alloy, ceramic, zirconia, dental composite, or any other plastic material. One or more of these components may instead be formed separately from the others.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An orthodontic appliance comprising:
   an archwire comprising a shape memory material, the archwire forming a single continuous wire and comprising a length that fits within a human mouth and comprising a curved shape configured to follow a dental arch,
   the archwire comprising a plurality of male loops, each male loop of the plurality of male loops corresponding to an individual tooth of the dental arch such that the plurality of male loops correspond to each and every tooth of the dental arch,
   the archwire also comprising a plurality of interproximal looped structures each being entirely offset from the curved shape of the archwire, each interproximal looped structure of the plurality of interproximal loop structures corresponding to an interdental space between a tooth of the dental arch such that the plurality of interproximal looped structures correspond to each and every interdental space,
   wherein each interproximal looped structure of the plurality of interproximal looped structures are interspersed between each and every male loop,
   wherein the curved shape of the archwire defines a longitudinal axis and wherein each interproximal loop comprises a mesial point on the longitudinal axis, a distal point on the longitudinal axis, and an incomplete loop between the mesial point and the distal point extending away from the longitudinal axis, the incomplete loop defining a gap along the longitudinal axis forming an opening into the incomplete loop, the opening configured to face in a gingival or an occlusal direction; and
   wherein the archwire comprises an unbiased customized and memorized shape along the entire length of the wire, in which no forces are applied to the archwire, the customized and memorized shape being based on a predetermined planned configuration of a patient's teeth, being configured to be created from a virtual set-up utilizing image data from the patient's teeth, and being configured to move the teeth from an initial configuration to the predetermined planned configuration, wherein the customized and memorized shape further comprises an asymmetrical arrangement of the interproximal looped structures and a facial/lingual inclination of at least some of the male loops; and
   multiple orthodontic brackets, each having a configuration that facilitates attaching each orthodontic bracket to a single tooth and that allows one of the male loops to be:
   locked into the orthodontic bracket, each of the male loops being unable to slide with respect to the orthodontic bracket after being locked in each of the orthodontic brackets; and
   unlocked from the orthodontic bracket,
   wherein when the male loops are locked in each respective orthodontic bracket, the plurality of interproximal looped structures are configured to deflect, thereby transferring forces to the teeth and causing orthodontic tooth movement.

2. The orthodontic appliance of claim 1 wherein each male loop has a U or rectangular shape.

3. The orthodontic appliance of claim 1 wherein each male loop is an integral portion of the archwire.

4. The orthodontic appliance of claim 1 wherein the interproximal looped structures face in the same direction as the male loops.

5. The orthodontic appliance of claim 1 wherein the interproximal looped structures face in the opposite direction as the male loops.

6. The orthodontic appliance of claim 1 wherein each orthodontic bracket comprises a slot configured to house the male loops.

7. The orthodontic appliance of claim 6 wherein each slot has an inclined surface across which a portion of each of the male loops slide.

8. The orthodontic appliance of claim 7 wherein each inclined surface ends in an edge over which a portion of each of the male loops slide while each of the male loops is being inserted into the orthodontic bracket.

9. The orthodontic appliance of claim 8 wherein each slot has two parallel rails that surround and contact an exterior portion of each of the male loops and prevent each of the male loops from moving laterally with respect to the orthodontic bracket after each of the male loops is inserted into the orthodontic bracket and locked.

10. The orthodontic appliance of claim 9 wherein each slot has a floor that contacts a side of each of the male loops and that comes between each of the male loops and the tooth to which the orthodontic bracket is attached after each of the male loops is inserted into the orthodontic bracket and locked.

11. The orthodontic appliance of claim 7 wherein each slot has a bridge that contacts a portion of each of the male loops after each of the male loops is inserted into the orthodontic bracket and locked.

12. The orthodontic appliance of claim 10 wherein each inclined surface bends while each of the male loops is being inserted into the orthodontic bracket and unbends after each of the male loops is locked in the orthodontic bracket.

13. The orthodontic appliance of claim 7 wherein each inclined surface does not bend while each male loop is being inserted into each orthodontic bracket.

14. The orthodontic appliance of claim 6 wherein:
the archwire includes two legs connecting each male loop to the archwire; and
each slot includes two concave portions that each seat one of the two legs during the locking.

15. The orthodontic appliance of claim 1 wherein:
each male loop has side legs; and
each orthodontic bracket includes a stop that prevents the side legs from collapsing when each male loop is locked in the orthodontic bracket.

16. An orthodontic appliance comprising:
an archwire comprising a shape memory material,
the archwire forming a single continuous wire configured to fit within a human mouth and comprising a curved shape configured to follow a dental arch,
the archwire comprising a plurality of male loops, each male loop of the plurality of male loops corresponding to an individual tooth of the dental arch such that the plurality of male loops correspond to each and every tooth of the dental arch,
the archwire also comprising a plurality of interproximal looped structures each being offset from the curved shape of the archwire, each interproximal looped structure of the plurality of interproximal loop structures corresponding to an interdental space between a tooth of the dental arch such that the plurality of interproximal looped structures correspond to each and every interdental space,
wherein each interproximal looped structure of the plurality of interproximal looped structures are interspersed between each and every male loop,
wherein the archwire comprises an unbiased customized and memorized shape along the entire length of the wire, in which no forces are applied to the archwire, the customized and memorized shape being based on a predetermined planned configuration of a patient's teeth, being configured to be created from a virtual set-up utilizing image data from the patient's teeth, and being configured to move the teeth from an initial configuration to the predetermined planned configuration, wherein the customized and memorized shape further comprises an asymmetrical arrangement of the interproximal looped structures and a facial/lingual inclination of at least some of the male loops; and
wherein the curved shape of the archwire defines a longitudinal axis and wherein each interproximal loop comprises a mesial point on the longitudinal axis, a distal point on the longitudinal axis, and an incomplete loop extending away from the longitudinal axis between the mesial point and the distal point, the archwire extending along the incomplete loop from the mesial point to the distal point without forming a complete loop; and
multiple orthodontic brackets, each having a configuration that facilitates attaching each orthodontic bracket to a single tooth and that allows one of the male loops to be:
locked into the orthodontic bracket, each of the male loops being unable to slide with respect to the orthodontic bracket after being locked in each of the orthodontic brackets; and
unlocked from the orthodontic bracket,
wherein when the male loops are locked in each respective orthodontic bracket, the plurality of interproximal looped structures are configured to deflect, thereby transferring forces to the teeth and causing orthodontic tooth movement.

17. The orthodontic appliance of claim 16 wherein each interproximal loop structure is interconnected to an adjacent male loop by a linear leg portion of the archwire, each linear leg portion being aligned with the direction of the dental arch such that a torque imparted around a longitudinal axis of the leg portion would exert a rotational force on the adjacent male loop, the rotational force being exerted primarily in a plane normal to a mesial-to-distal axis of the dental arch such that the rotational force is configured to alter the facial-lingual inclination of the adjacent male loop.

* * * * *

UNITED STATES PATENT AND TRADEMARK OFFICE
CERTIFICATE OF CORRECTION

PATENT NO. : 10,219,877 B2
APPLICATION NO. : 15/249198
DATED : March 5, 2019
INVENTOR(S) : Behrokh Khoshnevis It is certified that error appears in the above-identified patent and that said Letters Patent is hereby corrected as shown below:

On the Title Page

Page 3 (Item (56)), Column 2, Line 1, under Other Publications, change "/meas-therapy/" to --/meaw-therapy/--.

In the Claims

Column 20, Line 66, in Claim 11, change "claim 7" to --claim 10--.

Column 21, Line 3, in Claim 12, change "claim 10" to --claim 7--.

Signed and Sealed this
Third Day of September, 2019

Andrei Iancu
*Director of the United States Patent and Trademark Office*